US006045533A

United States Patent [19]
Kriesel et al.

[11] Patent Number: 6,045,533
[45] Date of Patent: Apr. 4, 2000

[54] FLUID DELIVERY DEVICE WITH CONFORMABLE ULLAGE AND FILL ASSEMBLY

[75] Inventors: Marshall S Kriesel, St. Paul; Farhad Kazemzadeh, Bloomington; Matthew B. Kriesel, St. Paul, all of Minn.; William W Feng, Lafayette, Calif.; Thomas N Thompson, Richfield, Minn.

[73] Assignee: Science Incorporated, Bloomington, Minn.

[21] Appl. No.: 09/183,328

[22] Filed: Oct. 29, 1998

Related U.S. Application Data

[60] Division of application No. 08/666,659, Jun. 18, 1996, Pat. No. 5,830,187, which is a continuation-in-part of application No. 08/577,779, Dec. 22, 1995, Pat. No. 5,807,335.

[51] Int. Cl.[7] .................................................. A61M 37/00
[52] U.S. Cl. ......................... 604/132; 604/151; 604/890.1
[58] Field of Search .................. 604/82, 83, 86, 604/131, 132, 151, 153, 890.1

[56] References Cited

U.S. PATENT DOCUMENTS

| 5,167,631 | 12/1992 | Thompson et al. | 604/132 |
| 5,176,641 | 1/1993 | Idriss | 604/133 |
| 5,267,957 | 12/1993 | Kriesel et al. | 604/85 |
| 5,336,188 | 8/1994 | Kriesel | 604/132 |
| 5,368,570 | 11/1994 | Thompson et al. | 604/131 |
| 5,484,410 | 1/1996 | Kriesel et al. | 604/89 |

*Primary Examiner*—Ronald Stright
*Assistant Examiner*—Jeremy Thissell
*Attorney, Agent, or Firm*—James E. Brunton

[57] ABSTRACT

A fluid delivery apparatus for continuous basal infusion, together with controlled bolus infusion of injectable medicaments, which embodies a stored energy source such as distendable elastomeric membrane which cooperates with a base and a conformable ullage to define a fluid reservoir and one which includes a unique fill assembly for use in controllably filling the fluid reservoir. The novel fill assembly of the invention enables the fluid reservoir of the fluid delivery portion of the apparatus to be aseptically filled in the field with a wide variety of selected medicinal fluids.

17 Claims, 35 Drawing Sheets

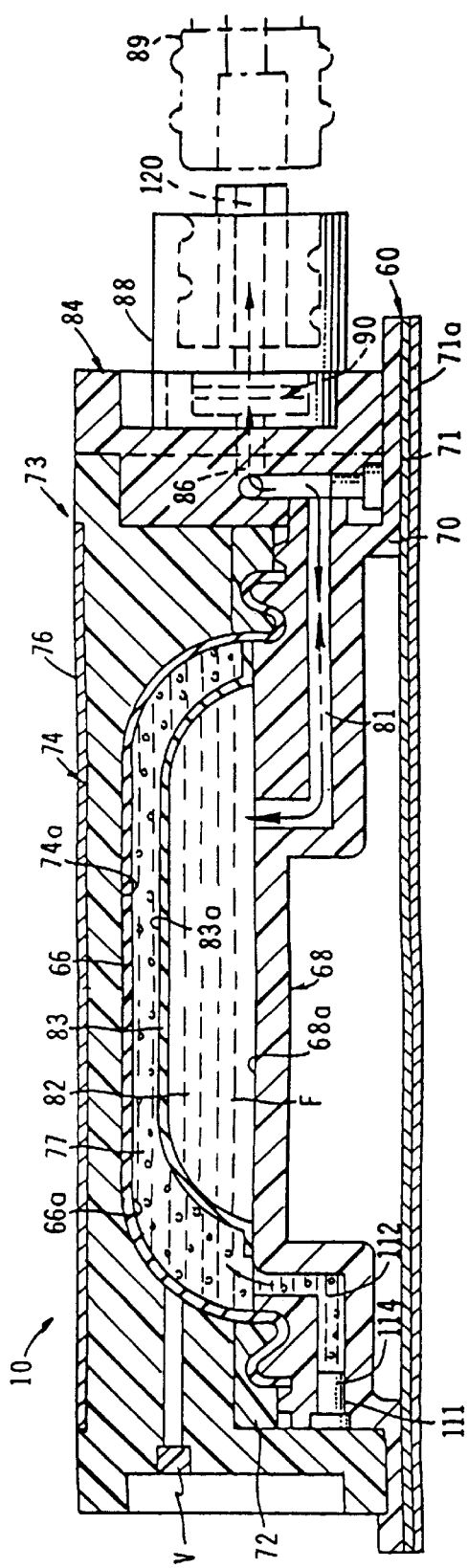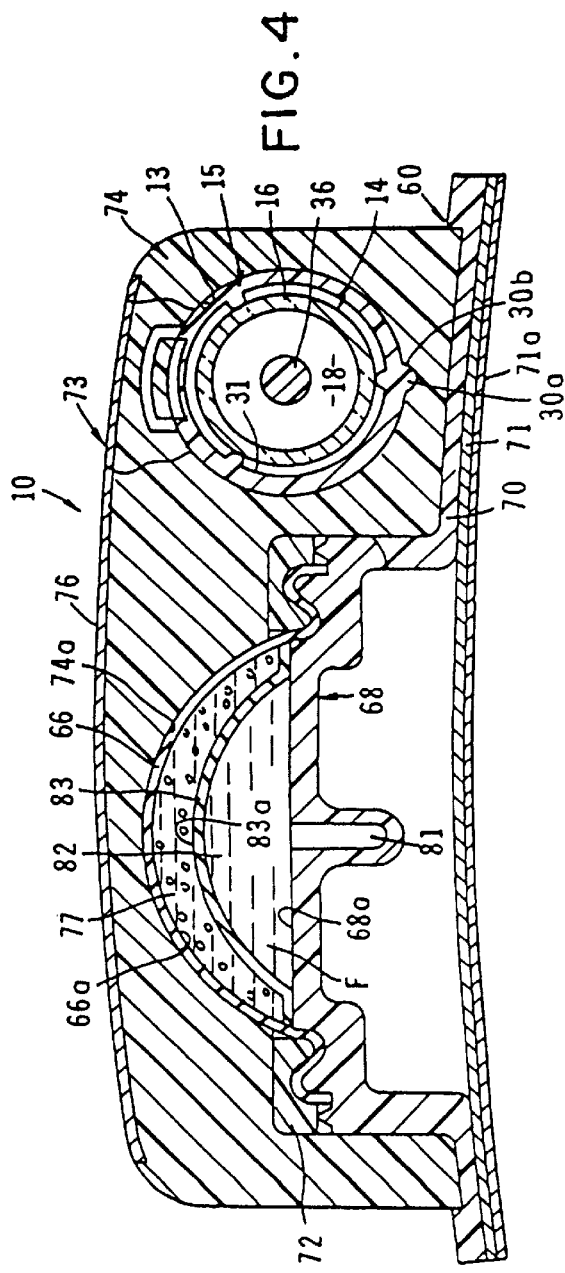

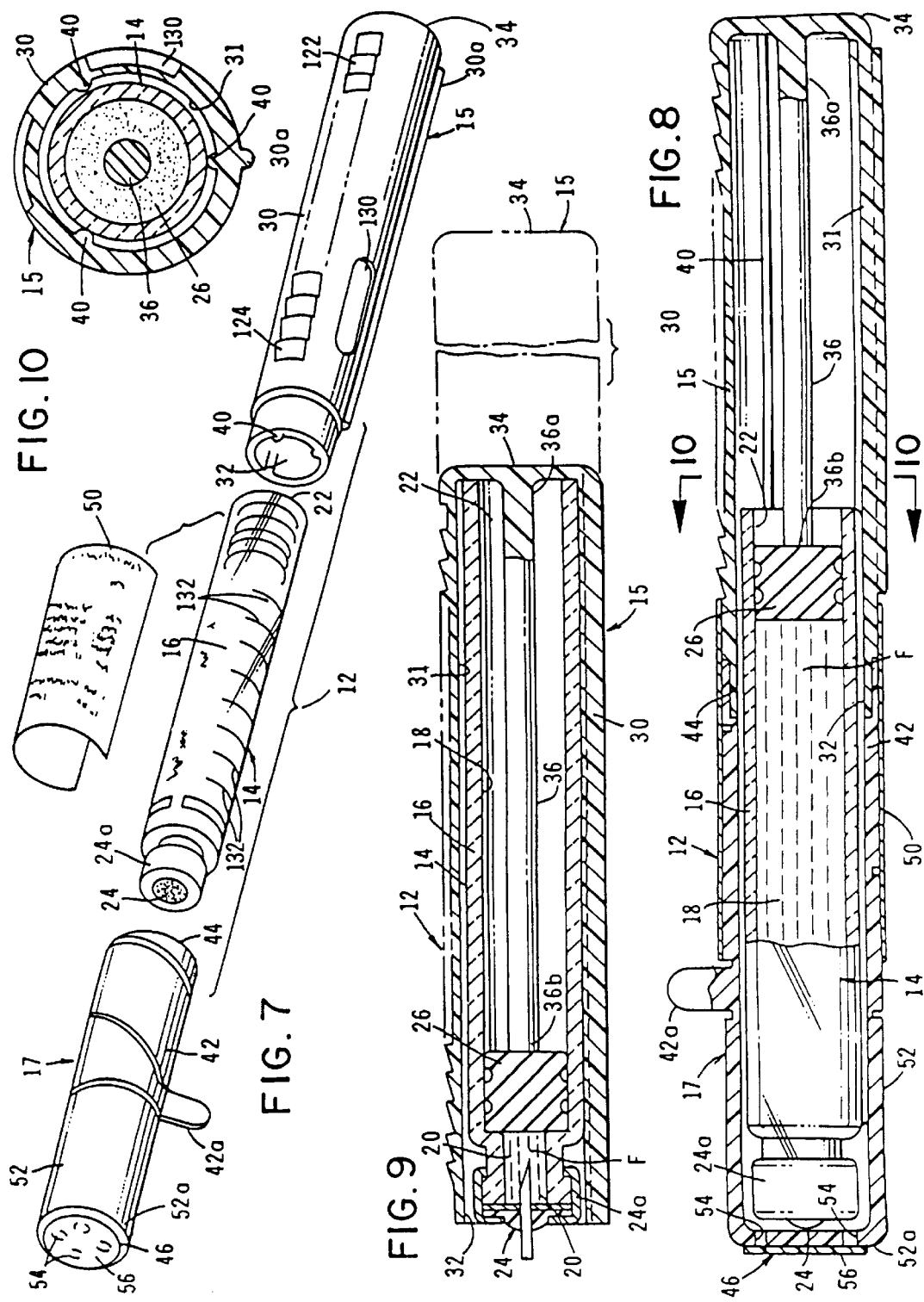

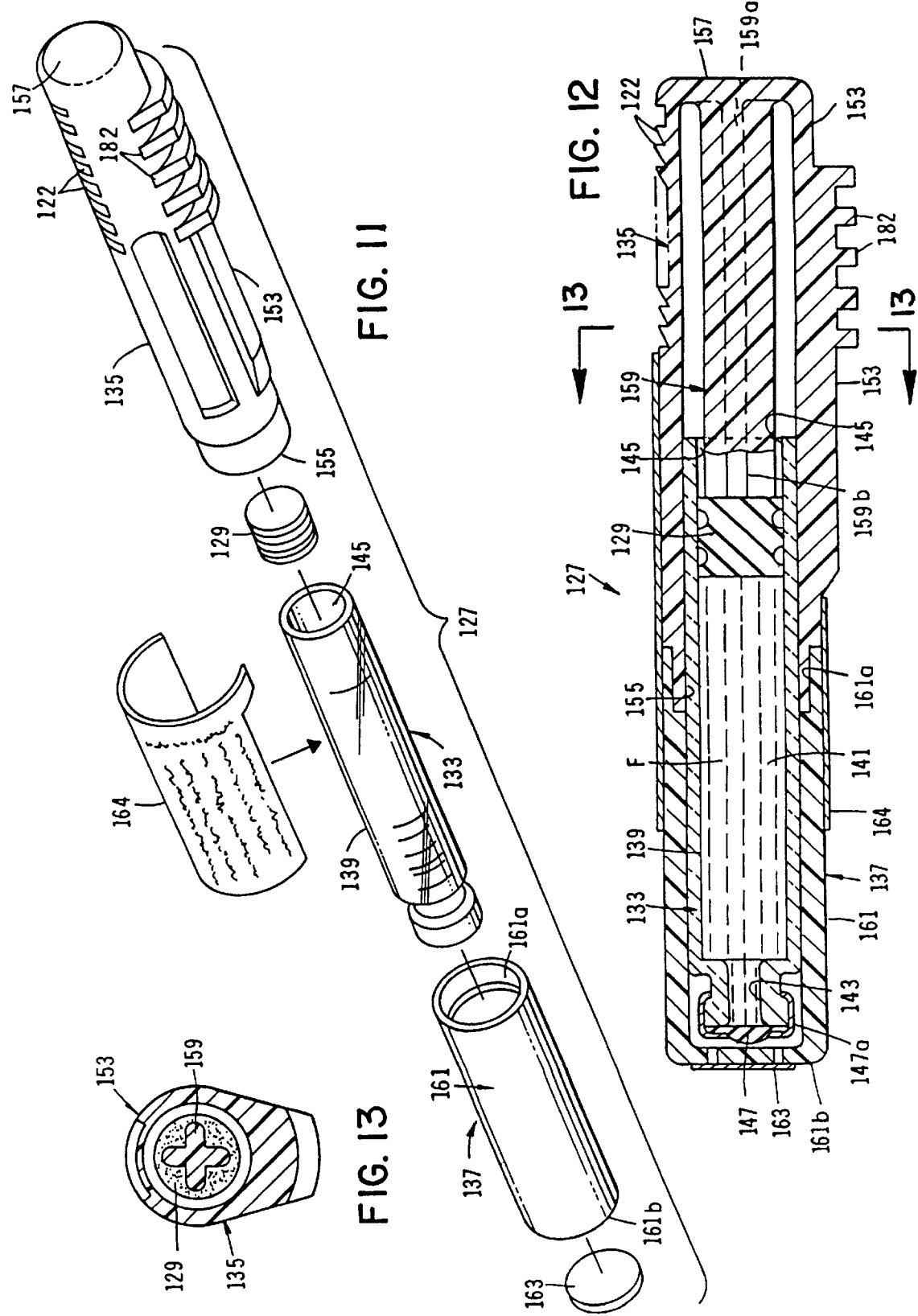

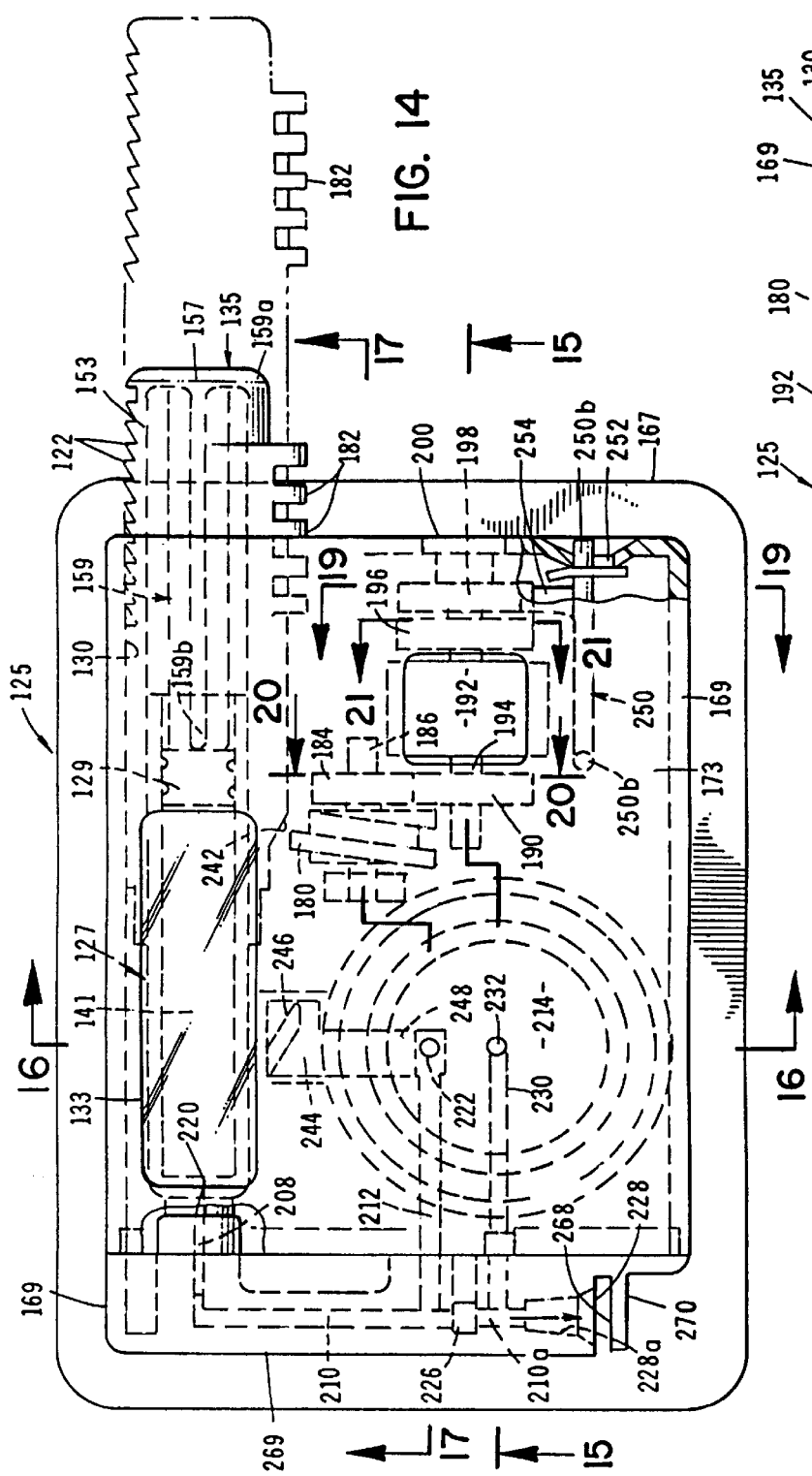
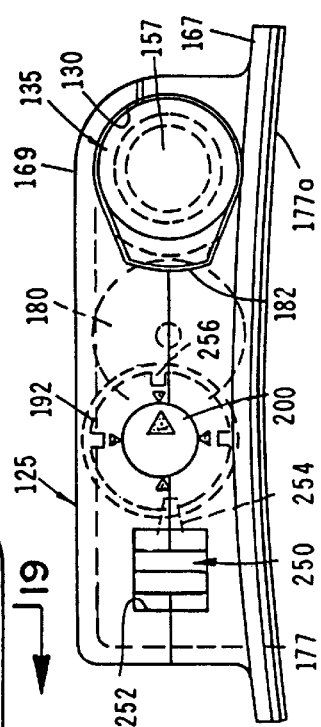

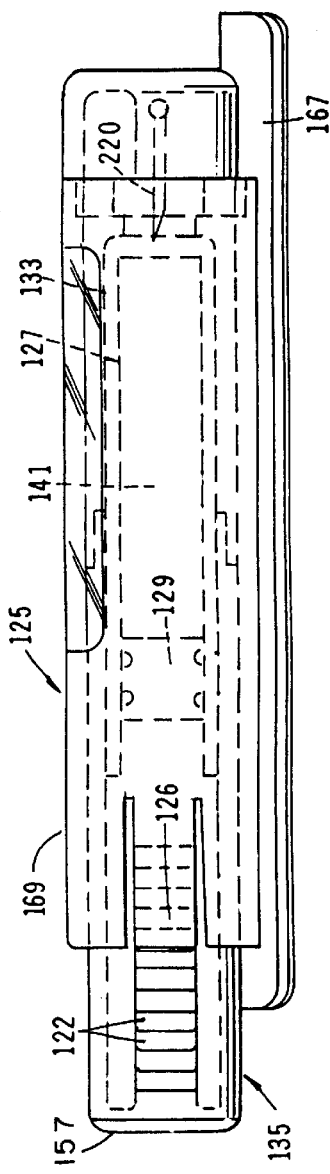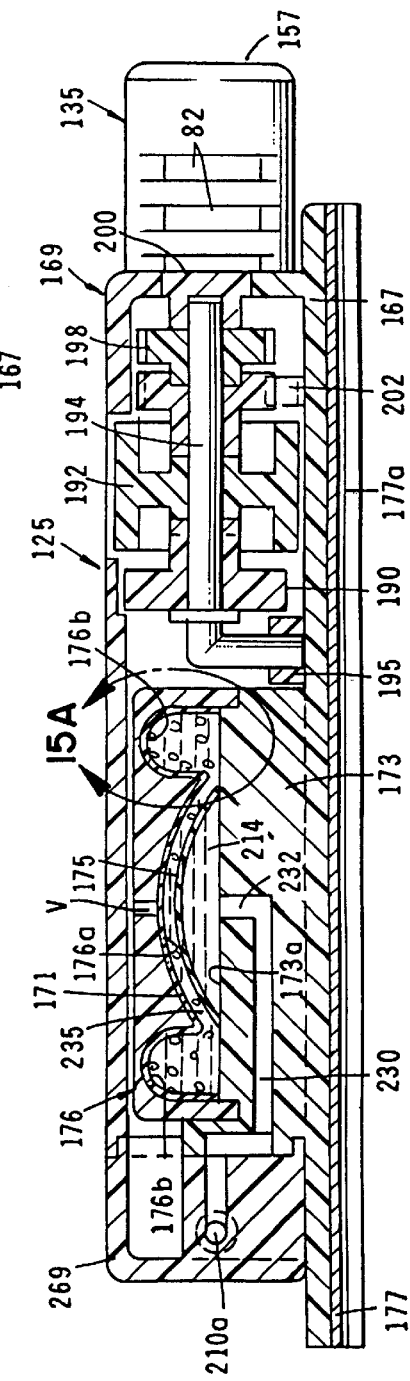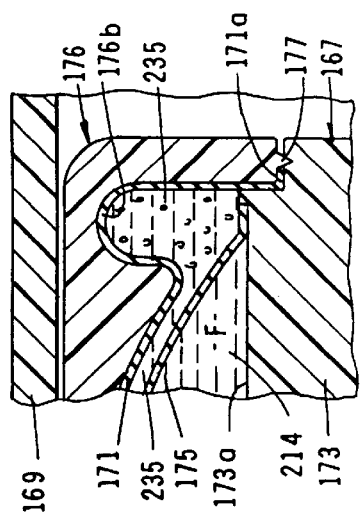

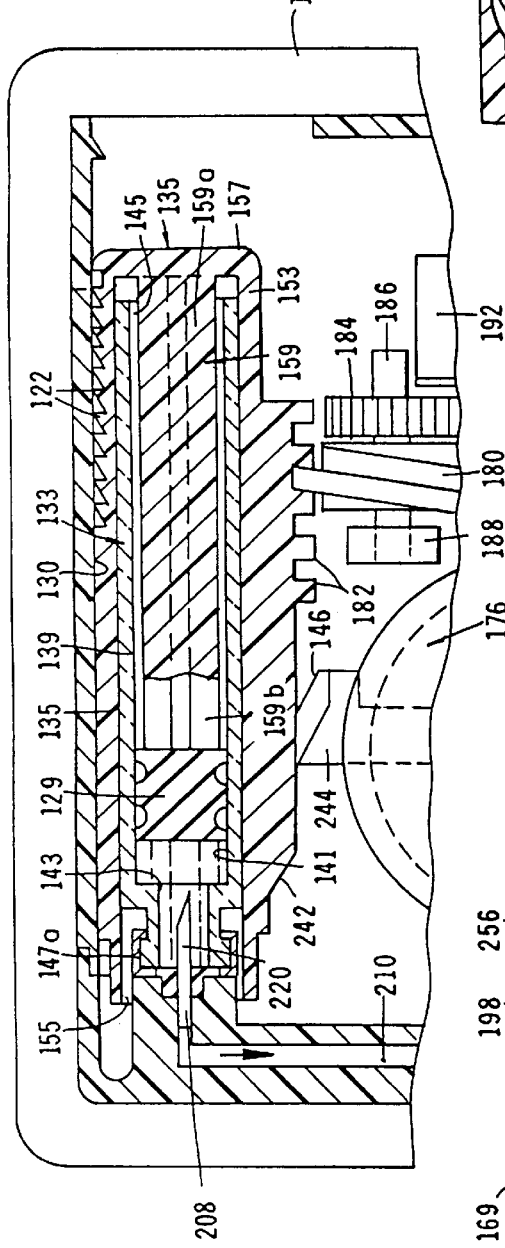
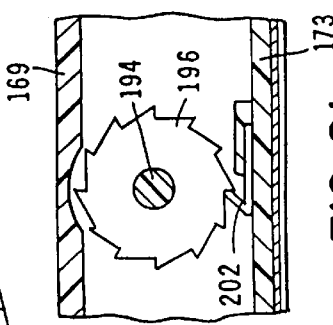
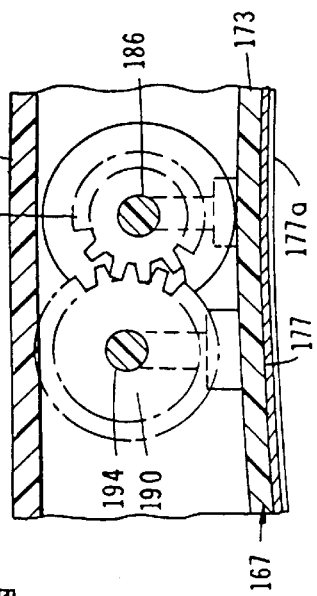
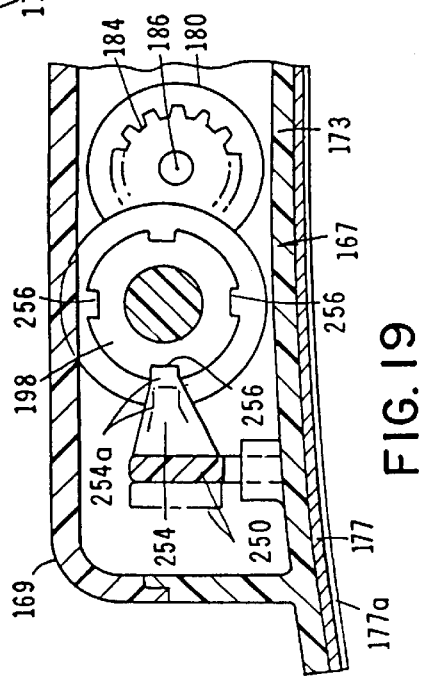

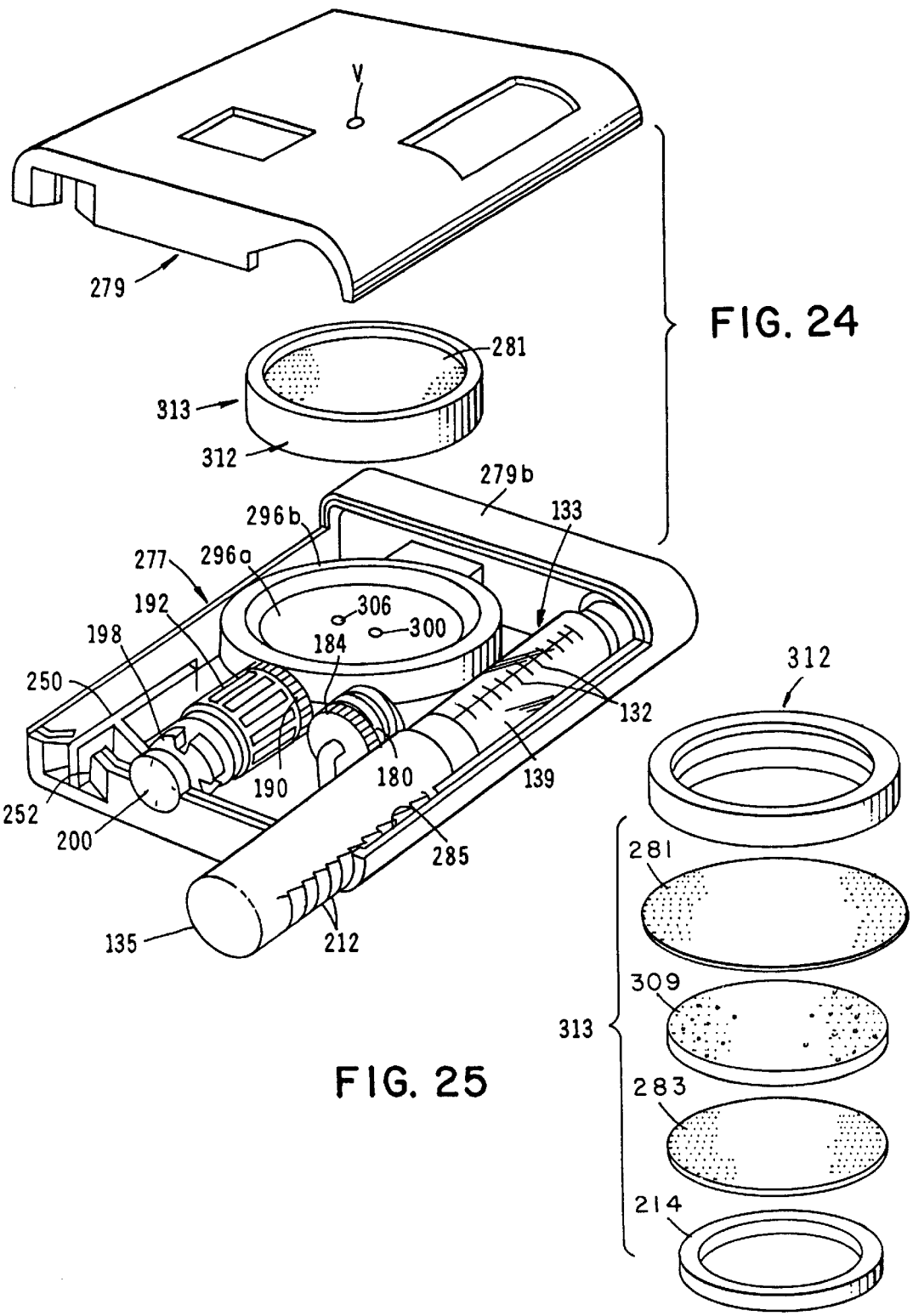

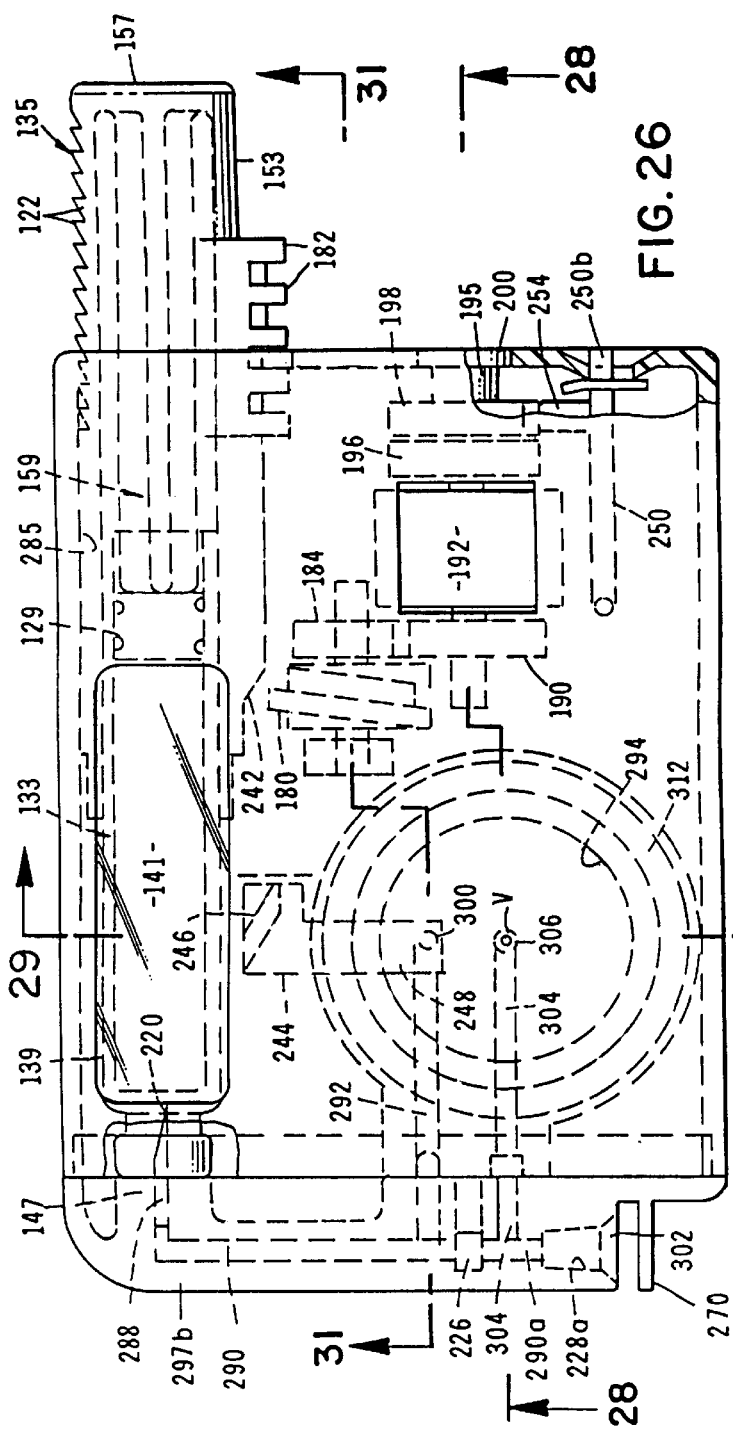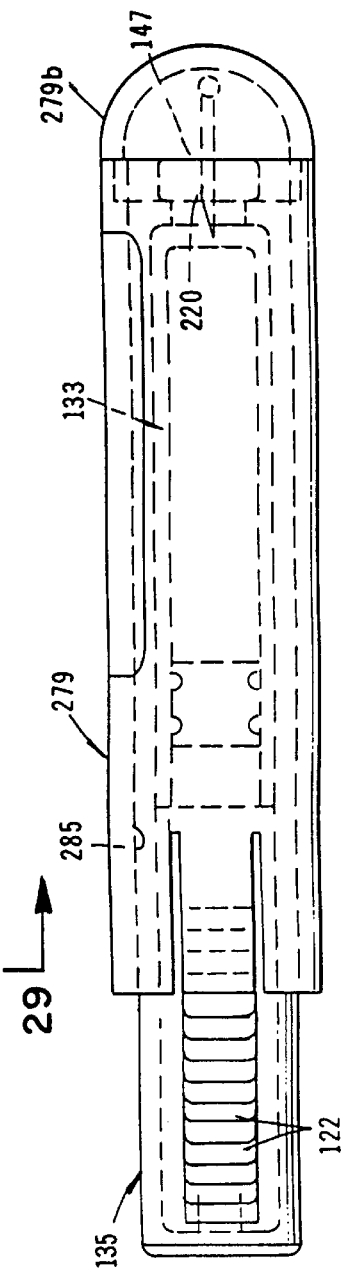
FIG. 26
FIG. 27

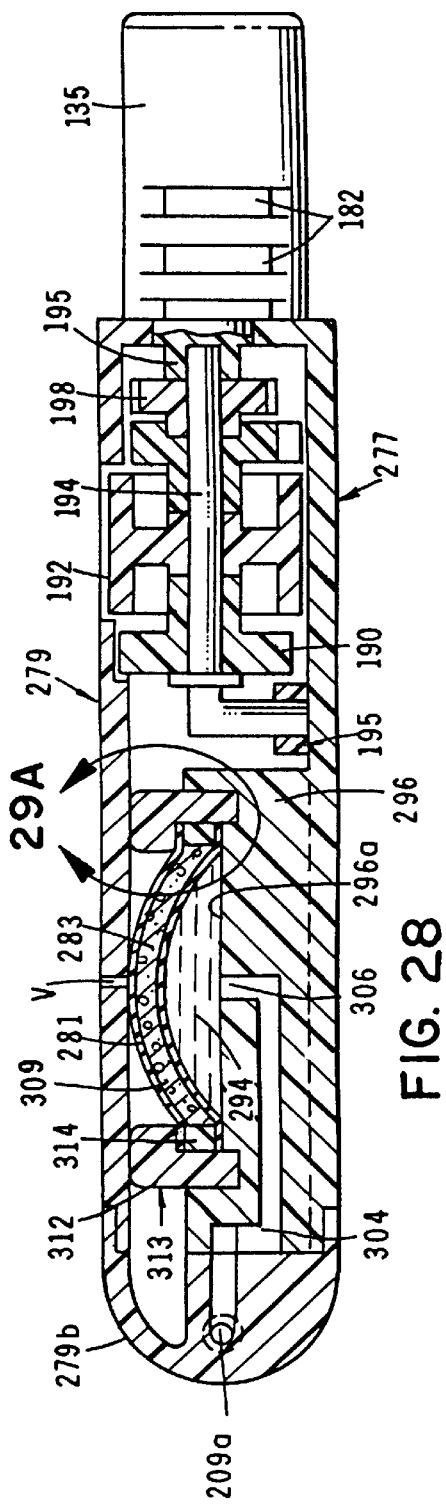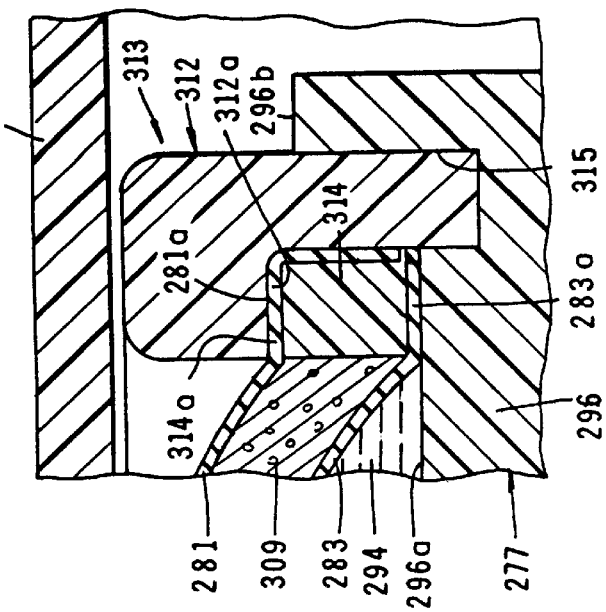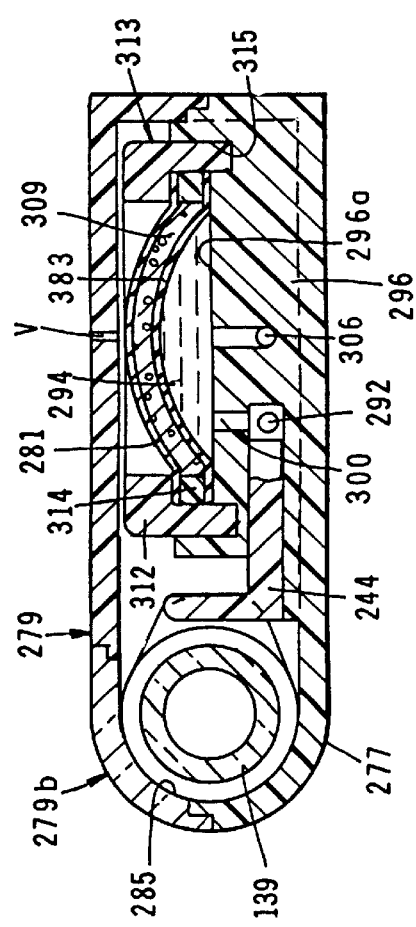

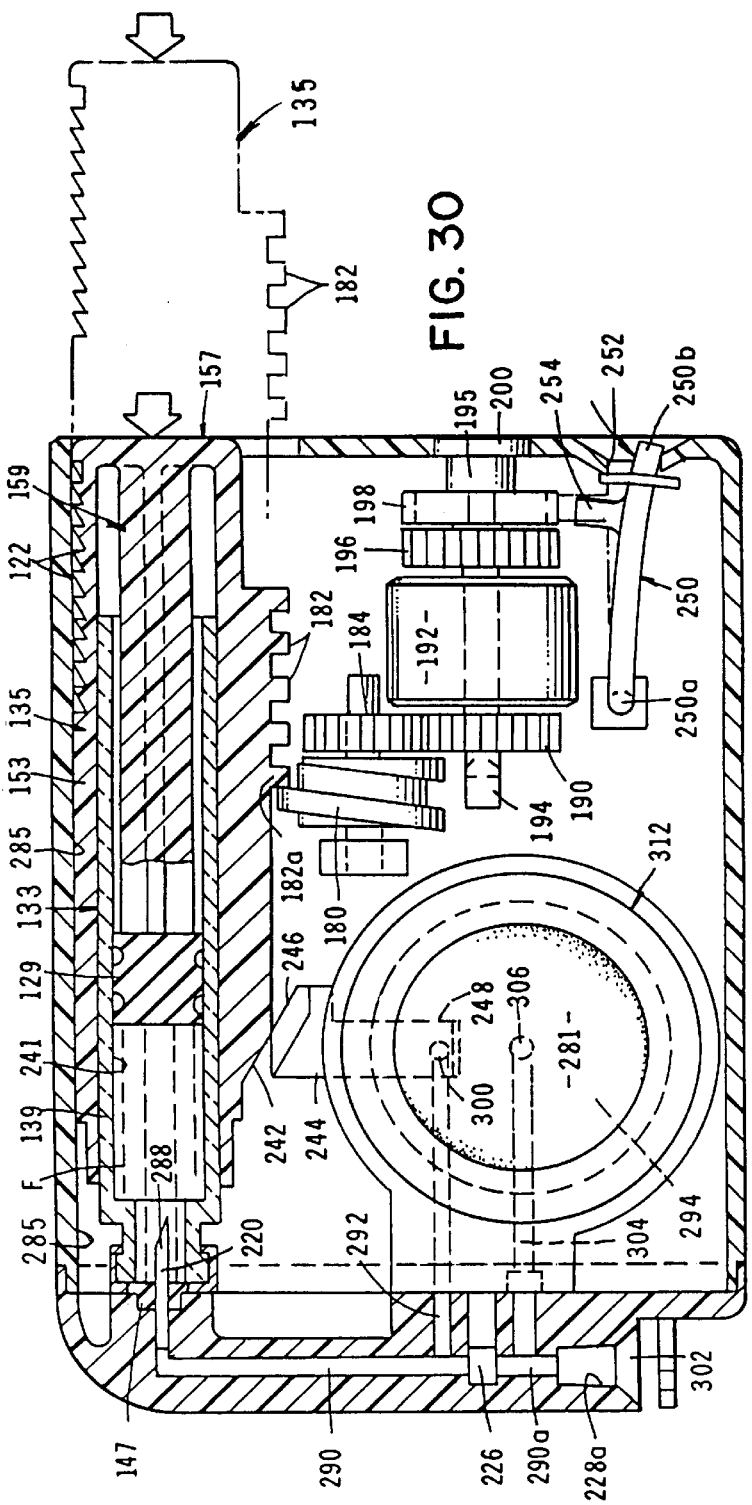
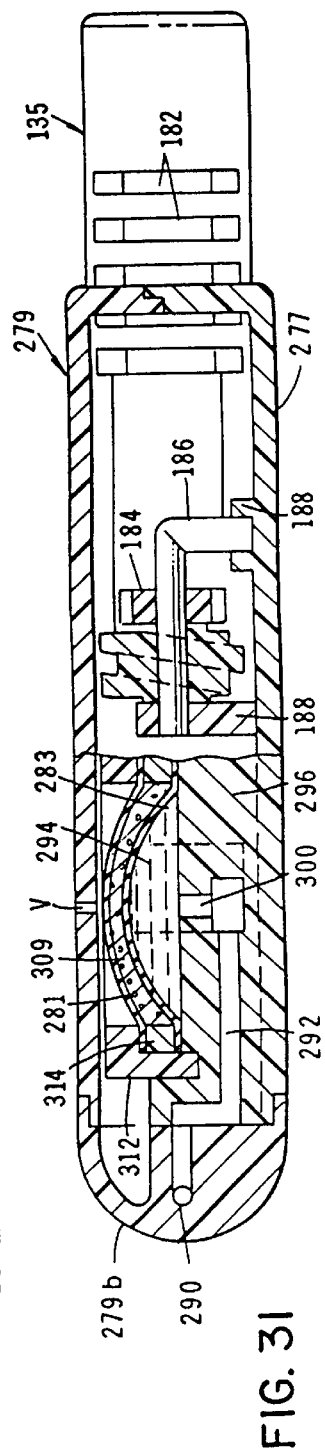
FIG. 30
FIG. 31

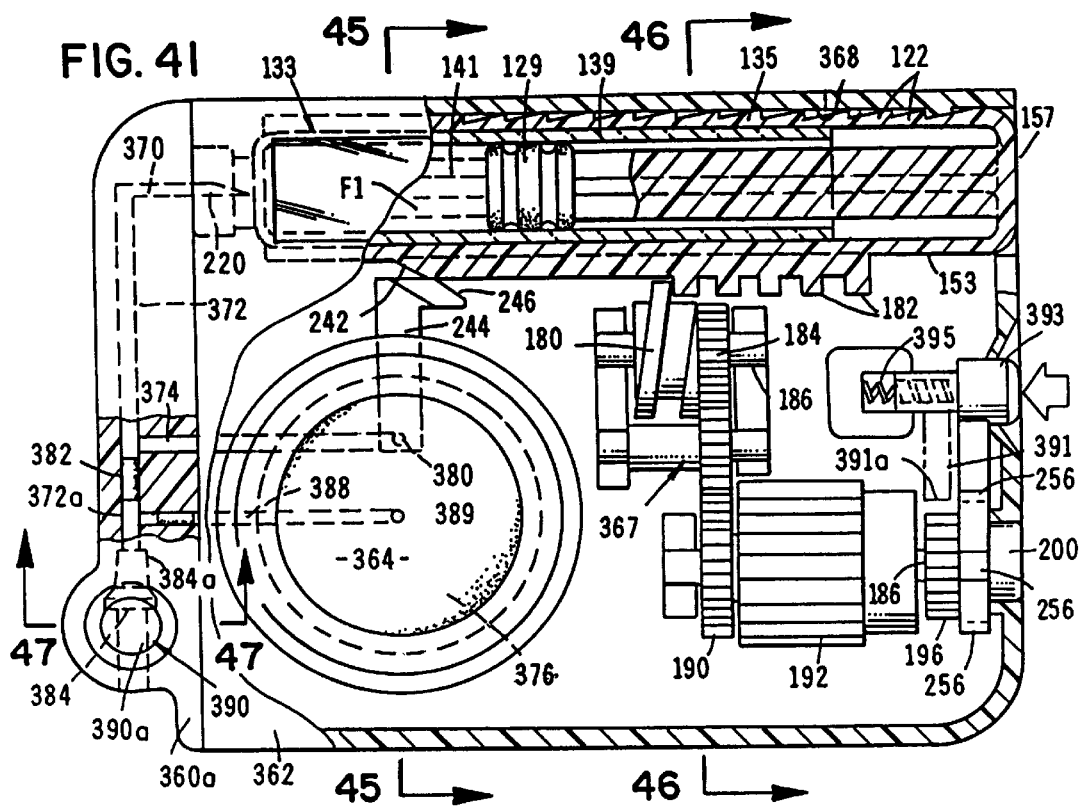
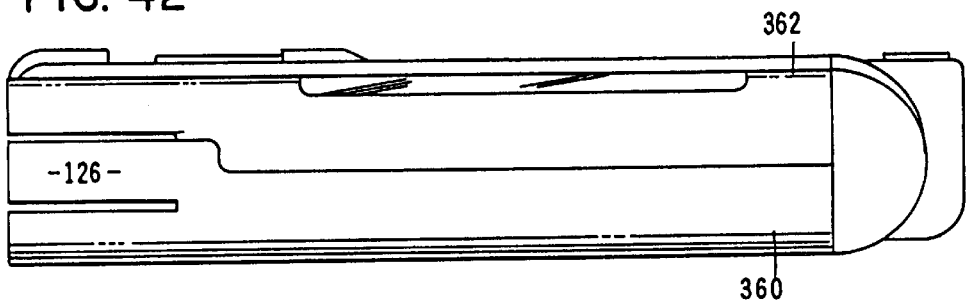
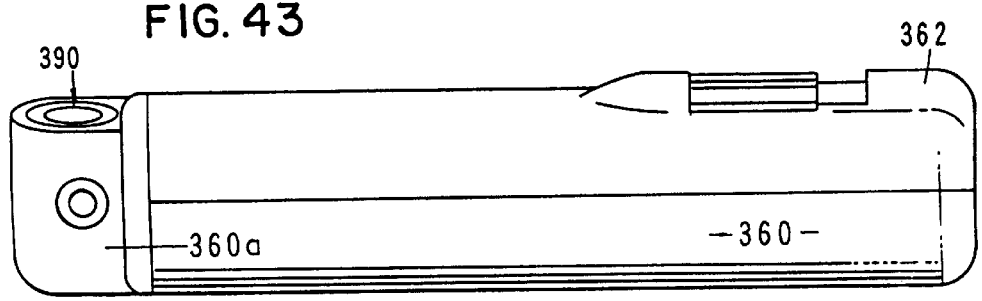

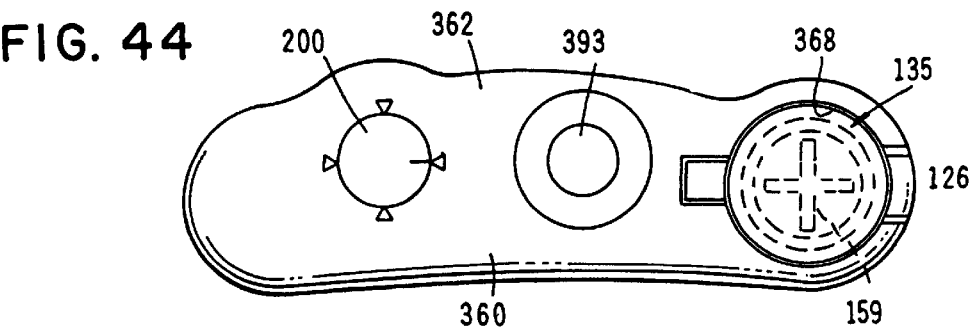
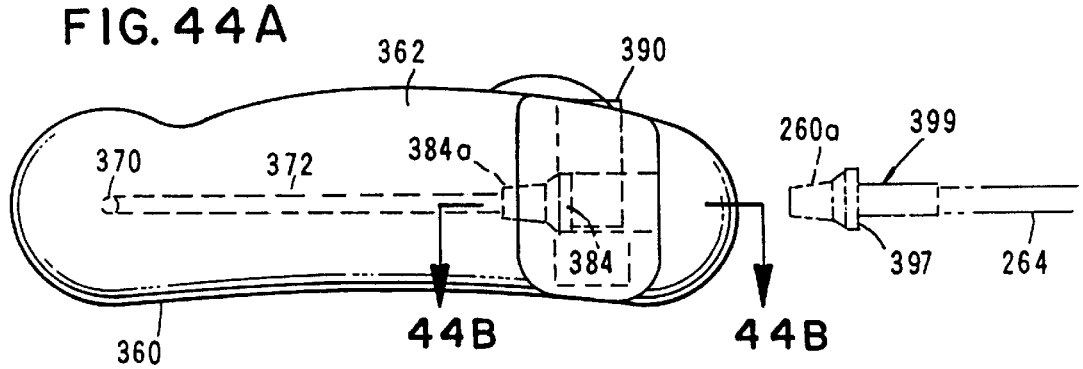
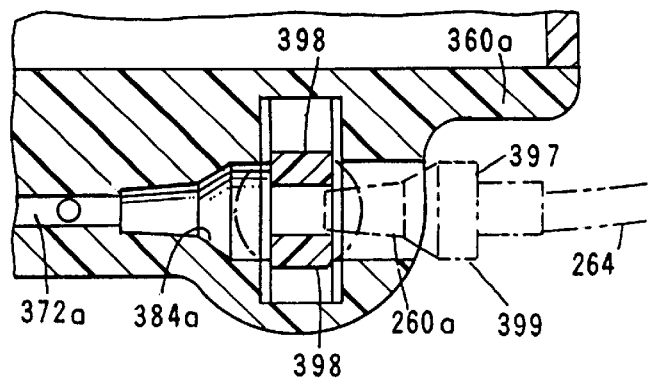

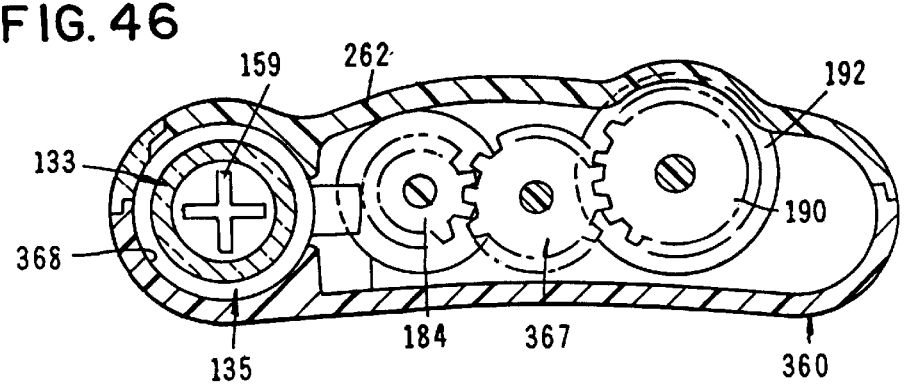
FIG. 46
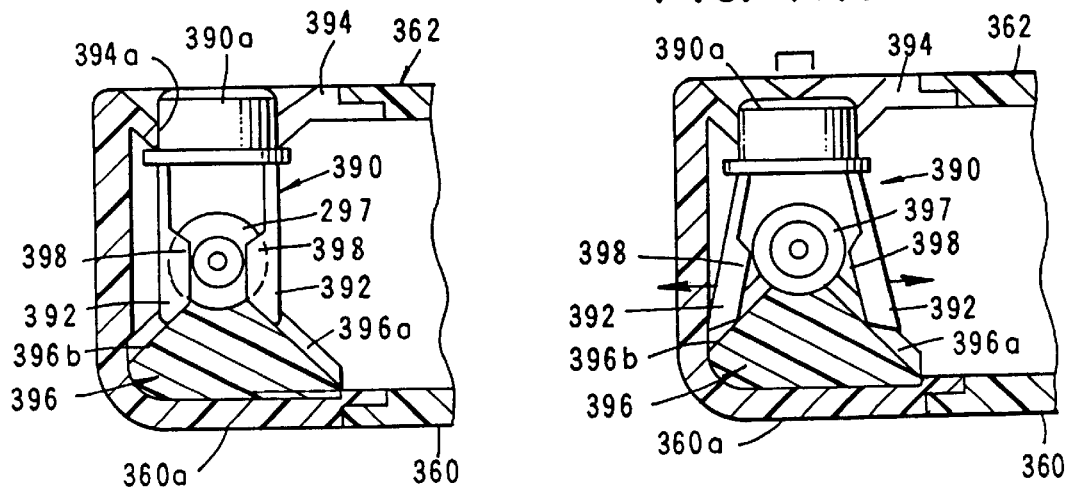
FIG. 47A
FIG. 47
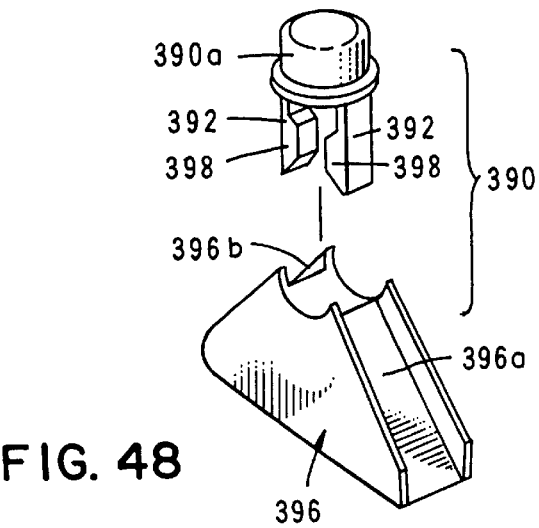
FIG. 48

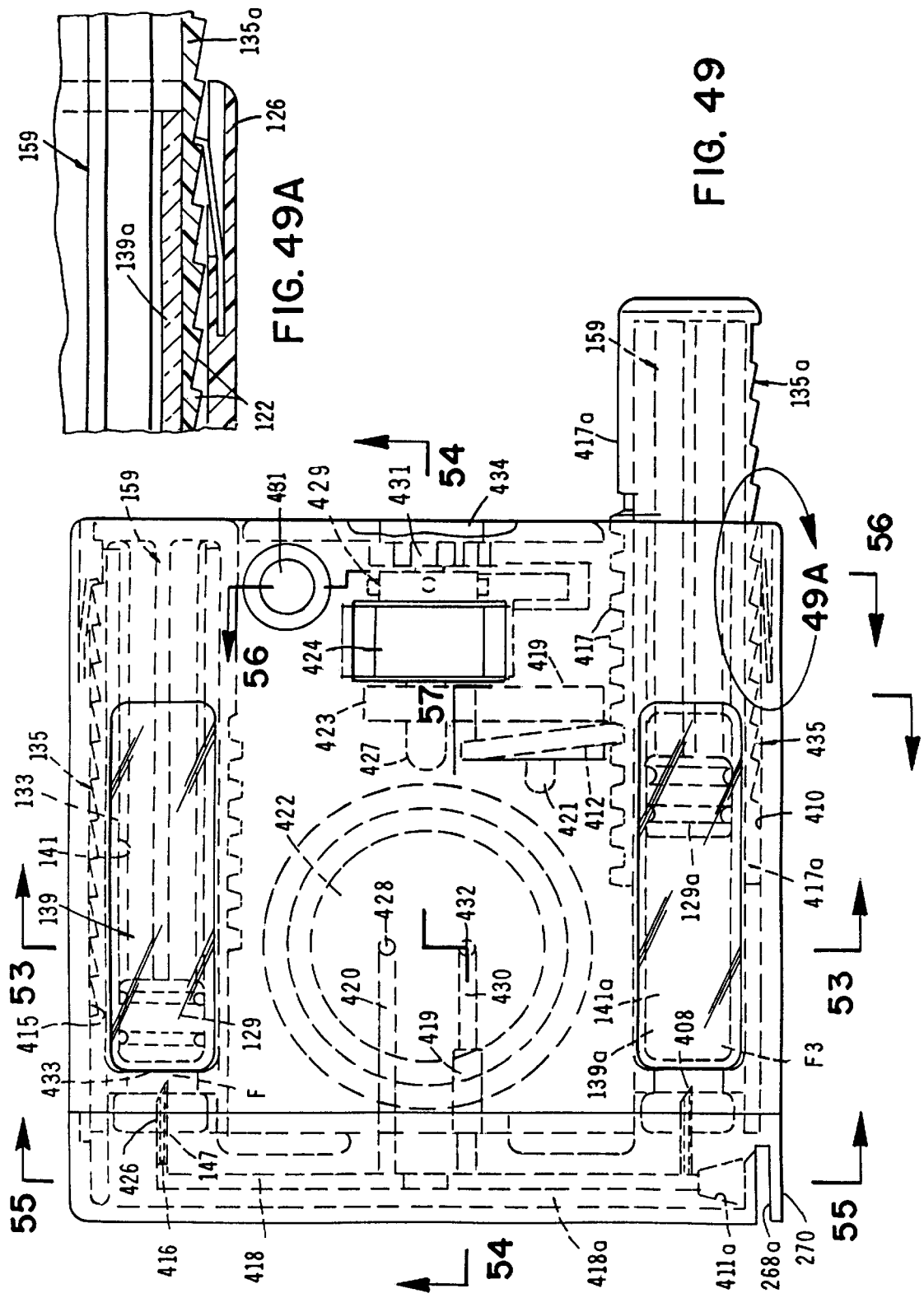

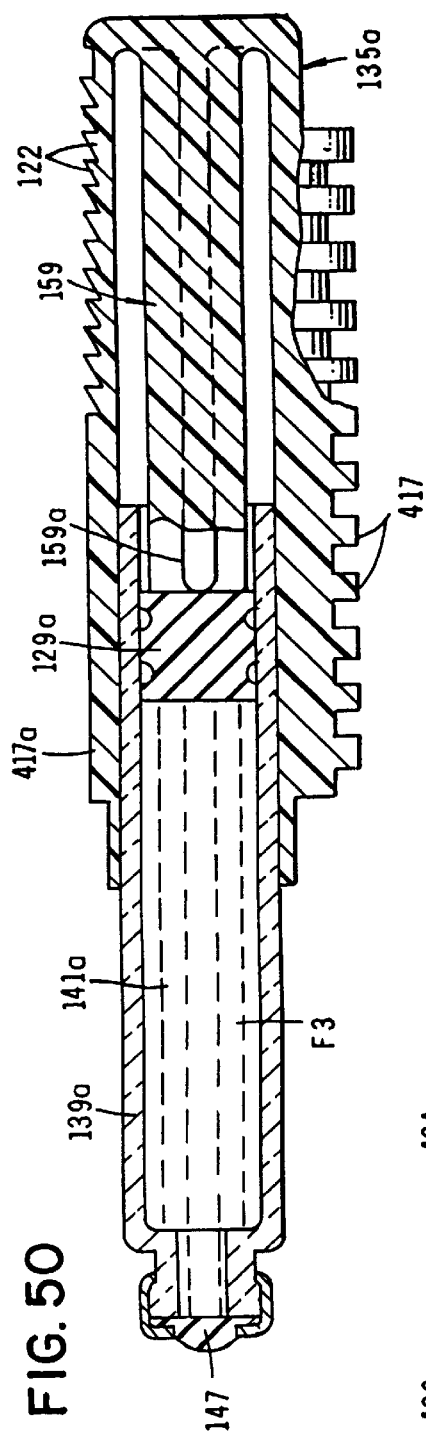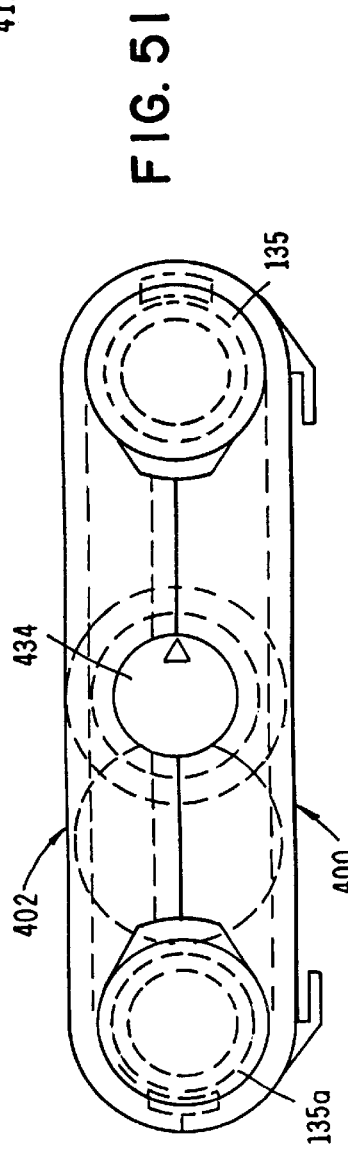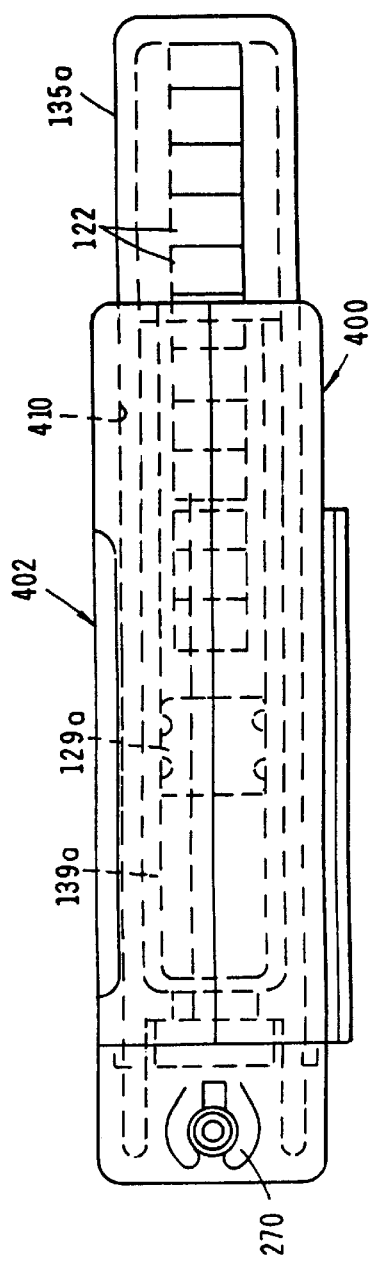

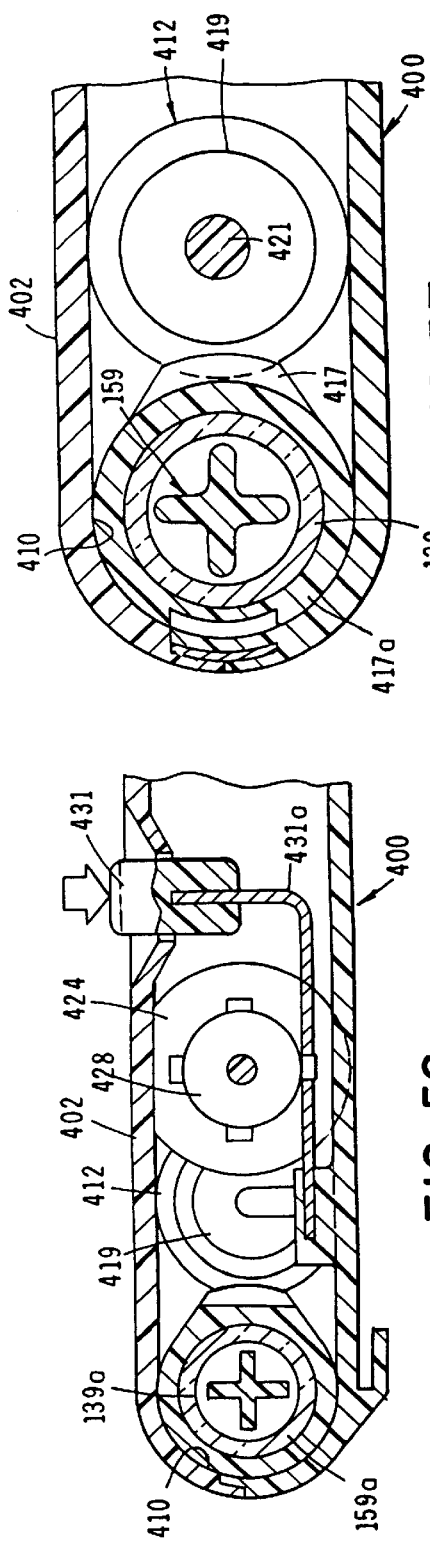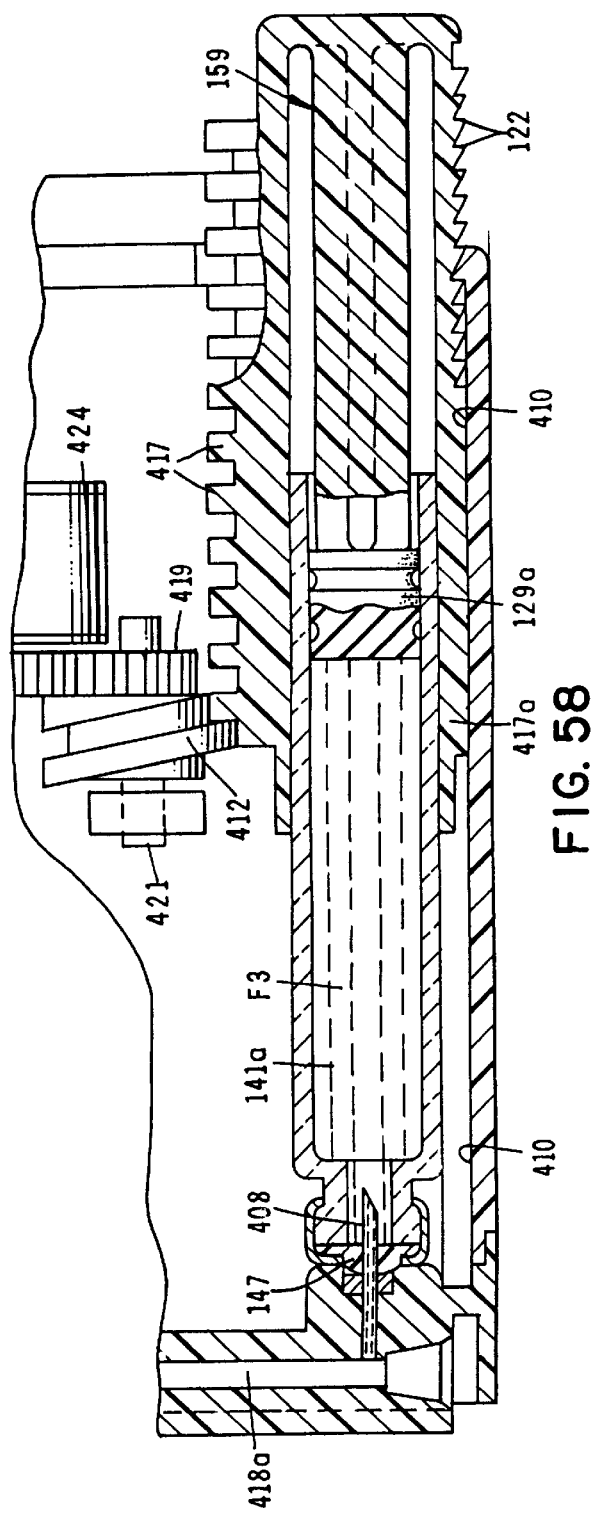

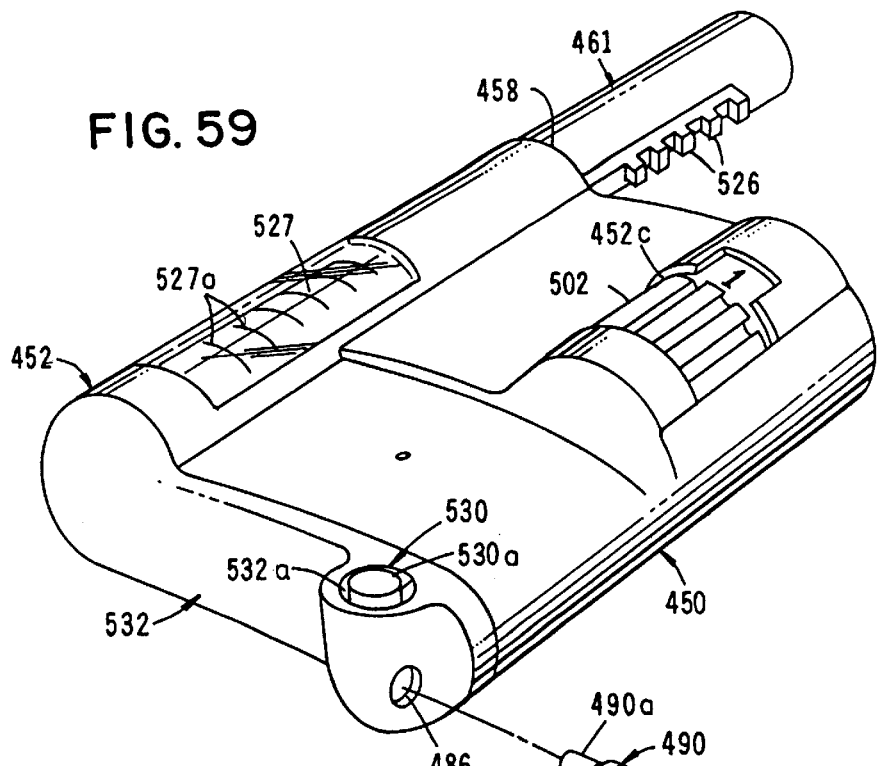
FIG. 59
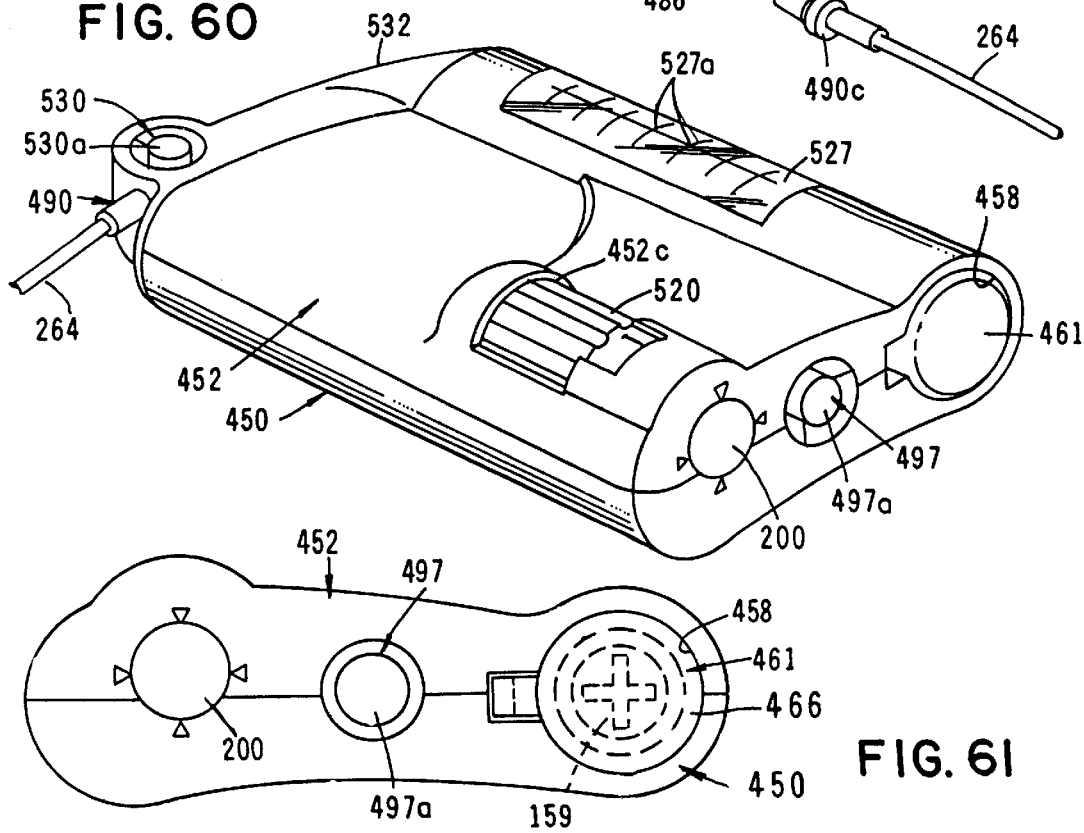
FIG. 60
FIG. 61

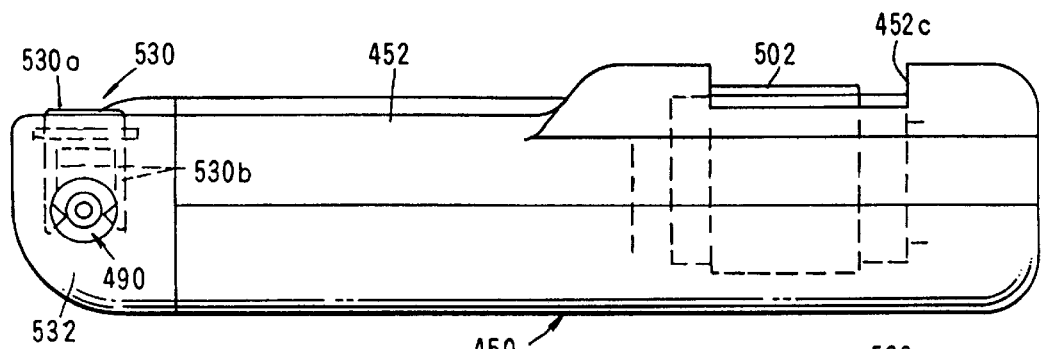
FIG. 62
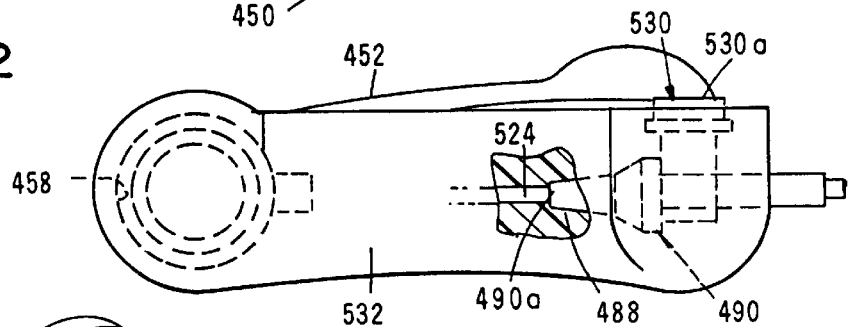
FIG. 63
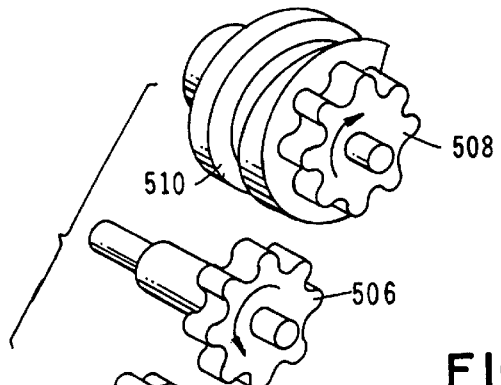
FIG. 65
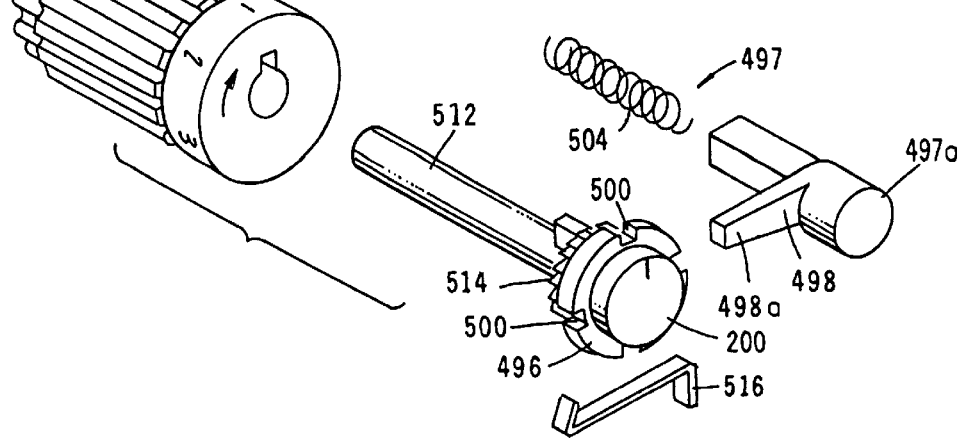

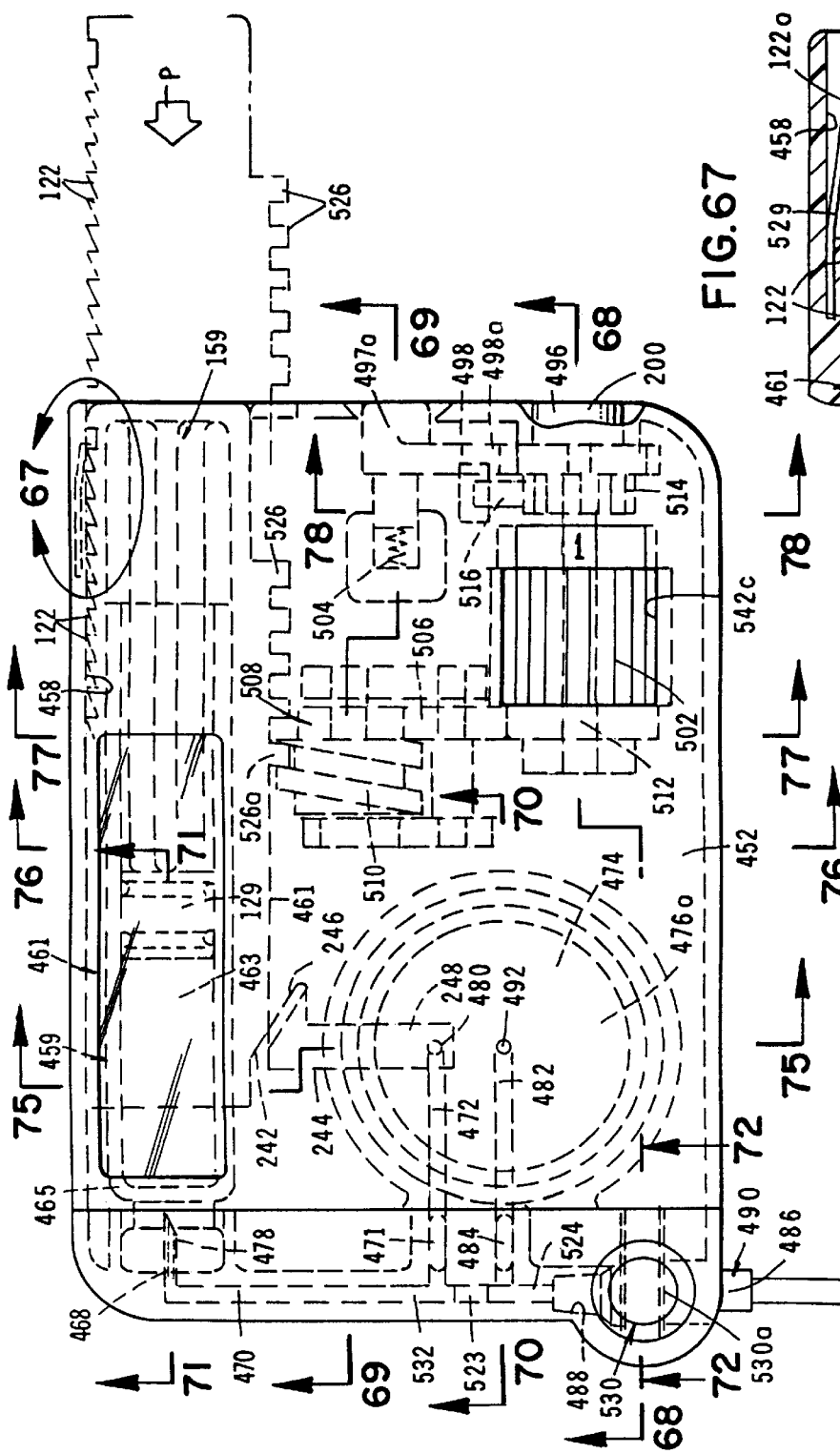
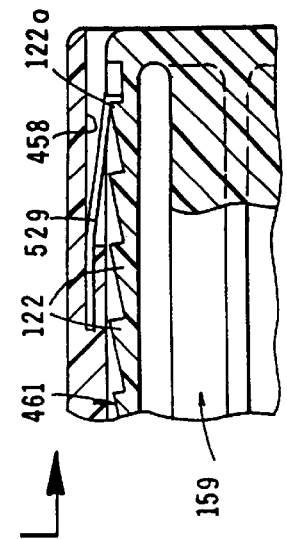
FIG. 66
FIG. 67

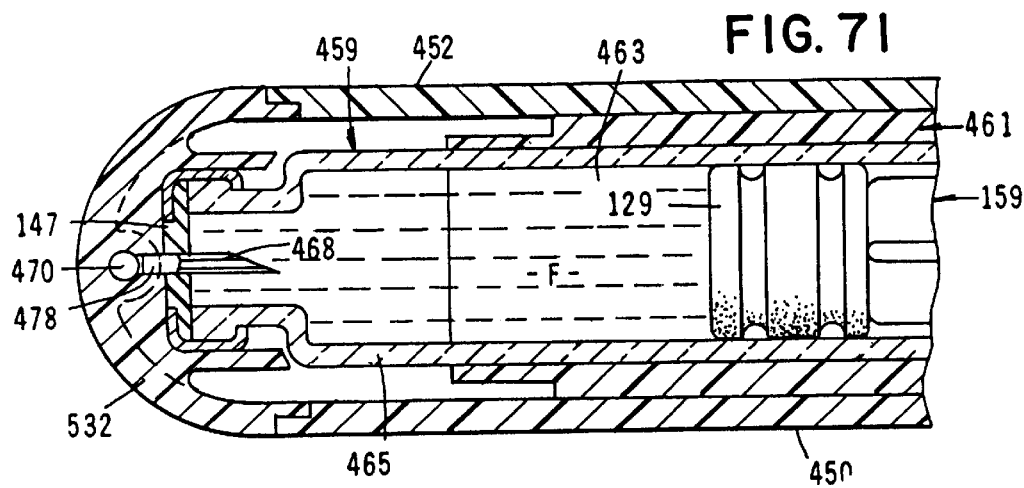
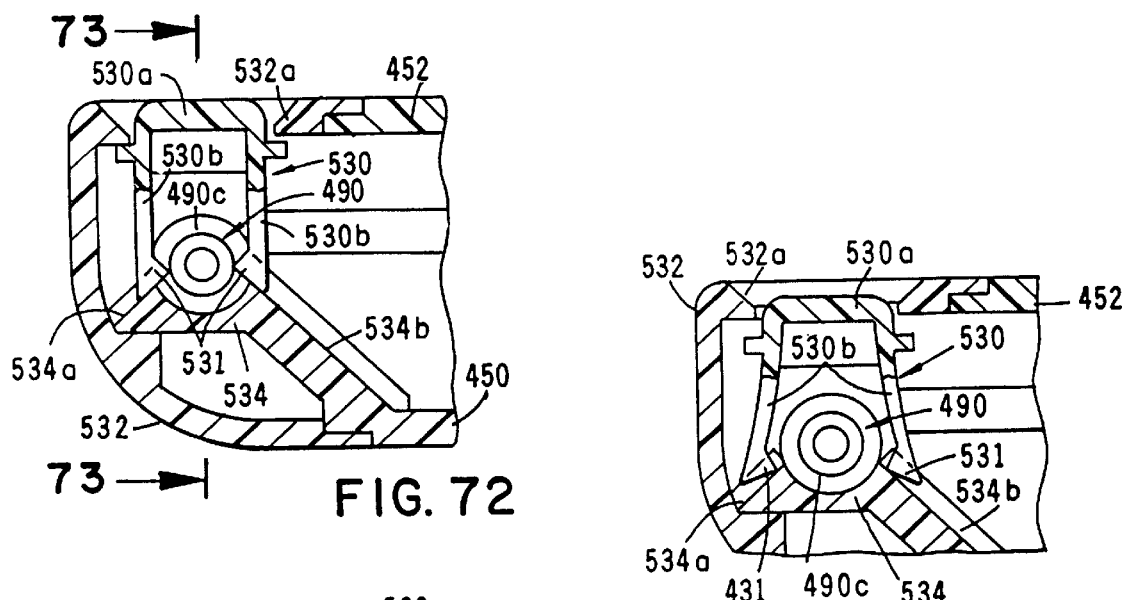
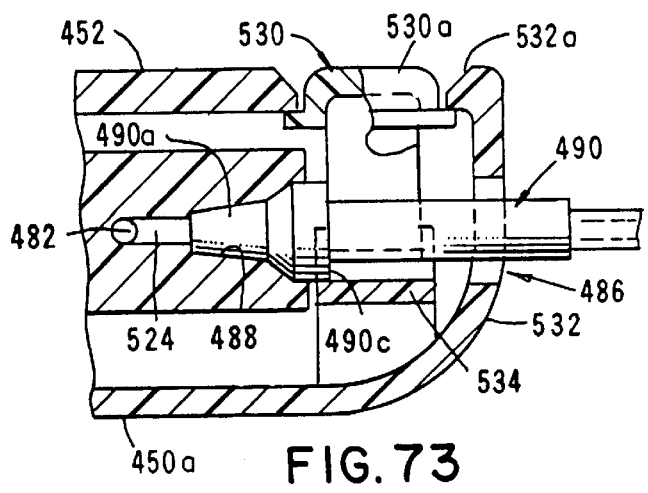

FLUID DELIVERY DEVICE WITH CONFORMABLE ULLAGE AND FILL ASSEMBLY

This is a Divisional application of U.S. application, Ser. No. 08/666,659, filed Jun. 18, 1996, U.S. Pat. No. 5,830,187; which is Continuation-In-Part of U.S. application, Ser. No. 08/577,779, filed Dec. 22, 1995, now issued into U.S. Pat. No. 5,807,335.

BACKGROUND OF THE INVENTION

1. Field of the Invention

The present invention relates generally to fluid delivery devices for infusion of beneficial agents into a patient. More particularly, the invention concerns a fluid delivery apparatus which includes a conformable ullage and a novel fill assembly for filling the fluid reservoir of the apparatus in the field.

2. Discussion of the Invention

Many medicinal agents require an intravenous route for administration thus by passing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished by gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

One of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly. The ullage in these devices, that is the amount of the fluid reservoir or chamber that is not filled by fluid, is provided in the form of a semi-rigid structure having flow channels leading from the top of the structure through the base to inlet or outlet ports of the device. Since the inventions described herein represent improvements over those described in U.S. Pat. No. 5,205,820 this patent is hereby incorporated by reference as though fully set forth herein.

In the semi-rigid ullage configuration described in U.S. Pat. No. 5,205,820, wherein the ullage means is more fully described, the stored energy means of the device must be superimposed over the ullage to form the fluid containing portion of the reservoir from which fluids are expelled at a controlled rate by the elastomeric membrane of the stored energy means tending to return to a less distended configuration in the direction toward the ullage. With these constructions, the stored energy membrane is typically used at higher extensions over a significantly large portion of the pressure-deformation curve.

For good performance, the elastomeric membrane materials selected for construction of the stored energy membrane must have good memory characteristics under conditions of high extension; good resistance to chemical and radiological degradation; and appropriate gas permeation characteristics depending upon the end application to be made of the device. Once an elastomeric membrane material is chosen that will optimally meet the desired performance requirements, there still remain certain limitations to the level of refinement of the delivery tolerances that can be achieved using the semi-rigid ullage configuration. These result primarily from the inability of the semi-rigid ullage to conform to the shape of the elastomeric membrane near the end of the delivery period. This nonconformity can lead to extended delivery rate tail-off and higher residual problems when extremely accurate delivery is required. For example, when larger volumes of fluid are to be delivered, the tail-off volume represents a smaller portion of the fluid amount delivered and therefore exhibits much less effect on the total fluid delivery profile, but in very small doses, the tail-off volume becomes a larger portion of the total volume. This sometimes places severe physical limits on the range of delivery profiles that may easily be accommodated using the semi-rigid ullage configuration.

As will be better appreciated from the discussion which follows, the apparatus of the present invention provides a unique, disposable fluid dispenser of simple but highly reliable construction that may be adapted to a wide variety of end use applications. A particularly important aspect of the improved apparatus is the incorporation of conformable ullages made of yieldable materials which uniquely conform to the shape of the stored energy membrane as the membrane distends and then returns to a less distended configuration. This novel construction, which permits the overall height of the device to be minimized, will satisfy even the most stringent delivery tolerance requirements and uniquely overcomes the limitation of materials selection. Further a plurality of subreservoirs can be associated with a single ullage thereby making it possible to incorporate a wide variety of delivery profiles within a single device.

The thrust of the present invention is to provide a novel fluid delivery apparatus that includes a conformable ullage of the character described in the preceding paragraph and also includes a unique fill assembly that can be used to controllably fill the fluid reservoir of the apparatus in the field. As will be better understood from the description which follows, the fill assembly of the present invention includes a fluid containing vial subassembly mounted within a unique adapter subassembly that functions to conveniently mate the vial subassembly with the conformable ullage type fluid delivery assembly.

In use, the adapter subassembly of the invention securely interconnects the fluid containing vial with the fluid delivery assembly so that the reservoir of the device can be controllably filled with the fluid contained within the vial assembly. After the reservoir is thus filled, the stored energy means of the fluid delivery device will cooperate with the conformable ullage to controllably expel the fluid from the device.

Another very important feature of the invention is the ability of the apparatus to provide, not only a closely controllable basal dose of medication, but also to periodically provide a controlled bolus dose of medication. This makes the apparatus most attractive for use with diabetics. For example, a normal individual who doesn't have diabetes requires energy throughout the day just to maintain a basal metabolic rate. This energy is supplied to the cells by glucose that is transported from the bloodstream to the cells by insulin. When food is consumed, the blood glucose level rises and the pancreas responds by releasing a surge of fast-acting insulin. To mimic this natural process with individual injections, the individual would have to administer minuscule amounts of fast-acting insulin every few minutes throughout the day and night.

Conventional therapy usually involves injecting, separately, or in combination, fast-acting and slower-acting insulin by syringe several times a day, often coinciding with meals. The dose must be calculated based on glucose levels present in the blood. Slower-acting insulin is usually administered in the morning and evening to take advantage of longer periods of lower level glucose uptake. Fast-acting insulin is usually injected prior to meals. If the dosage of fast-acting insulin is off, the bolus administered may lead to acute levels of either glucose or insulin resulting in complications, including unconsciousness or coma. Over time, high concentrations of glucose in the blood can also lead to a variety of chronic health problems, such as vision loss, kidney failure, heart disease, nerve damage, and amputations.

A recently completed study sponsored by the National Institutes of Health (NIH) investigated the effects of different therapeutic regimens on the health outcomes of insulin-dependent diabetics. This study revealed some distinct advantages in the adoption of certain therapeutic regimens. Intensive therapy that involved intensive blood glucose monitoring and more frequent administration of insulin by conventional means, for example, syringes, throughout the day saw dramatic decreases in the incidence of debilitating complications.

The NIH study also raises the question of practicality and patient adherence to an intensive therapy regimen. A bona fide improvement in insulin therapy management must focus on the facilitation of patient comfort and convenience as well as dosage and administration schemes. Basal rate delivery of insulin by means of a convenient and reliable delivery device over an extended period of time represents one means of improving insulin management. Basal rate delivery involves the delivery of very small volumes of fluid (for example, 0.3–3 mL. (depending on body mass) over comparatively long periods of time (18–24) hours). As will be appreciated from the discussion which follows, the apparatus of the present invention is uniquely suited to provide precise basal fluid delivery management and also a closely controlled bolus delivery of medication on an as-needed basis. For example, if the apparatus is being used for basal delivery of insulin over an extended period of time, should a bolus delivery of medication be required to manage an anticipated increase in blood sugar, such a bolus delivery can be quickly and easily accomplished using the bolus injection means of the invention, thereby eliminating the need for a direct subdermal injection at an alternate site on the individual's body.

SUMMARY OF THE INVENTION

It is an object of the present invention to provide a fluid delivery apparatus which embodies a stored energy source such as a distendable elastomeric membrane which cooperates with a base and a conformable ullage to define a fluid reservoir and one which includes a unique fill assembly for use in controllably filling the fluid reservoir. The novel fill assembly of the invention enables the fluid reservoir of the fluid delivery portion of the apparatus to be aseptically filled in the field with a wide variety of selected medicinal fluids.

Another object of the present invention is to provide an apparatus of the aforementioned character in which the fill assembly comprises a vial assembly of generally conventional construction that can be prefilled with a wide variety of medicinal fluids.

Another object of the present invention is to provide a fill assembly of the type described in the preceding paragraph in which the prefilled vial subassembly is partially received within a novel adapter subassembly that functions to operably couple the vial subassembly with the fluid delivery portion of the apparatus.

Another object of the invention is to provide viewing means for viewing the amount of fluid remaining within the prefilled vial as the fluid reservoir is being filled.

Another object of the invention is to provide an adapter subassembly of the type described in which the body of the prefilled vial is surrounded by a protective covering to maintain the vial in an aseptic condition until immediately prior to mating the subassembly with the fluid delivery portion of the apparatus.

Another object of the invention is to provide an apparatus as described in the preceding paragraphs in which the adapter subassembly includes locking means for locking the subassembly to the fluid delivery portion of the apparatus following filling of the fluid reservoir thereof.

Another object of the invention is to provide a novel fill assembly which is easy to use, is inexpensive to manufacture, and one which maintains the prefilled vial in aseptic condition until time of use.

Another object of the invention is to provide an apparatus of the character described in the preceding paragraphs which embodies a soft, pliable, conformable mass which defines an ullage within the reservoir of the device which will closely conform to the shape of the stored energy membrane geometry thereby providing a more linear delivery and effectively avoiding extended flow delivery rate tail-off with minimum residual fluid remaining in the reservoir at end of the fluid delivery period.

Another object of the invention is to provide an apparatus of the character described which includes novel fluid rate control means for precisely controlling the rate of fluid flow from the device.

Another object of the invention is to provide an apparatus which, due to its unique construction, can be manufactured inexpensively in large volume by automated machinery.

Another object of the present invention is to provide a fill assembly of the type described in which the adapter subassembly includes a plurality of outwardly extending teeth which are engageable by a manually operated drive wheel that is rotatably mounted in the fluid delivery portion of the apparatus so that the adapter subassembly and the vial subassembly can be controllably advanced into a receiving chamber provided in the fluid delivery portion of the apparatus.

Another object of the invention is to provide an apparatus of the character described in the preceding paragraph which is specially designed to permit in addition to the infusion of a basal dose the infusion of a bolus dose of medication.

Other objects of the invention are set forth in U.S. Pat. No. 5,205,820 which is incorporated herein by reference and still further objects will become apparent from the discussion which follows.

BRIEF DESCRIPTION OF THE DRAWINGS

FIG. 3 is a cross-sectional view taken along lines 3—3 of FIG. 2.

FIG. 4 is a cross-sectional view taken along lines 4—4 of FIG. 2.

FIG. 7 is a generally perspective view of one form of the adapter assembly of the present invention.

FIG. 8 is an enlarged, cross-sectional view of the adapter assembly illustrated in FIG. 7 as it appears in an assembled configuration.

FIG. 9 is a cross-sectional view similar to FIG. 8, but showing the appearance of the component parts of the invention after the plunger of the container has been telescopically moved from a first to a second position.

FIG. 10 is a cross-sectional view taken along lines 10—10 of FIG. 8.

FIG. 11 is a generally perspective exploded view of an alternate form of fill assembly of the present invention usable in providing a bolus dose of medication to a patient.

FIG. 12 is an enlarged, cross-sectional view of the fill assembly illustrated in FIG. 11 as it appears in an assembled configuration.

FIG. 13 is a cross-sectional view taken along lines 13—13 of FIG. 12.

FIG. 14 is a top plan view, partly broken away to show internal construction of an alternate form of the fluid delivery portion of the apparatus of the invention to which the fluid containing portion of the assembly shown in FIG. 12 has been operably connected.

FIG. 14A is an end view of the apparatus shown in FIG. 14.

FIG. 14B is a side view of the apparatus shown in FIG. 14.

FIG. 15 is a cross-sectional view taken along lines 15—15 of FIG. 14.

FIG. 15A is a fragmentary, cross-sectional view of the portion designated as 15A in FIG. 15.

FIG. 18C is a fragmentary top view illustrating further advancement of the adapter assembly during the delivery of the bolus dose.

FIG. 19 is a cross-sectional view taken along lines 19—19 of FIG. 14 showing one form of locking means of the invention for controlling rotation of the driving wheel of the invention.

FIG. 20 is a cross-sectional view taken along lines 20—20 of FIG. 14.

FIG. 21 is a cross-sectional view taken along lines 21—21 of FIG. 14.

FIG. 24 is a generally perspective exploded view of another form of the apparatus of the invention.

FIG. 25 is a generally perspective exploded view of the reservoir assembly of the apparatus shown in FIG. 24.

FIG. 26 is a top plan view, partly broken away to show internal construction of another form of the fluid delivery portion of the apparatus of the invention to which the fluid containing portion of the assembly shown in FIG. 12 has been operably connected.

FIG. 27 is a side view of the apparatus shown in FIG. 26.

FIG. 28 is a cross-sectional view taken along lines 28—28 of FIG. 26.

FIG. 29 is a cross-sectional view taken along lines 29—29 of FIG. 26.

FIG. 29A is an enlarged, fragmentary, cross-sectional view of the area designated as 29A in FIG. 28.

FIG. 30 is a view similar to FIG. 26 but showing in greater detail the construction of the advancing means of the invention for controllably advancing the adapter assembly into the fluid delivery portion of the apparatus.

FIG. 31 is a cross-sectional view taken along lines 31—31 of FIG. 26.

FIG. 41 is a top plan view, partly broken away to show internal construction of still another form of the apparatus of the invention.

FIG. 42 is a side view of the apparatus shown in FIG. 41.

FIG. 43 is a view of the opposite side of the apparatus from that shown in FIG. 42.

FIG. 44 is a right-hand end view of the apparatus shown in FIG. 41.

FIG. 44A is a lift-hand end view of the apparatus shown in FIG. 41.

FIG. 44B is a cross-sectional view taken along lines 44B—44B of FIG. 44A.

FIG. 45 is a cross-sectional view taken along lines 45—45 of FIG. 41.

FIG. 46 is a cross-sectional view taken along lines 46—46 of FIG. 41.

FIG. 47 is an enlarged fragmentary, cross-sectional view taken along lines 47—47 of FIG. 41.

FIG. 47A is a fragmentary, cross-sectional view similar to FIG. 47 but showing the delivery line release means of the invention in a depressed configuration.

FIG. 48 is a generally perspective, exploded view of one form of the delivery line release means of the invention.

FIG. 49 is a top plan view, partly broken away to show internal construction of still another form of dual vial apparatus of the invention for accomplishing basil and bolus fluid delivery basil and bolus fluid delivery.

FIG. 49A is a fragmentary, cross-sectional view of the area designated as 49A in FIG. 49.

FIG. 50 is a cross-sectional view of a portion of the fill assembly of the apparatus for accomplishing bolus delivery.

FIG. 51 is a right-hand end view of the apparatus shown in FIG. 49.

FIG. 52 is a side view of the apparatus shown in FIG. 49.

FIG. 56 is a cross-sectional view taken along lines 56—56 of FIG. 49.

FIG. 57 is an enlarged, fragmentary, cross-sectional view taken along lines 57—57 of FIG. 49.

FIG. 58 is an enlarged, fragmentary, cross-sectional view of the bolus-vial portion of the apparatus shown in FIG. 49.

FIG. 59 is a generally perspective view of yet another embodiment of the invention showing the vial assembly of the apparatus in the retracted position.

FIG. 60 is a generally perspective view of the embodiment of the invention shown in FIG. 59, but with the vial assembly received within the housing and the delivery line connected to the outlet port of the housing.

FIG. 61 is an end view of the apparatus shown in FIG. 60.

FIG. 62 is a side view of the apparatus shown in FIG. 60.

FIG. 63 is a view of the opposite end of the apparatus from that shown in FIG. 61 partly broken away to show internal construction.

FIG. 65 is a generally perspective, exploded view of the operating means of this latest form of the invention.

FIG. 66 is a top plan view of the apparatus shown in FIG. 59, partly broken away to show internal construction.

FIG. 67 is a cross-sectional view of the area designated as 67 in FIG. 66.

FIG. 71 is a cross-sectional view taken along lines 71—71 of FIG. 66.

FIG. 72 is an enlarged cross-sectional view of the left-hand portion of the device shown in FIG. 68 better illustrating the push button of the assembly of the device.

FIG. 73 is a cross-sectional view taken along lines 73—73 of FIG. 72.

FIG. 74 is a cross-sectional view similar to FIG. 72, but showing the push button assembly in a depressed configuration.

DESCRIPTION OF THE INVENTION

Figure 1:
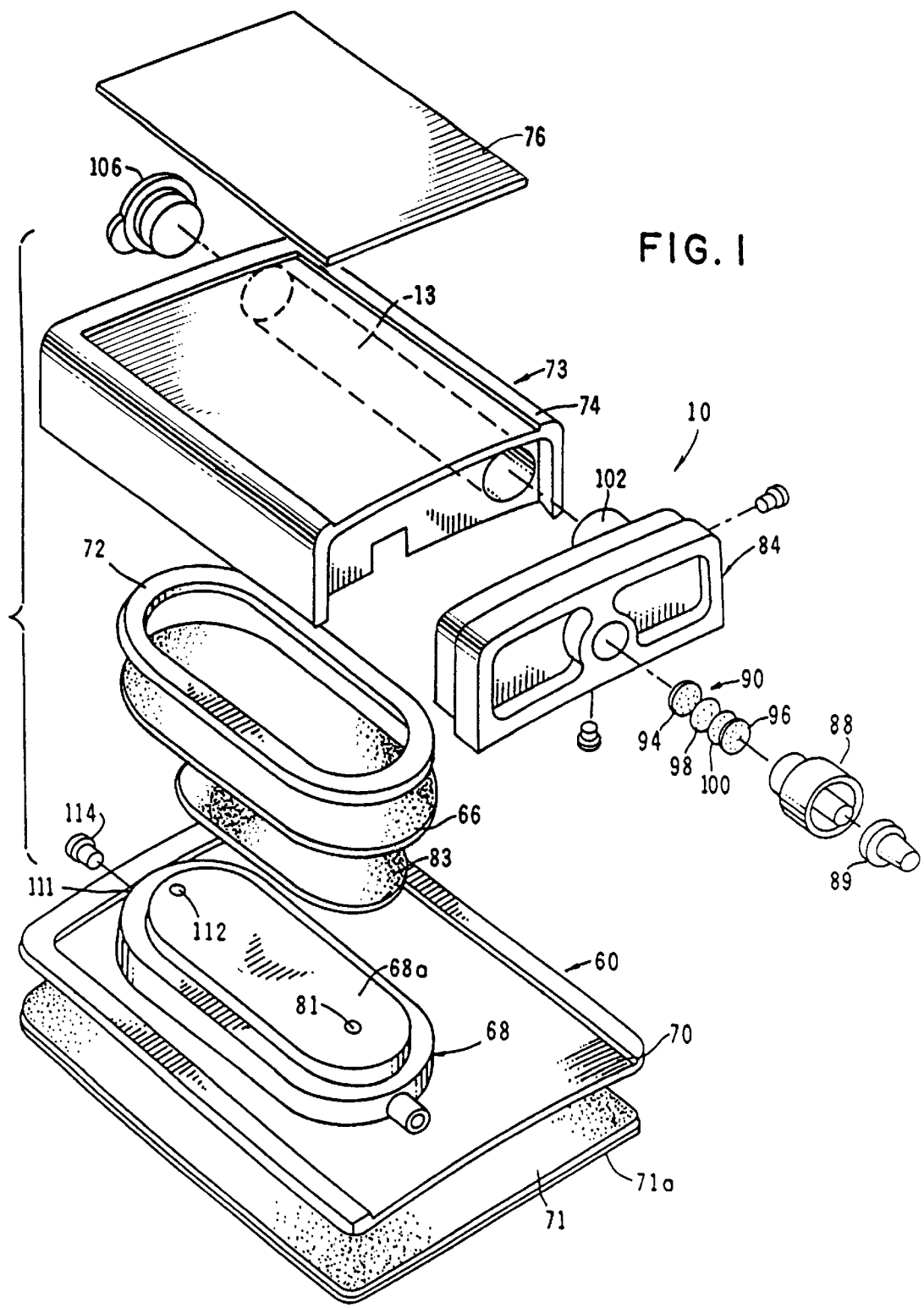
FIG. 1 is a generally perspective, exploded view of one form of the fluid delivery portion of the apparatus of the invention with which the adapter assembly of the invention can be operably interconnected.

Referring to the drawings and particularly to FIGS. 1 and 7, it is be observed that the apparatus of the invention comprises two major cooperating assemblies, namely the fluid delivery assembly 10 shown in FIG. 1 and the fill assembly 12 shown in FIG. 7. The fluid delivery assembly is similar in many respects to those disclosed in U.S. Pat. No. 5,205,820 in that it includes a base, a stored energy means which cooperates with the base to form a fluid reservoir and a cover assembly which overlays the base and encloses the stored energy means. However, unlike the fluid delivery apparatus disclosed in U.S. Pat. No. 5,205,820, which embodies semi-rigid ullages, the fluid delivery assembly of the present invention includes a novel conformable ullage, the character of which will presently be described. Also, unlike the fluid delivery devices shown in U.S. Pat. No. 5,205,820, the fluid delivery assembly of the present invention includes a uniquely configured receiving chamber 13 which is formed in the cover assembly (FIG. 1) and, in a manner presently to be described, telescopically receives a portion of the novel fill assembly of the invention.

Turning particularly to FIGS. 7 through 10, one form of the novel fill assembly portion of the apparatus is there shown and generally designated by the numeral 12. This form of the fill assembly comprises a container subassembly 14, an adapter assembly 15, and a cover assembly 17, the character of which will presently be described. Container subassembly 14 includes a body portion 16, having a fluid chamber 18 for containing an injectable fluid "F" provided with first and second open ends 20 and 22 (FIGS. 8 and 9). First open end 20 is sealably closed by closure means here provided in the form of a pierceable septum assembly 24. Septum assembly 24 is held securely in position by a clamping ring 24a. As best seen in FIGS. 8 and 9, a plunger 26 is telescopically movable within chamber 18 of container subassembly 14 from a first location shown in FIG. 8 where it is proximate first open end 22 to a second position shown in FIG. 9 where it is proximate first open end 20. The vial portion of the container subassembly 14 can be constructed of various materials such as glass and plastic.

Referring particularly to FIG. 7, it can be seen that the adapter subassembly 15 comprises a hollow housing 30 having a first open end 32 and a second closed end 34 (FIG. 9). Container subassembly 14 is telescopically receivable within open end 32 of housing 30 in the manner shown in FIG. 8 so that the housing can be moved from the first extended position shown in FIG. 8 to the second vial encapsulation position shown in FIG. 9. Forming an important part of the adapter subassembly is pusher means shown here as an elongated pusher rod 36 which functions to move plunger 26 within fluid chamber 18 from the first position shown in FIG. 8 to the second position shown in FIG. 9. In the form of the invention shown in the drawings, pusher rod 36 has a first end 36a interconnected with closure wall 34 and an opposite end 36b which engages plunger 26 and causes telescopic movement of the plunger within chamber 18 of container subassembly 14 as housing 30 is moved from the extended position into the vial encapsulating position shown in FIG. 9.

As best seen by referring to FIG. 10, the interior wall 31 of housing 30 is provided with circumferentially spaced-apart protuberances 40 which engage and center container subassembly 14 within housing 30. Due to the small surface area presented by protuberances 40, there is little frictional resistance to the sliding movement of container subassembly 14 relative to housing 30 as the housing is moved from the extended position shown in FIG. 8 into the vial encapsulating position shown in FIG. 9.

Cover subassembly 17 of the fill assembly of the present form of the invention includes a spiral wound, frangible portion 42 having a first open end 44 for telescopically receiving body portion 16 of container subassembly 14 (FIG. 8) and a second closed end 46. Portion 42 initially circumscribes a major portion of container subassembly 14 in the manner best seen in FIG. 8. An integral pull tab 42a is provided to permit the spiral wound, frangible portion to be pulled from container subassembly 14 so as to expose a substantial portion of body 16. As best seen in FIG. 7, a medicament label 50 circumscribes spiral wound portion 42 and serves to prevent accidental unwinding of the spiral portion from the container subassembly 14. However, upon pulling tab 42a, the spiral portion will unwind and, in so doing, will tear medicament label 50 so that the spiral portion 42 of the covering as well as a cylindrical portion 52 which, also comprises a part of the cover assembly, can be slipped from the container 14 so as to expose to view septum assembly 24.

As shown in FIGS. 7 and 8, the apertured end 52a of cylindrical portion 52 of subassembly 17 is provided with venting apertures 54 which are covered by a porous vent patch 56 which can be constructed from any suitable porous material that will permit air entrapped within the interior of cover subassembly 17 to be expelled to atmosphere as the subassembly is placed over container subassembly 14.

Turning once again to FIGS. 1 through 6, the fluid delivery assembly portion 10 of the apparatus can be seen to include a base subassembly 60, a cover subassembly 73 receivable over base subassembly 60, and a stored energy means, here provided in the form of a distendable membrane 66 (FIGS. 3 and 4). As best seen in FIGS. 3 and 4 the periphery of membrane 66 is sealably connected to an upraised portion 68 formed on base member 70. Base member 70 forms a part of base assembly 60 as does a clamping ring 72 which functions to clamp membrane 66 to upraised portion 68 (FIG. 1). Affixed to member 70 is a thin, planar shaped foam pad 71 having an adhesive coating provided on both its upper and lower surfaces. The adhesive coating on the upper surface of the pad enables the pad to be affixed to the lower surface of base member 70. As indicated in FIGS. 3 and 4, a peel strip 71a is connected to the bottom surface of foam pad 71 by the adhesive coating provided thereon. when the device is to be used, peel strip 71a can be stripped away from the pad so that the adhesive on the lower surface thereof can be used to releasably affix the apparatus of the invention to the patient's body.

Turning particularly to FIGS. 1 and 3, it can be seen that the cover subassembly 73 includes a cover member 74 and a medicament label 76. Cover member 73 is provided with the previously identified elongated receiving chamber 13 which is adapted to receive a portion of the fill subassembly of the invention. In a manner presently to be described the fluid container portion of the fill subassembly communicates via passageways 78, 80 and 81 with a fluid reservoir 82 which is uniquely formed between a deformable barrier member 83 and the upper surface 68a of upraised portion 68 of base member 70 (FIGS. 3 and 4). Disposed between barrier member 83 and distendable membrane 66 is the important conformable ullage means of the invention, the unique nature of which will presently be discussed.

Figure 2:
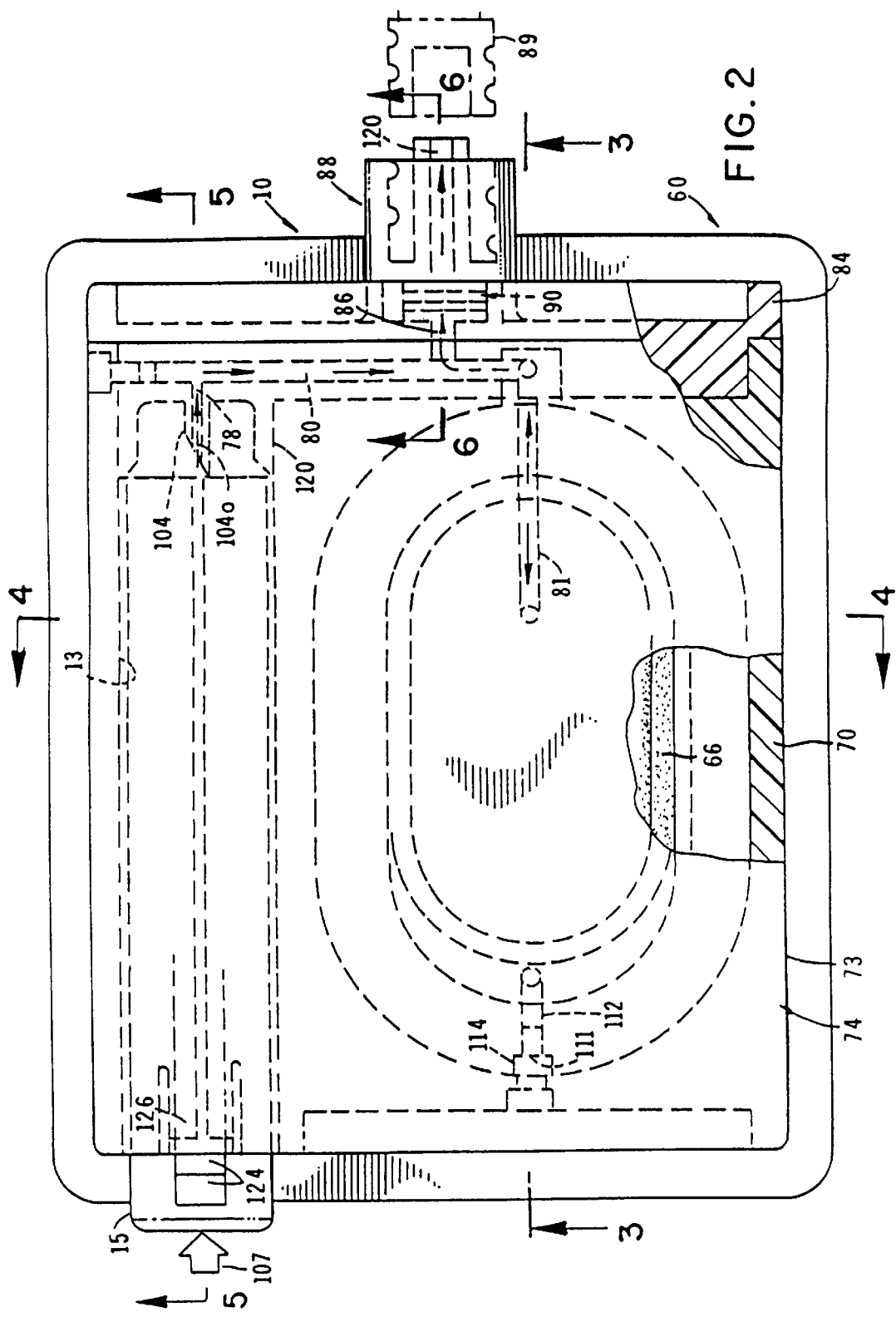
FIG. 2 is a plan view of the fluid delivery portion shown in FIG. 1, partly broken away to show internal construction and shown coupled with the fill assembly of the apparatus.
Figure 6:
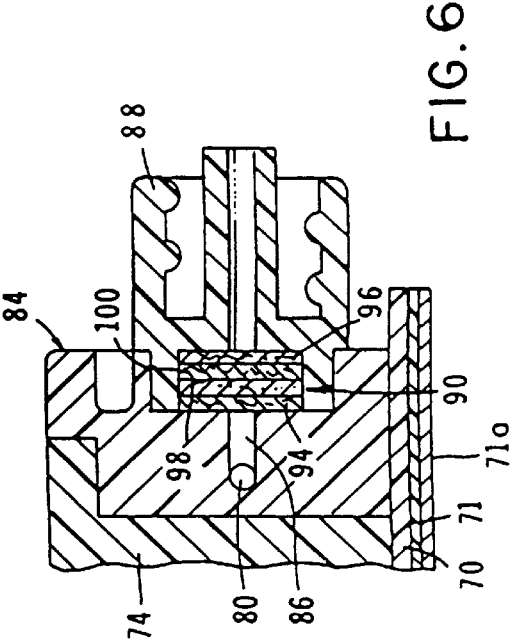
FIG. 6 is a cross-sectional view taken along lines 6—6 of FIG. 2.

Passageways 78 and 80 are formed within a housing 84 which is connected to cover member 73, while passageway 81 is formed within upraised portion 68 of base member 70. Housing 84 comprises a part of the cover subassembly of the invention and includes an outlet passageway 86 which communicates with a luer assembly 88 via flow control means generally designated by the numeral 90 (FIGS. 2 and 3). Plugs 85 and 87 seal access ports to the fluid passageways formed internally of housing 84, the purpose of which will presently be described. As best seen in FIG. 6, the flow control means here comprises an assemblage make up of four disc-like wafers. Wafers 94 and 96 of the assemblage comprise porous glass distribution frits while intermediate wafers 98 and 100 comprise a filter member and a rate control member respectively.

While filter member 98 can be constructed from a wide variety of materials, a material comprising polysulfone sold by Gelman Sciences under the name and style of SUPOR has proven satisfactory. Rate control member 100 is preferably constructed from a porous material such as polycarbonate material having extremely small flow apertures ablatively drilled by an excimer laser ablation process. Both the orifice size and unit distribution can be closely controlled by this process. However, a number of other materials can also be used to construct this permeable member, including metals, ceramics, cermet, plastics and glass. The rate control member can be specifically tailored to accommodate very specific delivery regimens including very low flow and intermediate flow conditions.

Figure 5:
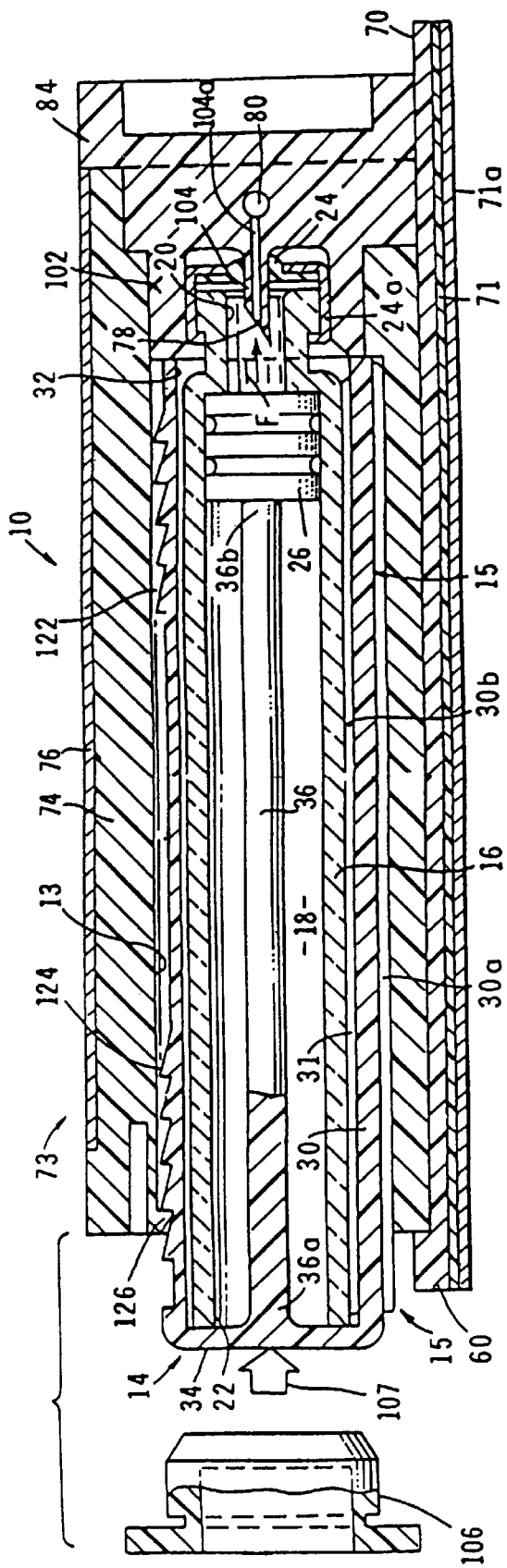
FIG. 5 is a cross-sectional view taken along lines 5—5 of FIG. 2.

As best seen in FIGS. 2 and 5, housing 84 includes a generally cylindrically shaped hollow hub-like portion 102 which extends into receiving channel 13 when the housing 84 is mated with cover member 74. Formed within hub-like portion 102 is a hollow piercing cannula 104 the purpose of which will presently be described. As indicated in FIG. 2, the internal bore 104a of hollow cannula 104 comprises the previously identified fluid passageway 78, which is in fluid communication with flow passageway 80 of housing 84.

In using the apparatus of the invention, with the fill assembly in the filled configuration shown in FIG. 8, the cover subassembly is first removed from the container subassembly by pulling on pull-tab 42a. This will cause the spiral portion 42 of the cover subassembly to tear away from the container subassembly so that it can be separated from the forwardly disposed portion 52. Once the spiral wound portion 42 is removed, cylindrical portion 52 can also be removed and discarded. Removal of the cover subassembly exposes the forward portion of the container subassembly and septum 24 readies fluid containing subassembly, which comprises the adapter subassembly and the container subassembly, for interconnection with the fluid delivery assembly.

Prior to mating the adapter subassembly of the fluid containing subassembly with the fluid delivery assembly, closure plug 106 of the cover subassembly must be removed in the manner illustrated in FIG. 1. This done, the fill assembly can be telescopically inserted into receiving chamber 13 and pushed forwardly in the direction indicated by the arrow 107 in FIG. 5. A force exerted in the direction of the arrow will cause the adapter subassembly to move to the right as viewed in FIG. 5 and will cause the piercing cannula 104 to pierce septum 24. Once a fluid flow path between fluid chamber 18 of the container subassembly 16 and the fluid reservoir 82 of the fluid delivery assembly is thus created, a continued movement of the adapter subassembly will cause pusher rod 36 to move plunger 26 forwardly of chamber 18 to a position shown in FIG. 5. As plunger 26 is moved forwardly of chamber 18, the fluid "F" contained within the chamber will flow through open end 20, into passageway 104a of the piercing cannula, passageway 80 of housing 84 and then into fluid reservoir 82 via passageway 81. As the fluid under pressure flows into reservoir 82, barrier member 83 will be distended outwardly in the manner shown in FIG. 4 and will uniformly deform the conformable ullage 77 and at the same time distend the distendable membrane 66 until it reaches the position shown in FIG. 4 where it engages inner wall 74a of cover member 74. Gases contained in the volume between wall 74a and the distendable membrane 66 will be vented to atmosphere via vent passageway "V" (FIG. 3). Ring 72, which is in clamping engagement with upstanding portion 68 of base 70 functions to capture and seal the distendable membrane against portion 68. In a similar manner, the periphery of the barrier member 83 is sealably affixed to the upstanding portion 68a of base 70 as by adhesive or thermal bonding, so as to prevent leakage of fluid around the perimeter of the member.

Figure 39:
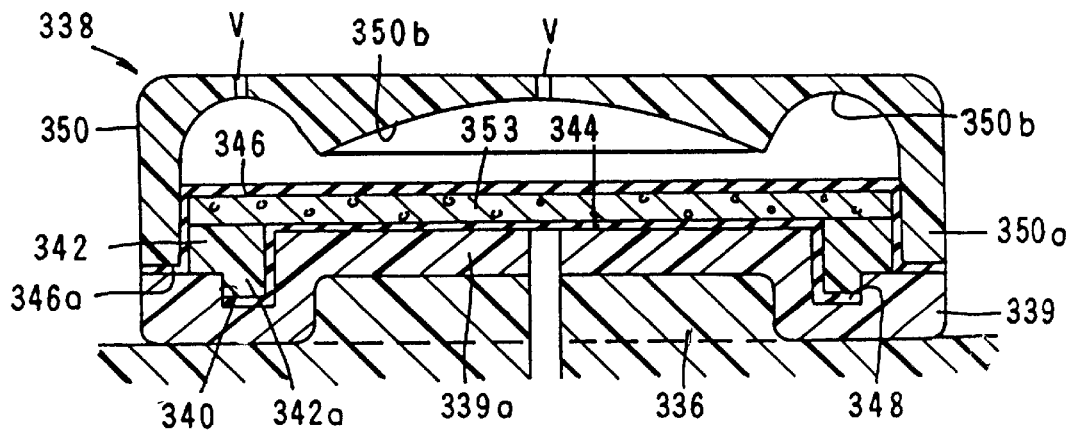
FIG. 39 is a cross-sectional view of the reservoir assembly shown in FIG. 38 as it appears in an assembled, unfilled configuration.

It is to be understood that distendable membrane 66 can comprise a single film layer or can comprise a laminate construction made up of a number of cooperating layers. In this regard, reference should be made to columns 10 and 11 of U.S. Pat. No. 5,411,480 which patent is incorporated herein by reference, wherein the various materials that can be used to construct membrane 66 are discussed in detail. Reference should also be made to columns 11 and 12 of this patent for the various materials that can be used in the construction of the cover and base subassemblies of the fluid delivery apparatus of the present invention. Reference to FIG. 39 of the patent will show a distendable membrane of a laminate construction that can be used in the construction of the fluid delivery device of the present invention (see also columns 17 and 18 of U.S. Pat. No. 5,411,480).

Referring particularly to FIG. 1, it is to be noted that inlet means shown here as an inlet 111 formed in base 70 is provided to enable the introduction of gel which forms the conformable ullage of this form of the invention. Inlet 111 communicates with a fluid passageway 112 which, in turn, communicates with the volume defined between the under surface 66a of membrane 66 and the upper surface 83a of barrier member 83. Inlet 111 is sealably closed by a bonded plug 114.

With the construction described in the preceding paragraphs and as shown in FIGS. 3 and 4, the conformable mass 77, which comprises the ullage defining means of the invention is disposed within a chamber defined by the upper surface 68a of base member 68 and the inner surface or wall 74a of cover 74. Ullage 77 is, as shown in the drawings, in direct engagement with distendable membrane 66 which, after being distended, will tend to return to its less distended configuration. It is to be noted that the shape of the conformable ullage will continuously vary as the distendable membrane distends outwardly from the base during reservoir filling and then tends to return to its less distended configuration during fluid delivery.

While the conformable ullage, or mass 77 is here constructed from a flowable gel, the conformable ullage can also be constructed from a number of materials such as various types of foams, fluids and soft elastomers. In some instances, the conformable ullage may comprise an integral conforming mass. In other instances, such as when a gel or fluid is used as the ullage medium, an encapsulation barrier member such as member 83 must be used to encapsulate the gel or fluid and to provide an appropriate interface to the fluid contained in the reservoir.

Once reservoir 82 is filled with fluid from the container subassembly of the fill assembly, the fluid will remain in the reservoir until such time as the luer cap 89 is removed from luer assembly 88 so as to open the outlet flow path of the fluid delivery assembly. Once the outlet flow path of the assembly is opened, distendable membrane 66 will tend to return to its less distended configuration and will act upon the conformable ullage 77 and the barrier member 83 in a manner to cause fluid to flow from reservoir 82 outwardly through flow passageways 81 and 86 and then into the outlet port 120 of the device via the flow control means 90.

Referring once again to FIGS. 5 and 7, it is to be noted that hollow housing 30 includes locking means for locking the housing within receiving chamber 13 of cover 74 after the fill subassembly has been mated with the fluid delivery device. These locking means are here provided in the form of a series of forwardly and rearwardly disposed locking teeth 122 and 124 respectively. As indicated in FIG. 5, these locking teeth and constructed so that they will slide under a flexible locking tab 126, which is provided proximate the entrance of receiving chamber 13, as the adapter subassembly is urged inwardly of receiving chamber 13. However, once the adapter subassembly has reached the fully inserted position shown in FIG. 5 wherein the fluid is transferred to reservoir 82, locking tab 126 will effectively prevent removal of housing 30 of the adapter subassembly from passageway 13. With this novel construction, once reservoir 82 has been filled with the fluid contained in the container subassembly, the adapter subassembly cannot be removed from the fluid delivery device and, therefore, cannot be reused thereby preventing system adulteration.

Also forming an important aspect of the present invention is the provision of viewing means for viewing at any time the volume of fluid contained within chamber 18 of the fluid container subassembly 14. In the form of the invention shown in the drawings, this viewing means takes the form of an elongated viewing window 130 which is provided in housing 30 (FIG. 7). As indicated in FIG. 7, the body portion 16 of the container subassembly is provided with a plurality of longitudinally spaced-apart index lines, or marks 132, which can be viewed through window 130 as the container subassembly is urged forwardly of housing 30 in the manner previously described. Index lines 132 provide reference points for observing the volume of fluid remaining within the container subassembly. A protuberance 30a formed on housing 30 in cooperation with channel 30b (FIG. 5) functions to provide polarized orientation of the subassembly.

Referring next to FIGS. 11 through 24 an alternate form of apparatus of the invention is there shown. This alternate embodiment is similar in many respects to that shown in FIGS. 1 through 10, but here includes novel operating means for controllably advancing the adapter assembly into the receiving chamber of the fluid delivery portion of the apparatus to cause a controlled flow of fluid through the outlet of the apparatus.

Figure 16:
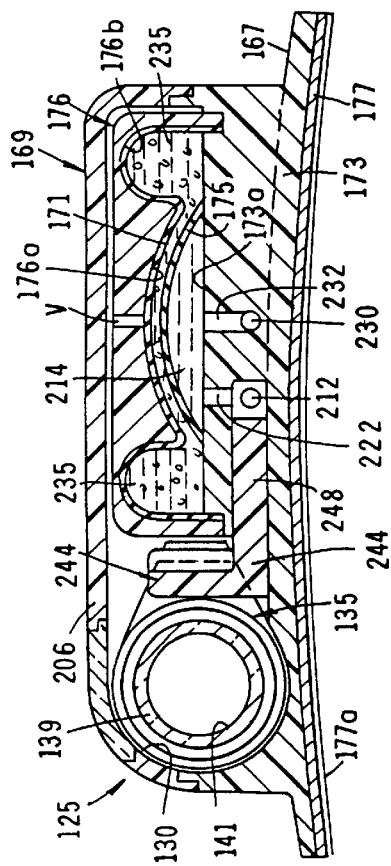
FIG. 16 is a cross-sectional view taken along lines 16—16 of FIG. 14.

As before, the apparatus of this latest form of the invention comprises two major cooperating assemblies, namely the fluid delivery assembly 125 shown in FIGS. 14 and 15 and the fill assembly 127 shown in FIG. 11. The fluid delivery assembly is similar in many respects to that previously described herein and to those disclosed in U.S. Pat. No. 5,205,820 in that it includes a base, a stored energy means which cooperates with the base to form a fluid reservoir and a cover assembly which overlays the base and encloses the stored energy means. Like the device shown in FIGS. 1 through 4, the fluid delivery assembly of the present invention includes novel conformable ullage means and a uniquely configured receiving chamber 130 which is formed between the base and cover assemblies (FIGS. 14A and 16). In a manner presently to be described, chamber 130 telescopically receives a portion of the fill assembly of the invention to permit controlled filling of the reservoir of the device and also to administer bolus doses of medication as may be required.

Turning particularly to FIGS. 11 and 12, the alternate form of the fill assembly portion of the apparatus is there shown and can be seen to comprise a container subassembly 133, an adapter subassembly 135, and a cover assembly 137, the character of which will presently be described. Container subassembly 133 includes a body portion 139, having a fluid chamber 141 for containing an injectable fluid "F". Chamber 141 is provided with first and second open ends 143 and 145 (FIG. 12). First open end 143 is sealably closed by closure means here provided in the form of a pierceable septum assembly 147. Septum assembly 147 is held securely in position by a clamping ring 147a. As best seen in FIGS. 11 and 12, a plunger 129 is telescopically movable within chamber 141 of container subassembly 133 between first and second locations.

As best seen in FIGS. 11 and 12, adapter subassembly 135 comprises a hollow housing 153 having a first open end 155 and a second closed end 157 (FIG. 12). Container subassembly 133 is telescopically receivable within open end 155 of housing 153 in the manner shown in FIG. 12 so that the housing can be moved from a first extended position to a second vial encapsulation position. As was earlier the case, the adapter subassembly includes pusher means shown here as an elongated pusher rod 159 (see also FIG. 13), which functions to move plunger 129 within the fluid chamber 141 of the container subassembly. Pusher rod 159 has a first end 159a interconnected with closure wall 157 and an opposite end 159b which engages plunger 129 and causes telescopic movement of the plunger within chamber 141.

Cover subassembly 137 of the fill assembly of this latest form of the invention comprises a generally cylindrically shaped cover 161 having a first open end 161a for telescopically receiving body portion 139 of container subassembly 133 (FIG. 11) and a second end 161b which is closed by a filter means shown here as a porous filter member or vent 163. Cover 161 initially circumscribes a major portion of the container subassembly, but is removable therefrom expose a substantial portion of body 139 of the container. As best seen in FIG. 11, a medicament label 164 circumscribes the fill assembly to provide a septic closure and also serves to prevent accidental separation of the cover 161 from the adapter subassembly 135. However, upon tearing the medicament label the cover assembly can be easily slipped from the container so as to expose to view septum assembly 147. Filter member 163 can be constructed from any suitable porous material that will permit air entrapped within the interior of cover subassembly 137 to be expelled to atmosphere as the subassembly is placed over container subassembly 133.

Turning particularly to FIGS. 14, 14A, 14B and 15 the fluid delivery assembly portion of the apparatus can be seen to include a base subassembly 167, a cover subassembly 169 which is receivable over base subassembly 167, and a stored energy means, here provided in the form of a distendable membrane 171 (FIGS. 15 and 15A). As best seen in FIG. 15A the periphery 171a of membrane 171 is sealably connected to a base member 173 which forms a part of base assembly 167. Distendable membrane 171, as well as a barrier member 175, the purpose of which will presently be described, are affixed to base member 173 by adhesive bonding, by sonic bonding, or by other suitable means in the manner shown in FIG. 15A. By way of example a reservoir defining member 176, which forms a part of base assembly 167, includes a protuberance, or energy director 176a which functions to cut membrane 171 and to direct sonic energy when member 176 is sonically bonded to base member 173 in the manner shown in FIG. 15A.

Affixed to the lower surfaces of the base assembly is a thin, planar shaped foam pad 177 (FIG. 15) having an adhesive coating provided on both its upper and lower surfaces. The adhesive coating on the upper surface of the pad enables the pad to be affixed to the lower surface of base assembly. As before, a peel strip 177a is connected to the bottom surface of foam pad 177 by the adhesive coating provided thereon. When the device is to be used, peel strip 177a can be stripped away from the pad so that the adhesive on the lower surface thereof can be used to releasably affix the apparatus of the invention to the patient's body.

Figure 17A:
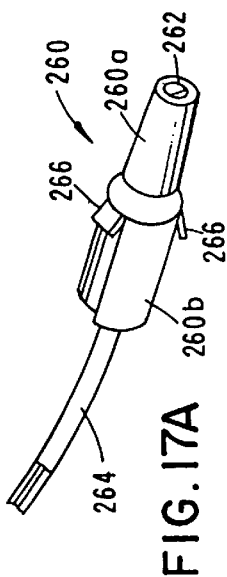
FIG. 17A is a generally perspective view of one form of the quick coupler assembly which forms a part of the fluid delivery means of the invention.
Figure 17:
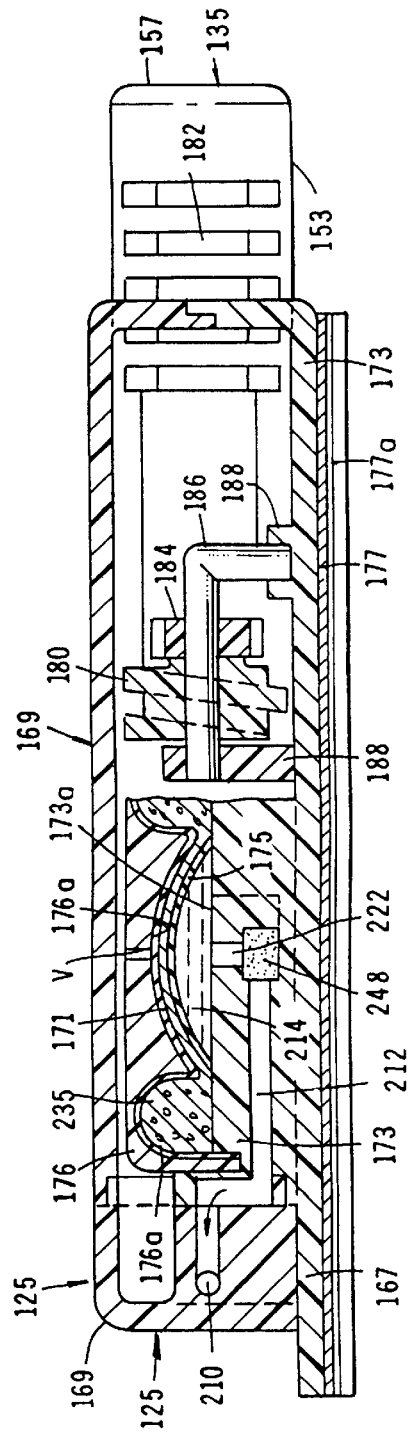
FIG. 17 is a cross-sectional view taken along lines 17—17 of FIG. 14.

An extremely important feature of the apparatus of the latest embodiment of the invention is the provision of the previously mentioned bolus delivery means for delivering bolus doses of medication to the patient. The bolus delivery means here includes operating means for accomplishing closely controlled fluid flow through the outlet of the fluid delivery assembly. As best seen in FIGS. 14, 15, 17, and 18A, the operating means of the present form of the invention comprises driving means, including a drive wheel 180, which is rotatably carried by base member 173 and driven means, which here comprises a plurality of longitudinally spaced-apart engagement members, or teeth like portions, 182 provided on hollow housing 153. As shown in FIG. 18A, drive wheel 180 along with a first screw gear 184 are mounted on a first shaft 186 which is carried by spaced-apart shaft supports 188 formed on base member 173 (FIG. 17). Screw gear 184 along with drive wheel 180 are driven by a second screw gear 190, which along with a finger engaging or thumb wheel 192, is mounted on a second shaft 194 which is rotatably supported by supports 195 in the manner best seen in FIG. 15. Thumb wheel 192 is engageable by the user through an aperture provided in the cover through which a portion of the thumb wheel extends.

Also carried by second shaft 194 is an anti-reverse rotation gear 196, an indexing disc 198, and an indicator disc 200, the purpose of each of which will presently be described. For example, illustrated in FIG. 21, the anti-reverse rotation gear 196 comprises a toothed member which cooperates with a tooth engaging clip 202 mounted on base member 173 to permit rotation of the gear only in one direction.

Indexing disc 198 and indicator disc 200 both comprise a part of the control means of the invention for controlling bolus flow outwardly of the device as a result of the controlled advancement of hollow housing 153 within receiving chamber 130. The details of operation of the control means will be later discussed in connection with an overall discussion of the operation of the apparatus of this latest form of the invention.

Figure 18:
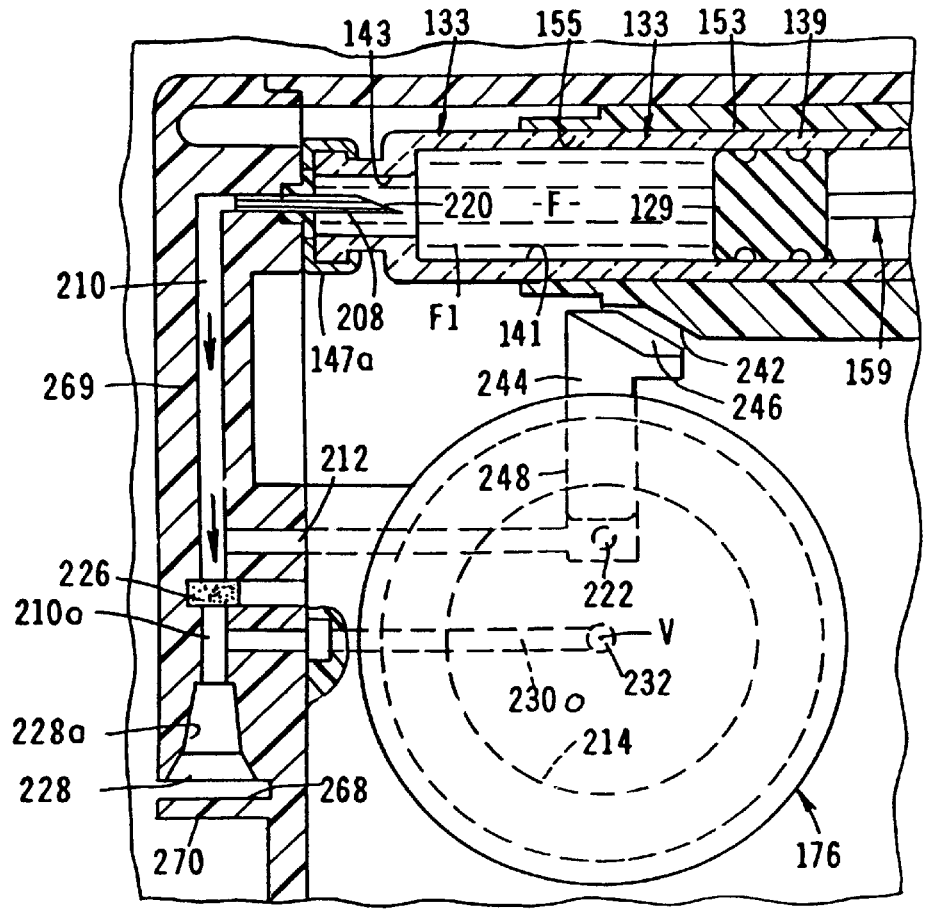
FIG. 18 is a fragmentary, plan view, partly in cross section, of a portion of the apparatus of this latest form of the invention illustrating in particular the advancement of the adapter assembly into the fluid delivery portion of the apparatus and showing the path of flow of the bolus dose.
Figure 18B:
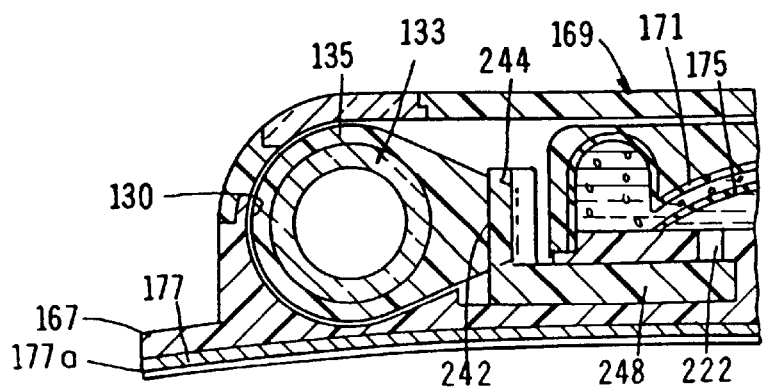
FIG. 18B is a cross-sectional view taken along lines 18B—18B of FIG. 18A.
Figure 18A:
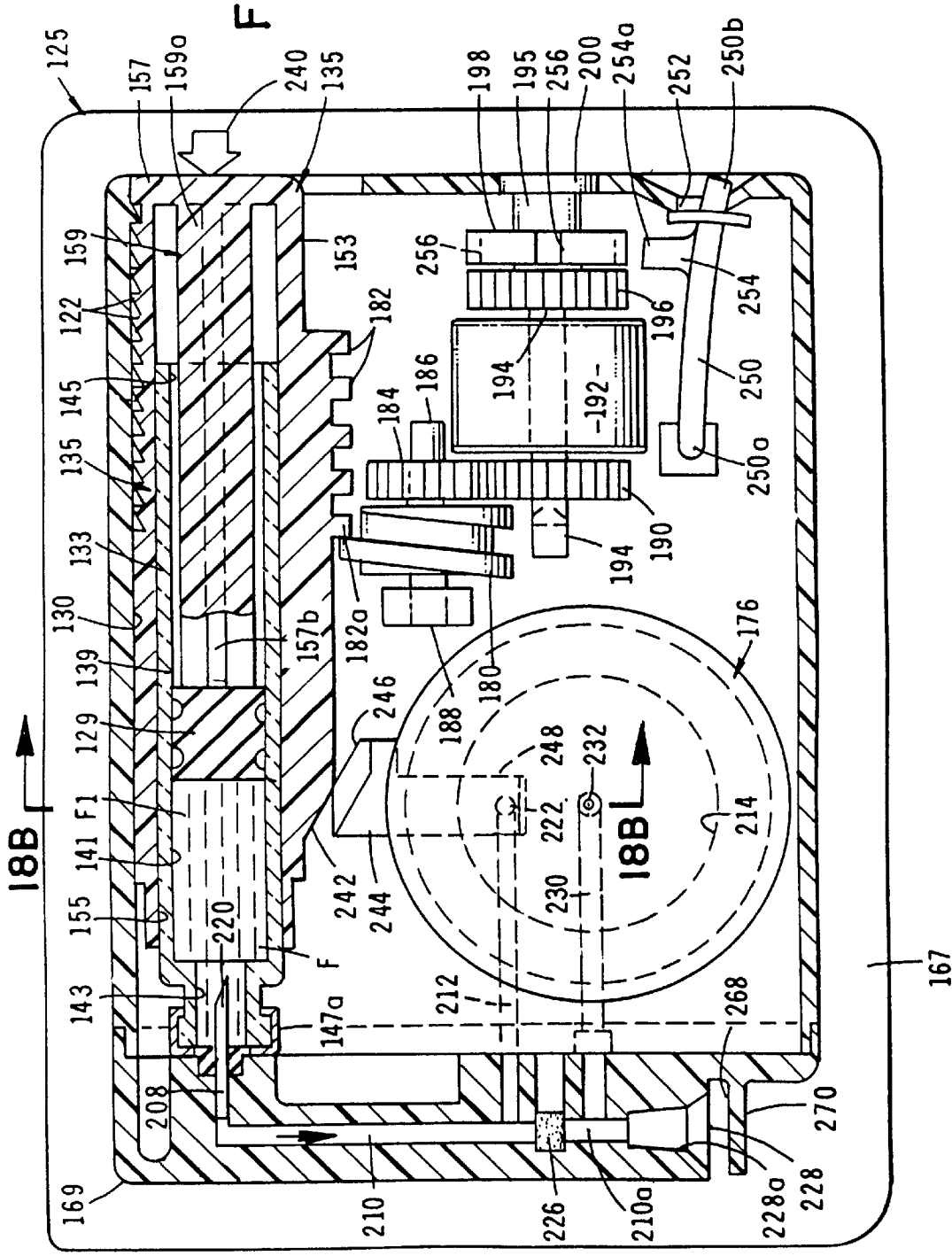
FIG. 18A is a view similar to FIG. 14 but showing in greater detail the construction of the advancing means of the invention for controllably advancing the adapter assembly into the fluid delivery portion of the apparatus.

Turning now particularly to FIGS. 14, 16 and 18, the previously identified elongated receiving chamber 130, which is adapted to receive a portion of the fill subassembly of the invention, can be seen to be strategically located between base 173 and cover member 206 of cover assembly 169. In a manner presently to be described, the fluid chamber 141 of container 139 of the fill subassembly communicates via passageways 208, 210 and 212 with the fluid reservoir 214 of the fluid delivery assembly 125, which reservoir is uniquely formed between a deformable barrier member 175 and the upper surface 173a of base member 173 (see also FIGS. 15, 16 and 17). Disposed between barrier member 175 and distendable membrane 171 is the important conformable ullage means of this latest form of the invention which is similar in many respects to that described in connection with FIGS. 1 through 4.

Passageway 208, which is formed within a hollow piercing cannula 220 communicates with passageway 210 which, in turn, communicates with passageway 212 that terminates in inlet 222 of reservoir 214. Passageway 210 also communicates via a porous plug 226 with a continuation passageway 210a which, in turn, communicates with the outlet port 228 of the fluid delivery assembly 125. Outlet port 228 includes a tapered wall portion 228a which sealably receives the tapered portion of a novel quick connect coupler which comprises a part of the fluid delivery means of the invention. As best seen in FIG. 18, continuation passageway 210a also communicates with an outlet passageway 230 which leads to the outlet port 232 of fluid reservoir 214.

In using the apparatus of the invention, with the fill assembly in the filled configuration shown in FIG. 12, the cover subassembly 137 is first removed from the container subassembly to expose the forward portion of the container subassembly and septum 147. This step readies the adapter subassembly for interconnection with the fluid delivery assembly 125 of the invention in the manner shown in FIG. 14.

In mating the adapter subassembly with the fluid delivery assembly, the container subassembly is first telescopically inserted into receiving chamber 130 of the fluid delivery assembly and the adapter subassembly is then pushed forwardly to the position indicated by the solid lines in FIG. 14. The pushing force exerted on the adapter subassembly will cause piercing cannula 220, which extends into receiving chamber 130, to pierce septum 147. Once a fluid flow path between fluid chamber 141 of the container subassembly and the fluid reservoir 214 of the fluid delivery assembly is thus created, a continued movement of the adapter subassembly toward the solid line position shown in FIG. 14 will cause pusher rod 159 to move plunger 129 forwardly of chamber 130 to the position shown in the solid lines of FIG. 14. As plunger 129 is moved forwardly of chamber 141, a portion of the fluid "F" contained within the chamber will flow into passageway 208 of the piercing cannula, into passageway 210, into passageway 212 and then into fluid reservoir 214 via inlet 222. As the fluid under pressure flows into reservoir 214, barrier member 175 will be distended outwardly in the manner shown in FIG. 15 and will uniformly deform the conformable ullage means, shown here as a gel 235. As gel 235 moves outwardly from surface 173a and into a toroidal chamber 176b formed in member 176, the distendable membrane 171 will distend outwardly until it reaches the position shown in FIG. 15 where it engages inner wall 176a of reservoir defining member 176. Gases contained in the volume between wall 176a and distendable membrane 171 will be vented to atmosphere via vent passageway "V" (FIG. 15). In the manner best seen in FIG. 15A, reservoir forming member 176 which is bonded to base 173 functions to capture and seal the distendable membrane about its periphery. In a similar manner, the periphery of the barrier member 175 is sealably affixed to base 173 as by adhesive or thermal bonding, so as to prevent leakage of fluid around the periphery of the member.

It is to be understood that distendable membrane 171 can comprise a single film layer or can comprise a laminate construction made up of a number of cooperating layers. In this regard, reference should be made to columns 10 and 11 of U.S. Pat. No. 5,411,480 which patent is incorporated herein by reference, wherein the various materials that can be used to construct membrane 171 are discussed in detail. Reference should also be made to columns 11 and 12 of this patent for the various materials that can be used in the construction of the cover and base subassemblies of the fluid delivery apparatus of the present invention. Reference to FIG. 39 of the patent will show a distendable membrane of a laminate construction that can be used in the construction of the fluid delivery device of the present invention (see also columns 17 and 18 of U.S. Pat. No. 5,411,480).

With the construction described in the preceding paragraphs and as shown in FIGS. 15, 15A, and 16, the conformable mass or gel, which comprises the ullage defining means of this form of the invention is disposed within a chamber defined by the upper surface of the barrier membrane 175 and the inner surfaces of base 173 and reservoir defining member 176. As indicated in the drawings, the ullage or gel 235 is in direct contact with distendable membrane 171 which, after being distended, will tend to return to its less distended configuration. It is to be noted that the shape of the conformable ullage will continuously vary as the distendable membrane distends outwardly from the base during reservoir filling and then as it tends to return to its less distended configuration during the basal fluid delivery step.

While the conformable ullage, or mass 235 is here constructed from a flowable gel, the conformable ullage can also be constructed from a number of materials such as various types of foams, fluids and soft elastomers.

Once reservoir 214 is filled with fluid from the container subassembly of the fill assembly, the fluid will remain in the reservoir until such time as the outlet flow path of the fluid delivery assembly is opened to fluid flow. Once the outlet flow path of the assembly is opened, distendable membrane 171 will tend to return to its less distended configuration and will act upon the conformable ullage 235 and the barrier member 175 in a manner to cause fluid to flow from reservoir 214 outwardly through a reservoir outlet 232 via an appropriate rate control means. The fluid will next flow into passageways 230 and 210a and finally outwardly of the device via the fluid delivery means of the apparatus, the character of which will presently be described. It is to be noted that due to impedance offered by porous member 226 to upstream flow, the fluid will tend to flow downstream toward the fluid delivery means via passageway 210a.

Considering next the extremely important bolus delivery means of the apparatus of the invention, this novel means enables the patient to receive both a selected basal dose of medication from reservoir 214 and also a bolus dose of medication from chamber 141 of container 139. Typically insulin is maintained from the manufacturer prepackaged in 1.0 ml vials. A portion of this quantity can be used for basal delivery, a portion for incremental bolus delivery on demand, and the balance, if any, for residual within the device. For example, if insulin is being delivered at a basal rate, the patient may receive from reservoir 214 up to one-half milliliter over a period of 24 hours. Additionally should the patient determine that the blood sugar level is unduly high, a bolus injection of a predetermined volume can quickly and easily be simultaneously accomplished through use of the controlled incremental bolus injection means of the invention thereby supplementing as necessary the basal dose being delivered from the fluid reservoir 214.

Referring particularly to FIG. 18A, after the adapter subassembly 135 has been pushed forwardly into the position there shown, reservoir 214 has been filled and further forward movement of the subassembly within receiving chamber 130 is temporarily blocked by the engagement of tooth 182a with drive wheel 180. It should also be noted that as the adapter subassembly 135 is pushed forwardly of chamber 130 in the direction of the arrow 240 of FIG. 18A, a angularly inclined valve member engaging surface 242 which is provided on housing 153, engages the valve means of the invention which functions to control fluid flow toward fluid inlet 222 of reservoir 214. As best seen by also referring to FIG. 18, this novel valve means here comprises an inwardly extending, slidably movable operating arm 244 having at one end a sloping camming surface 246 which is engageable by surface 242 of housing 153. Provided at the opposite end of arm 244 is a port closure member 248 which functions to close port 222 when arm 244 is in its inwardmost position (FIG. 17). With this construction as surface 242 engages camming surface 246, member 244 will be moved relative to base 173 from an inlet port open position shown in FIG. 14 to the inlet closing position shown in FIGS. 17 and 18A wherein port closure member 248 blocks and substantially seals against further fluid flow into fluid reservoir 214 via inlet 222. When reservoir inlet 222 is closed by the valve means, it is apparent that the fluid "F1" remaining in fluid chamber 141 is precluded from flowing into the fluid reservoir 214 via inlet 222. However, it is important to note that upon further advancement of the adapter subassembly, the fluid F1, which remains in fluid chamber 141, is free to flow into cannula passageway 220, into passageway 210 through impedance 226 and then into passageway 210a of the fluid delivery assembly.

To cause the fluid F1 which remains within chamber 141 to flow outwardly of the device, the finger engaging means, or thumb wheel 192, of the operating means of the invention must be rotated. As previously discussed, rotation of thumb wheel 192 will impart rotation to first screw gear 184 and also to drive wheel 180. Turning to FIG. 18C, it is to be observed that rotation of drive wheel 180 of the drive means relative to adapter housing 153 will cause the controlled advancement of the adapter assembly from the position shown in FIG. 18A to the position shown in FIG. 18C. As the adapter assembly 153 is thus moved incrementally inwardly of receiving chamber 130, plunger 129 will move incrementally forwardly of chamber 141 causing a portion of the fluid F1 contained within chamber 141 to be expelled outwardly of the chamber via cannula passageway 208 and delivery passageways 210 and 210a.

Another important feature of the fluid delivery assembly of the invention is control means for controlling the rotation of drive wheel 180 and thereby controlling the bolus volume flowing from the apparatus via outlet port 228. This novel control means, which forms a part of the operating means of the invention, includes the previously identified indexing disc 198. Also forming a part of the control means of the invention is safety interlocking means for controlling rotation of indexing disc 198. This interlocking means here comprises a locking shaft 250 having first and second ends 250a and 250b. Shaft 250 is connected to base 173 proximate its first end 250a in a manner such that end 250b extends outwardly of the cover through an opening 252 pro-vided therein. Provided intermediate ends 250a and 250b of shaft 250, is an engagement arm 254 which, as best seen in FIG. 19, includes an end portion 254a, which is biased toward and receivable in a selected one of four circumferentially spaced slots 256 provided in control wheel 198, which slots are here spaced apart 90 degrees. With this construction so long as end portion 254a is received within one of the slots 256, rotation of indexing disc 198 as well as rotation of the finger engaging or thumb wheel 192 of the apparatus is effectively prevented. However, upon transverse movement of control shaft 250 from its normal inwardly biased locking position into the unlocked position shown in FIG. 18, a rotation of disc 198 and wheel 192 is possible.

As wheel 192 is rotated, wheel 190 will engage and rotate screw gear 184 which, in turn, will rotate drive wheel 180 causing an incrementally controlled, telescopically inward movement of adapter assembly 153 into receiving chamber 130. With this unique construction, it is apparent that the volume of the fluid F1 remaining within the chamber can be likewise precisely incrementally displaced from the chamber by closely controlling the extent of rotation of control wheel 198. By way of example for insulin use, if chamber 141 is sized to contain 1.0 milliliter of liquid and if 0.5 milliliter of liquid is required to fill reservoir 214, then the liquid or fluid F1 remaining in chamber 141 after filling reservoir 214 is approximately 0.5 milliliter of insulin. Similarly, if teeth 182 and drive wheel 180 are designed so that one full rotation of drive wheel 180 will advance adapter assembly 153 a distance to cause plunger 129 to move one-fourth of the remaining distance of chamber 141 that is filled with fluid F1, then four complete revolutions of drive wheel 180 would result in the delivery to the fluid delivery means of the invention of the all of the fluid F1 remaining in chamber 141. It follows, therefore, that one rotation of drive wheel 180 would deliver one quarter of the volume or one tenth (0.1) milliliter of the fluid remaining within chamber 141. Accordingly, rotation of wheel 198 through one-quarter of a turn, that is the distance between adjacent notches 256, would result in the delivery of one-quarter of one tenth (0.025) milliliter of liquid per quarter rotation of wheel 198. With this unique arrangement, it is apparent that as desired by the user, a volume of between one quarter of one tenth milliliter (0.025 ml) and 0.4 milliliters of liquid can be delivered from the apparatus by the bolus delivery means depending upon the extent to which the control wheel 198 is permitted to be rotated. For example, if locking shaft 250 is maintained in the open, unlocked position shown in FIG. 18A, a continued rotation of thumb wheel 192 will result in free rotation of the control wheel 198 and will permit complete dispensing of the fluid F1 from the device. Conversely, if locking shaft 250 is manipulated to only remove end portion 254a from the slot in which it resides and then is released, wheel 198 will turn one quarter of a turn and then will be blocked from further rotation as end portion 254 moves into the next succeeding notch 256 due to the urging of biasing shaft 250. This one quarter of a turn of wheel 198 will then result in the delivery of precisely one quarter of one tenth milliliter of liquid from the fluid F1 remaining in chamber 141. It is to be understood that chamber 141 of container 139 can be of various volumes and that the control wheel can be notched in a manner to permit delivery of any desired increment of the liquid volume of chamber 141.

As previously mentioned, the beneficial agent flowing through outlet 228 will be received within the fluid delivery means, which includes tapered outlet cavity 228a. Cavity 228a is adapted to receive a quick connect delivery fitting 260 that also comprises a part of the delivery means of the invention. As shown in FIG. 17A, fitting 260 includes a tapered inboard end portion 260a and a body portion 260b. A central bore 262 extends through portions 260a and 260b and communicates at its outboard end with a cannula 264 which also forms a part of the delivery means of the invention for delivering fluids from the device. When fitting 260 is seated within outlet 228 (FIG. 18), the inboard end of bore 262 communicates with continuation passageway 210a which, in turn, communicates with passageway 210 and cannula 220.

In order to lock quick connect delivery fitting 260 in the fluid delivery position, locking means shown here as resiliently deformable locking tabs 266 are provided on the body portion 260b of fitting 260. Tabs 266 lockably engage a locking surface 268 provided on a connector receiving ring 270 form on front housing 269 (FIG. 18). Upon pushing inwardly on fitting 260, tabs 266 will yieldably deform inwardly so that tapered portion 260a of the fitting can be introduced into outlet 228. As the fitting seats within the chamber, the resiliently deformable locking tabs will spring outwardly and engage locking surface 268 in a manner to lockably interconnect the delivery means with the front housing 269. With the quick connect fitting thus in place, the beneficial agent contained within reservoir 214 can flow outwardly of the apparatus through delivery cannula 264.

Figure 22:
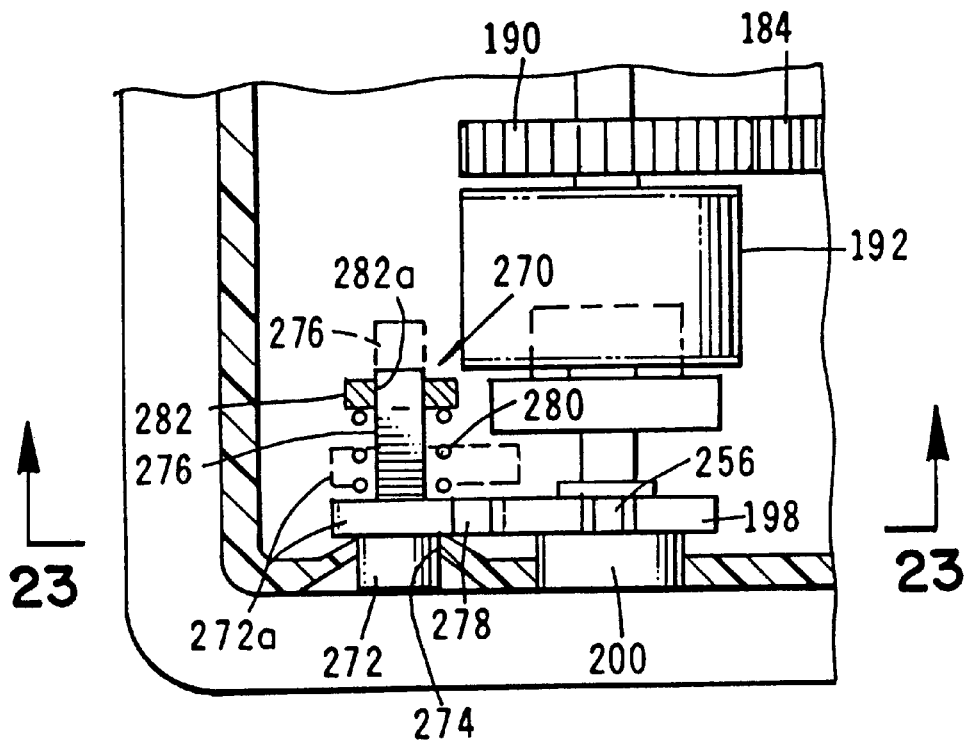
FIG. 22 is a fragmentary, cross-sectional view of a portion of the apparatus showing the construction of an alternate locking means for controlling rotation of the driving wheel of the invention.
Figure 23:
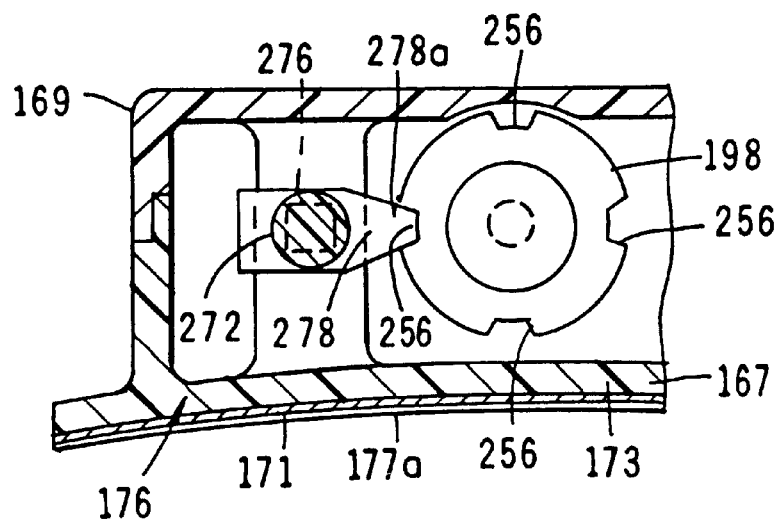
FIG. 23 is a cross-sectional view taken along lines 23—23 of FIG. 22.

Turning next to FIGS. 22 and 23, an alternate form of control means for controlling the rotation of drive wheel 180 is there shown. This novel control means, which forms a part of the operating means of the invention, includes the previously described indexing disc 198 and also includes a slightly different form of safety interlocking means for controlling rotation of indexing disc 198. This locking means here comprises a push button assembly 270 having a finger engaging hub 272 which extends outwardly of the cover through an opening 274 provided therein. Push button, or hub, 272 is connected to an inwardly extending shaft 276 to which an engagement arm 278 is connected. Shaft 276 and push button 272 are biased outwardly by a coil spring 280 which is contained between a flange 272a connected to button 272 and a support 282 having an aperture 282a adapted to slidably receive shaft 276.

As best seen in FIG. 23, end 278a of engagement arm 278 is receivable in a selected one of four circumferentially spaced slots 256 provided in control wheel 198, which slots are here spaced apart by 90 degrees. With this construction so long as end 278a of arm 278 is received within one of the slots 256, rotation of indexing disc 198 as well as rotation of the finger engaging or thumb wheel 192 of the apparatus is effectively prevented. However, upon pushing button 272 and shaft 276 inwardly from their normal outwardly biased locking position into the locking position shown by the phantom lines in FIG. 22, rotation of disc 198 and wheel 192 is possible.

As before, as wheel 192 is rotated, wheel 190 will engage and rotate screw gear 184 which, in turn, will rotate drive wheel 180 causing a telescopically inward movement of adapter assembly 153 into receiving chamber 130. With this alternate construction, it is apparent that, as before, the volume of the fluid F1 remaining within the chamber can be precisely dispensed from the chamber by closely controlling the extent of rotation of control wheel 198.

Turning next to FIGS. 24 and 25, another form of the apparatus of the invention is there shown. This form of the apparatus is very similar to that shown in FIGS. 14 through 23 and like numbers are used to identify like components. The major difference between this latest embodiment and that previously described resides in the fact that, unlike the embodiment shown in FIGS. 14 through 23, this latest form of the apparatus of the invention is not designed to be interconnected directly with the patient's body, but rather comprises a free standing unit which can be carried by the patient or attached to the patient's clothing. Therefore, the casing or housing of the device does not include an adhesive coated foam pad 177 of the character shown in FIGS. 15, 16, and 17.

Referring particularly to FIGS. 24, 25, and 28, the fluid delivery assembly portion of the apparatus can be seen to include a base subassembly 277, a cover subassembly 279, including forward portion 279b which is receivable over base subassembly 277, and a fluid reservoir defining means, or reservoir unit, which includes a stored energy means, here provided in the form of a distendable membrane 281 (FIGS. 25, 28, and 29A). Distendable membrane 281, in cooperation with a barrier member 283, functions to encapsulate the ullage defining means of this form of the invention, which means also comprises a part of the reservoir defining means. The details of the reservoir defining means will be described more fully in the paragraphs which follow.

This latest embodiment of the invention also includes a novel bolus delivery means of the character previously described for delivering bolus doses of medication to the patient. As before, the bolus delivery means includes operating means for accomplishing closely controlled fluid flow through the outlet of the fluid delivery assembly. The operating means of the present form of the invention is virtually identical in construction and operation to that described in connection with FIGS. 14, 15, 17, and 18A and like numbers have been used in FIGS. 24 through 29 to identify like components of this important bolus delivery means.

Turning particularly to FIGS. 24, 26, 27, and 29, an elongated receiving chamber 285 is provided between base subassembly 277 and cover assembly 279 and is adapted to receive a portion of the fill subassembly 127 of the invention. Once again, the fill assembly of the invention is identical to that shown in FIGS. 11 and 12 and includes a container subassembly 133, an adapter subassembly 135, and a cover assembly 137 (FIG. 11) all of which are of the same construction and operate in the same manner as previously described herein. As best seen in FIGS. 26 and 28, the fluid chamber 141 of container 139 of the fill subassembly communicates via passageways 288, 290 and 292 with the reservoir defining means which functions to define fluid reservoir 294 of the fluid delivery assembly.

Reservoir is uniquely formed between deformable barrier member 283 and the upper surface 296*a* of a base member 296 which forms a part of base subassembly 277. As previously mentioned, disposed between barrier member 283 and distendable membrane 281 is the important conform-able ullage means of this latest form of the invention which is similar in many respects to that described in connection with FIGS. 14 through 17.

Passageway 288, which is formed within hollow piercing cannula 220 communicates with passageway 290 which, in turn, communicates with passageway 292 that terminates in inlet 300 of reservoir 294 (FIG. 29). Passageway 290 also communicates via a porous plug 226 with a continuation passageway 290*a* which, in turn, communicates with the outlet port 302 of the fluid delivery assembly. Outlet port 302 includes a tapered wall portion 228*a* which sealably receives the tapered portion of the quick connect coupler assembly 260 (FIG. 17A) which comprises a part of the fluid delivery means of the invention, which means is also identical to that previously described. As best seen in FIG. 26, continuation passageway 290*a* also communicates with an outlet passageway 304 which leads to the outlet port 306 of fluid reservoir 294.

In using the apparatus of the invention, with the reservoir defining means mated with the base and with the fill assembly in the filled configuration shown in FIG. 12, the cover subassembly 137 is first removed from the container subassembly to expose the forward portion of the container subassembly and septum 147. This step readies the adapter subassembly for interconnection with the fluid delivery assembly of the invention in the manner shown in FIG. 26.

In mating the adapter subassembly with the fluid delivery assembly, the container subassembly is first telescopically inserted into receiving chamber 285 of the fluid delivery assembly and the adapter subassembly is then pushed forwardly to the position shown in FIG. 30. The pushing force exerted on the adapter subassembly will cause piercing cannula 288, which extends into receiving chamber 285, to pierce septum 147. Once a fluid flow path between fluid chamber 141 of the container subassembly and the fluid reservoir 294 of the fluid delivery assembly is thus created, a continued movement of the adapter subassembly toward the position shown in FIG. 30 will cause pusher rod 159 to move plunger 129 forwardly of chamber 141 to the position shown in FIG. 30. As plunger 129 is moved forwardly of chamber 141, a portion of the fluid "F" contained within the chamber will flow into passageway 288 of the piercing cannula, into passageway 290, into passageway 292 and then into fluid reservoir 294 via inlet 300. As the fluid under pressure flows into reservoir 294, barrier member 283 will be distended outwardly in the manner shown in FIG. 28 and will uniformly deform the conformable ullage means, shown here as a fluid medium 309. As medium 309 moves outwardly from surface 296*a*, the distendable membrane 281 will distend outwardly until it reaches the position shown in FIGS. 28 and 29. Gases contained in the volume between the cover subassembly and distendable membrane 281 will be vented to atmosphere via vent passageway "V" (FIG. 28).

In addition to distendable membrane 281, barrier member 283 and the conformable ullage, the reservoir defining means also includes an outer membrane retaining ring 312 and an internal clamping ring 314. In the manner best seen in FIGS. 25, 28, 32, 33, and 34, the outer membrane retaining ring 312 and the internal clamping ring 314 cooperate to capture and seal both the distendable membrane and the barrier membrane about their periphery. More particularly, the periphery 283*a* of barrier member 283 is sealed relative to base 296, by clamping ring 314, while the periphery 281*a* of distendable membrane 281 is sealably clamped between an internal shoulder 312*a* formed on outer membrane retaining ring 312 and the top surface 314*a* of internal clamping ring 314. It is to be noted that base 296 is provided with an annular groove 315 which receives the lower peripheral portion of ring 312 so that the entire reservoir assembly shown in FIG. 25 can be assembled as a unit 313 with base 296. For this purpose, base 296 is provided with an upstanding, generally ring-shaped reservoir assembly receiving ring portion 296*b*, which defines surface 296*a* that forms the base of reservoir 294.

As before, distendable membrane 281 can take the various forms described in U.S. Pat. No. 5,411,480 which is incorporated herein by reference.

With the construction described in the preceding paragraphs, when the reservoir defining means, shown here as reservoir assembly 313, is assembled with base 296 in the manner shown in FIGS. 28 and 29, the conformable mass or ullage fluid, which comprises the ullage defining means of this form of the invention is disposed within a chamber defined by the lower surface of the distendable membrane 281, the upper surface of the barrier membrane 283 and the inner surface of clamping ring 314. As indicated in the drawings, the ullage or fluid medium 309 is in direct contact with distendable membrane 281 which, after being distended in the manner shown in FIG. 28, will tend to return to its less distended configuration. It is to be noted that the shape of the conformable ullage will continuously vary as the distendable membrane distends outwardly from the base during reservoir filling and then as it tends to return to its less distended configuration during the basal fluid delivery step.

Once reservoir 294 is filled with fluid from the container subassembly of the fill assembly, the fluid will remain in the reservoir until such time as the outlet flow path of the fluid delivery assembly is opened to fluid flow. Once the outlet flow path of the assembly is opened, distendable membrane 281 will tend to return to its less distended configuration and will act upon the conformable ullage 309 and the barrier member 283 in a manner to cause fluid to flow from reservoir 294 outwardly through reservoir outlet 306. The fluid will next flow into passageways 304 and 290*a* and finally outwardly of the device via the fluid delivery means of the apparatus. As before, the impedance offered by porous member 226 to upstream flow, the fluid will tend to flow downstream toward the fluid delivery means via passageway 290*a*.

The important bolus delivery means of the apparatus of this latest form of the invention, enables the patient to receive both a selected basal dose of medication from reservoir 294 and also a bolus dose of medication from chamber 141 of container 139.

Referring particularly to FIG. 30, after the adapter subassembly 135 has been pushed forwardly into the position there shown, reservoir 294 has been filled and further forward movement of the adapter subassembly within receiving chamber 285 is temporarily blocked by the engagement of tooth 182*a* with drive wheel 180. It should also be noted that as the adapter subassembly 135 is pushed forwardly of chamber 285, a angularly inclined valve member engaging surface 242 which is provided on housing 153, engages the valve means of the invention which functions to control fluid flow toward fluid inlet 300 of reservoir 294. This novel valve means is identical in operation and construction to that previously described in connection with FIGS. 14 through 23 and comprises an inwardly extending, slidably movable operating arm 244 having at one end a sloping camming surface 246 which is engageable by surface 242 of housing 153. Provided at the opposite end of arm 244 is a port closure member 248 which func-tions to close port 300 when arm 244 is in its inward-most position (FIG. 30). With this construction as surface 242 engages camming surface 246, member 244 will be moved relative to base 296 from an inlet port open position to the inlet closing position shown in FIG. 30 wherein port closure member 248 blocks further fluid flow into fluid reservoir 294.

To cause the fluid F1 which remains within chamber 141 to flow outwardly of the device, the operating means of the invention is operated in the manner previously described by rotation of the thumb wheel 192, a portion of which extends through an access opening 279a provided in cover 279 (FIG. 24). Rotation of thumb wheel 192 and the concomitant rotation of drive wheel 180 of the drive means relative to adapter housing 153 will cause the controlled advancement of the adapter assembly within receiving chamber 285. As the adapter assembly 153 moves incrementally inwardly of receiving chamber 285, plunger 129 will simultaneously move forwardly of chamber 141 causing a portion of the fluid F1 contained within chamber 141 to be expelled outwardly of the chamber via cannula passageway 288 and then into passageways 290 and 290a.

Another important feature of the fluid delivery assembly of this latest form of the invention is control means for controlling the rotation of drive wheel 180 and thereby controlling the bolus volume flowing from the apparatus via outlet port 302. This control means, which forms a part of the operating means of the invention, is identical in construction and operation to that previously described herein.

When the adapter subassembly is fully inserted into receiving chamber 285, locking means of the character previously described, which includes locking teeth 122 and locking tab 126, will lock the adapter subassembly to the base assembly thereby preventing system adulteration (FIG. 27).

Figure 32:
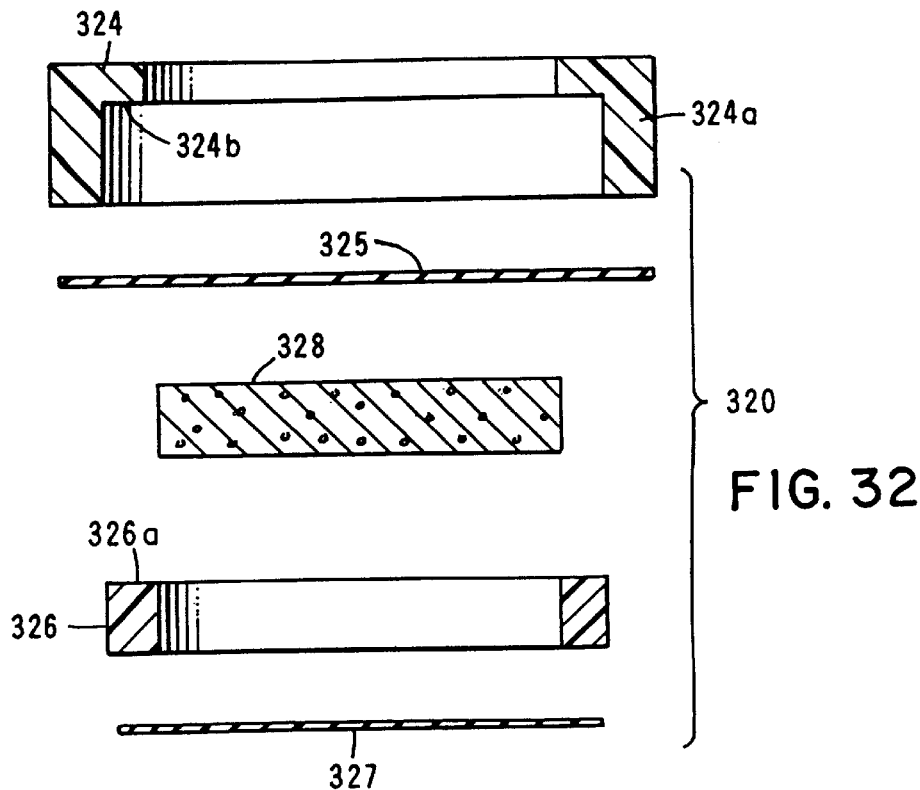
FIG. 32 is a cross-sectional, exploded view of the reservoir assembly of the apparatus shown in FIGS. 24 through 31.
Figure 33:
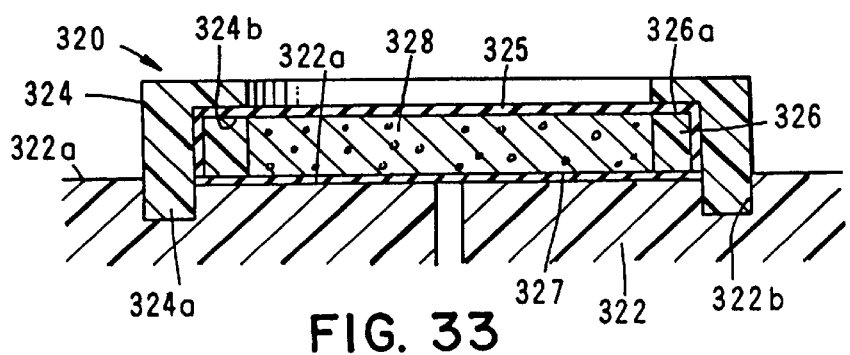
FIG. 33 is a cross-sectional view of the reservoir assembly shown in FIG. 32 as it appears in an assembled, unfilled configuration.
Figure 34:
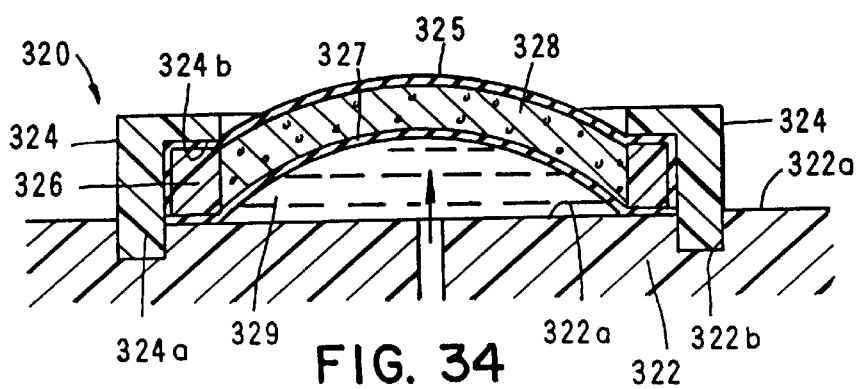
FIG. 34 is a cross-sectional view similar to FIG. 33, but showing the reservoir assembly in a filled configuration.

Turning next to FIGS. 32 through 34, an alternate form of reservoir assembly is there shown and generally designated by the numeral 320. This reservoir assembly or unit is similar to that shown in FIGS. 24 through 31 save that the unit mates with the base of the fluid delivery device in a slightly different manner. More particularly, as best seen in FIG. 33, the base 322 of the fluid delivery device of this alternate form of the invention is provided with a generally flat surface 322a which is provided with a circular groove 322b that is adapted to closely receive a skirt portion 324a of a strategically shaped retainer member 324 (see also FIG. 32). With this construction, a distendable membrane 325 is sealably clamped between an internal shoulder 324b formed on member 324 and the upper surface 326a of a clamping ring 326.

A barrier membrane 327 extends over the upper surface 322a of base 322 and is clamped there against about its periphery by clamping ring 326 in the manner shown in FIGS. 33 and 34. Disposed between distendable membrane 325 and barrier membrane 327 is a conformable ullage defining means here shown as a gel 328.

In operation, as the fluid under pressure flows into the reservoir 329, which is defined by the lower surface of the barrier membrane 327 and the upper surface 322a of the base 322, barrier member 327 will be distended outwardly from the position shown in FIG. 33 to the position shown in FIG. 34 and will uniformly deform the conformable ullage means or gel 328. As the gel moves outwardly from the upper surface of the base, the distendable membrane 325 will distend outwardly until it reaches the position shown in FIG. 34. As before, the entire reservoir assembly 320 can be assembled as a unit with base 322 and will function with the base assembly in the same manner as previously described.

Figure 35:
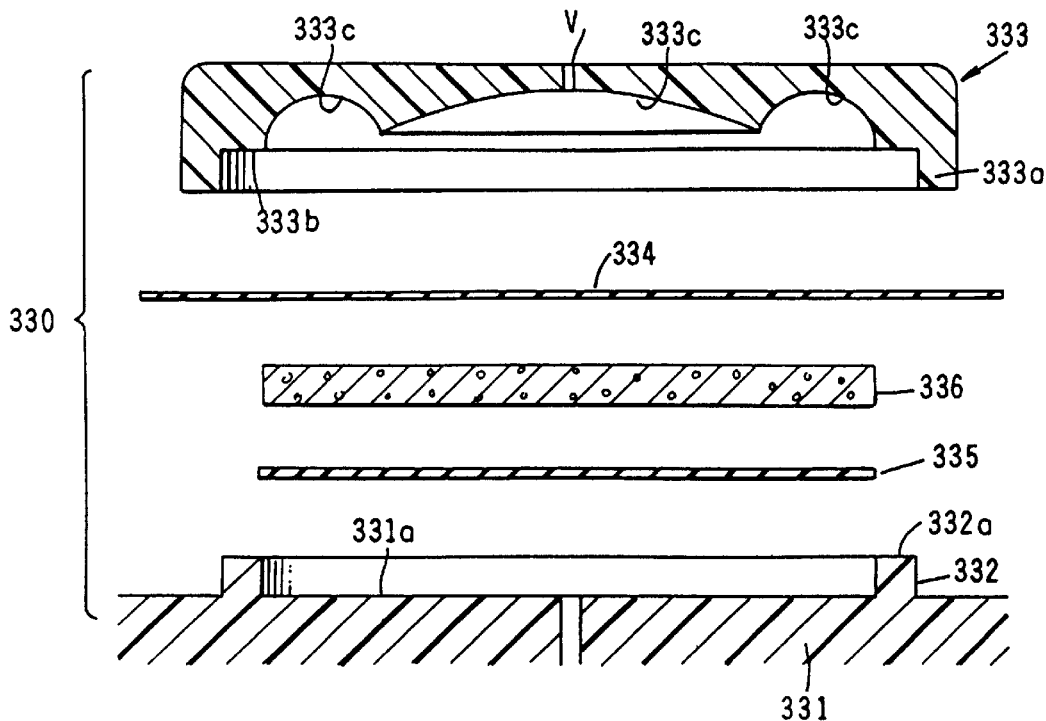
FIG. 35 is a cross-sectional, exploded view of an alternate form of the reservoir assembly of the apparatus of the invention.
Figure 36:
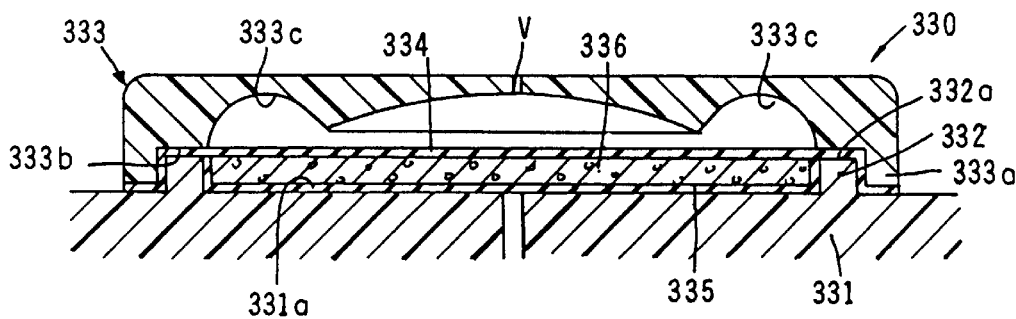
FIG. 36 is a cross-sectional view of the reservoir assembly shown in FIG. 35 as it appears in an assembled, unfilled configuration.
Figure 37:
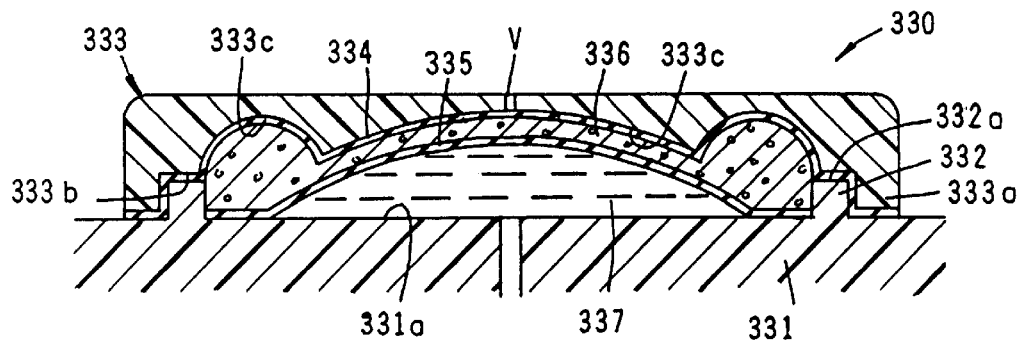
FIG. 37 is a cross-sectional view similar to FIG. 36 but showing the reservoir assembly in a filled configuration.

Referring now to FIGS. 35, 36, and 37, still another form of reservoir assembly of the invention is there shown and generally designated by the numeral 330. This reservoir assembly or unit also mates with the base of the fluid delivery device in a slightly different manner. More particularly, as best seen in FIG. 35, the base 331 of the fluid delivery device of this alternate form of the invention is provided with an upstanding, generally ring-shaped protuberance 332 over which a skirt portion 333a of a strategically shaped cover member 333 is closely received (FIG. 36). With this construction, a distendable membrane 334 is sealably clamped between an internal shoulder 333b formed on the cover member and the upper surface 332a of ring-shaped protuberance 332.

A barrier membrane 335 extends over the upper surface 331a of base 331 and is suitably affixed thereto about its periphery as by adhesive or thermal bonding in the manner shown in FIGS. 36 and 37. Disposed between distendable membrane 334 and barrier membrane 335 is a conformable ullage defining means here shown as a soft elastomer 336.

In operation, as the fluid under pressure flows into the reservoir 337, which is defined by the lower surface of the barrier membrane and the upper surface 331a of the base 331, barrier member 335 will be distended outwardly from the position shown in FIG. 36 to the position shown in FIG. 37 and will uniformly deform the conformable ullage means or elastomer 336. as elastomer 336 moves outwardly from the upper surface of the base, the distendable membrane 334 will distend outwardly until it reaches the position shown in FIG. 37 and engages the inner surfaces 333c. Gases contained in the volume between the cover subassembly and distendable membrane 334 will be vented to atmosphere via vent passageway "V" (FIG. 35). As before, the entire reservoir assembly can be assembled as a unit with base 331 and will function in the same manner as previously described.

Figure 38:
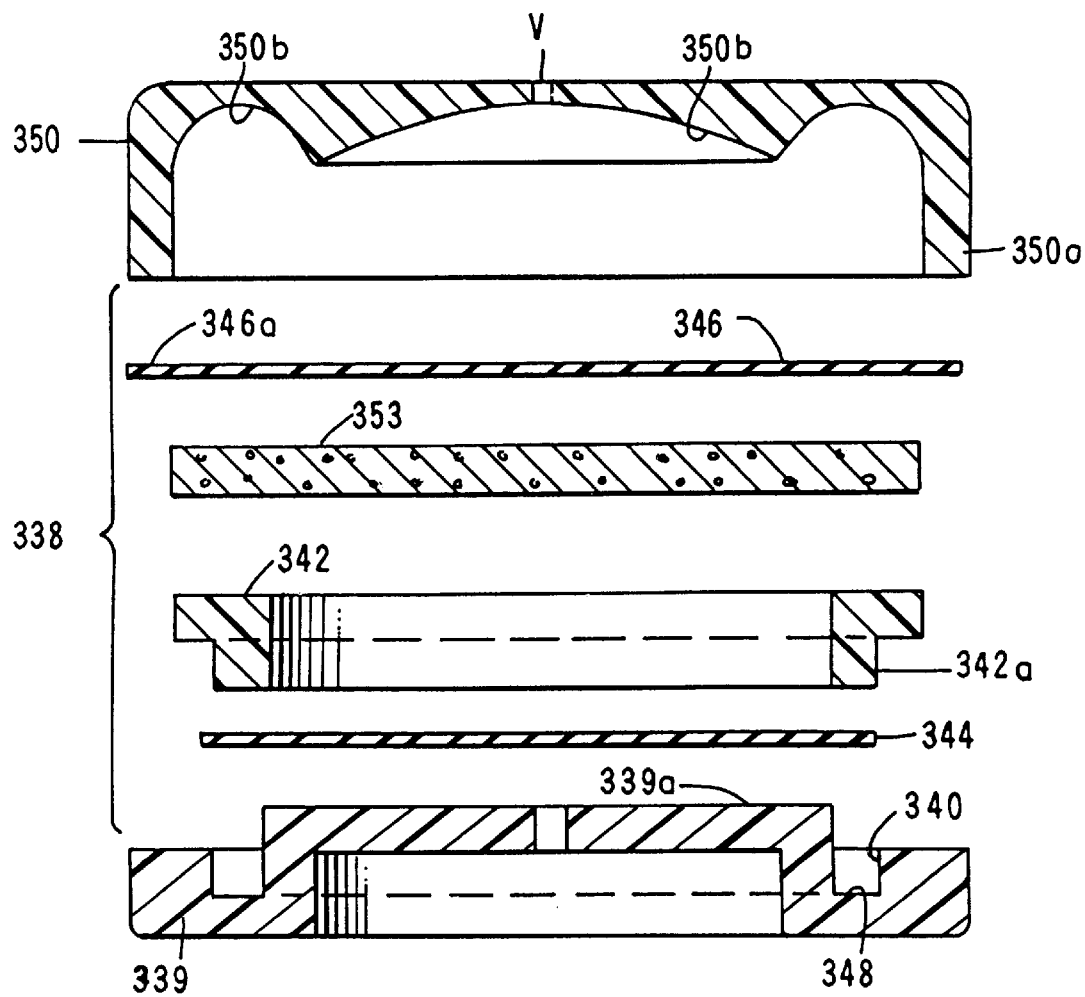
FIG. 38 is a cross-sectional, exploded view of still another form of the reservoir assembly of the apparatus of the invention.

Turning next to FIGS. 38 through 39, still another form of reservoir assembly is there shown and generally designated by the numeral 338. This reservoir assembly or unit is somewhat similar to that shown in FIG. 15 save that the base 336 of the fluid delivery device of this alternate form of the invention includes a bottom housing 339 (FIG. 38) which includes circular shaped central portion 339a which is circumscribed by a groove 340. Sealably receivable within groove 340 is a skirt portion 342a which is provided on a strategically shaped membrane retaining ring 342 (FIG. 38). With this construction, a barrier membrane 344 is sealably clamped between retaining ring 342 and the upper surface 348 of ring-shaped groove 340 formed in housing 339.

Figure 40:
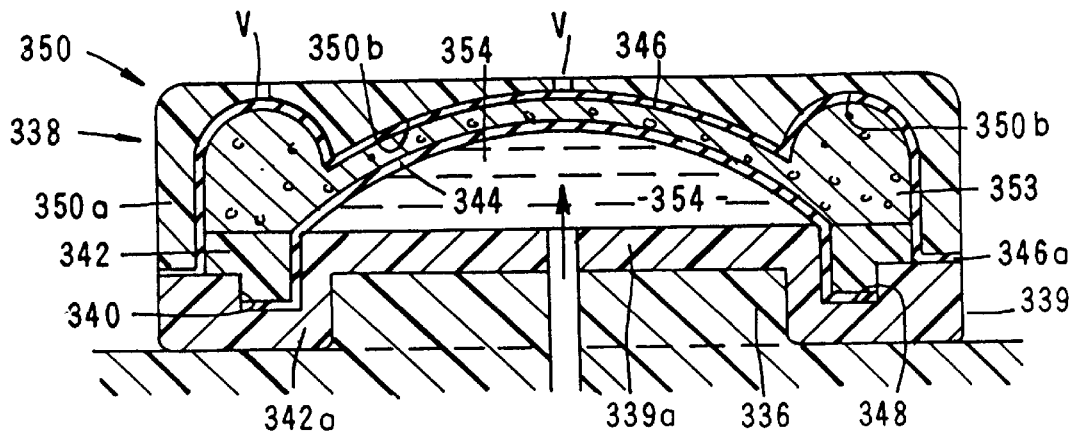
FIG. 40 is a cross-sectional view similar to FIG. 39, but showing the reservoir assembly in a filled configuration.

A distendable membrane 346 extends over retaining ring 342 and is sealably connected thereto about its periphery 346a by a downwardly depending skirt 350a formed on a cover member 350 (FIGS. 39 and 40). Disposed between the distendable membrane 346 and barrier membrane 344 is a conformable ullage defining means here shown as a deformable foam 353.

In operation, as the fluid under pressure flows into the reservoir 354, which is defined by the lower surface of the barrier membrane and the upper surface of housing 339, barrier member 344 will be distended outwardly from the position shown in FIG. 39 to the position shown in FIG. 40 and will uniformly deform the conformable ullage means or foam 353. As foam 353 moves outwardly from the upper surface of housing 339, the distendable membrane 346 will distend outwardly until it reaches the position shown in FIG. 40 where it engages the inner wall 350b of cover 350. Gases contained in the volume between the cover and distendable membrane 346 will be vented to atmosphere via vent passageway "V". As before, the entire reservoir assembly can be assembled as a unit and will function in the same manner as previously described.

It is apparent from the foregoing discussion and from an analysis of FIGS. 24 and 32 through 40, that a number of different types of reservoir assemblies can be operably coupled with a base assembly 277 of the character shown in FIG. 25. More particularly, by selecting the proper reservoir assembly, the user can choose from various types of ullage means and ullage configurations and reservoir volumes as may be best suited for the end use of the fluid delivery device. For example, the ullage means can comprise a gel, a cellular mass, an elastomer, a flowable substance or the like.

Turning next to FIGS. 41 through 48, yet another form of the apparatus of the invention is there shown. This form of the apparatus is very similar to that shown in FIGS. 24 through 40 and like numbers are used to identify like components. The major difference between this latest embodiment and that previously described resides in the sculptured appearance of the device and in the manner by which the delivery line is connected to and released from the housing. Like the apparatus shown in FIGS. 24 through 40, this latest form of the apparatus of the invention is also designed to be a free standing unit which can be carried by the patient or attached to the patient's clothing.

Referring particularly to FIGS. 41, 45, and 46, the fluid delivery assembly portion of the apparatus can be seen to include a base subassembly 360, including an end portion 360a (FIG. 47), a cover subassembly 362, which is receivable over base subassembly 360, and a stored energy means, here provided in the form of a distendable membrane 364 (FIG. 45) As before, distendable membrane 364, in cooperation with a barrier member 366, functions to encapsulate the ullage defining means of this form of the invention for providing a conformable ullage, which is of the character previously described.

Like the earlier described embodiments of the invention, this latest embodiment also includes a novel bolus delivery means of the general character previously described for delivering bolus doses of medication to the patient. As before, the bolus delivery means includes operating means for accomplishing closely controlled fluid flow through the outlet of the fluid delivery assembly. The operating means of this latest form of the invention is virtually identical in construction and operation to that previously described herein save for the addition of an idler gear assembly 367 (FIG. 41) and like numbers have been used in FIGS. 41 through 48 to identify like components of this important bolus delivery means.

As best seen in FIG. 41 an elongated receiving chamber 368 is provided between base subassembly 360 and cover assembly 362 and is adapted to receive a portion of the fill subassembly of the invention. Once again, the fill assembly of the invention is identical to that shown in FIGS. 11 and 12 and includes a container subassembly 133, an adapter subassembly 135, and a cover assembly of the character shown in FIG. 11 and designated by the numeral 137 all of which are of the same construction and operate in the same manner as previously described herein. As indicated in FIG. 41, the fluid chamber 141 of container 139 of the fill subassembly communicates via passageways 370, 372 and 374 with the fluid reservoir 376 (FIG. 42) of the fluid delivery assembly, which reservoir is uniquely formed between deform-able barrier member 366 and the upper surface 378a of a base member 378 which forms a part of base subassembly 360. As previously mentioned, disposed between barrier member 366 and distendable membrane 364 is the important conformable ullage means of this latest form of the invention which is similar in many respects to that described in connection with FIGS. 14 through 17.

Passageway 370, which is formed within hollow piercing cannula 220 communicates with passageway 372 which, in turn, communicates with passageway 374 that terminates in inlet 380 of reservoir 376. Passageway 372 also communicates via a porous plug 382 with a continuation passageway 372a which, in turn, communicates with the outlet port 384 of the fluid delivery assembly. As before, outlet port 384 includes a tapered wall portion 384a which sealably receives the tapered portion of the quick connect coupler assembly 260 which is of the same general character previously described and which comprises a part of the fluid delivery means of the invention. As best seen in FIG. 41, continuation passageway 372a also communicates with an outlet passageway 388 which leads to the outlet port 389 of fluid reservoir 376.

Save for the design of the control means and the manner of interconnection and release of the delivery line assembly, the apparatus operates in substantially the same manner as the apparatus shown in FIGS. 24 through 40. More specifically, the control means here comprises the previously identified indexing disc 198 and also includes a safety interlocking means for controlling rotation of indexing disc 198. This interlocking means here comprises a push-button, activated locking means which comprises an engagement arm 391 which, as best seen in FIG. 41, includes an end portion 391a, which is receivable in a selected one of four circumferentially spaced slots 256 provided in control wheel 198, which slots are here spaced apart 90 degrees. With this construction, so long as end portion 391a of the engagement arm is received within one of the slots 256, rotation of indexing disc 198 as well as rotation of the finger engaging or thumb wheel 192 of the apparatus is effectively prevented. However, upon inward movement of the push button 393 and the engagement arm connected thereto against the urging of a biasing means, here provided as a coil spring 395, rotation of disc 198 and wheel 192 is made possible (see FIG. 41).

As before, as wheel 192 is rotated, wheel 190 will engage and rotate an idler gear 367 and the screw gear 184 which, in turn, will rotate drive wheel 180 causing an incrementally controlled, telescopically inward movement of adapter assembly 153 into receiving chamber 368. In this way the volume of the fluid F1 remaining within chamber 141 can be precisely incrementally displaced from the chamber by closely controlling the extent of rotation of control wheel 198.

In operating the device of this latest form of the invention, the fluid containing portion of the fill assembly is mated with the device in the manner previously described and the reservoir is filled in the manner previously described. Similarly, bolus injections are accomplished using the operating means, which means is substantially identical in construction and operation to that shown in FIGS. 24 through 40.

Turning particularly to FIGS. 47 and 48, the novel delivery line interconnection and release means of the invention for interconnecting the delivery assembly shown in FIG. 17A to the apparatus housing is there shown. This means here comprises a push button subassembly 390 which includes a head portion 390a and a pair of yieldably deformable legs 392. A part of head portion 390a extends through an aperture 394a formed in cover 394 of the cover subassembly 362 in the manner shown in FIG. 47 so that the depending legs 392 engage the ramp sides 396a and 396b of a ramp unit 396 (FIG. 48). Ramp unit 396 is connected to the base subassembly as shown in FIG. 47 at a location proximate outlet port 384. Each of the legs 392 of the push button subassembly is provided with a locking protuberance 398 which is constructed and arranged to lockably engage the shoulder 397 of the delivery fitting (FIG. 44B) when the push button subassembly is in the upward, at-rest position shown in FIG. 47. It is apparent that a downward force of head portion 390 as shown in FIG. 47A will cause legs 392 to move downwardly along ramp sides 396a and 396b causing protuberance 398 to spread apart a sufficient distance to permit withdrawal of delivery fitting. As best seen in FIG. 44A, the fitting 399 is similar to fitting 260 save for the fact that shoulder 397 replaces wings 266 of the earlier described fitting assembly.

Turning next to FIGS. 49 through 58, another embodiment of the invention is there shown. This form of the apparatus is somewhat similar to that shown in FIGS. 24 through 40 and like numbers are used to identify like components. The major difference between this latest embodiment and those previously described herein resides in the fact that the apparatus here comprises dual fill assemblies, one for use in filling the reservoir of the fluid delivery assembly and the other for providing a bolus dose of beneficial agent as may be required. Like the apparatus shown in FIGS. 24 through 40, this latest form of the apparatus of the invention is a free standing unit which can be carried by the patient or, for example, attached to the patient's belt.

Figure 53:
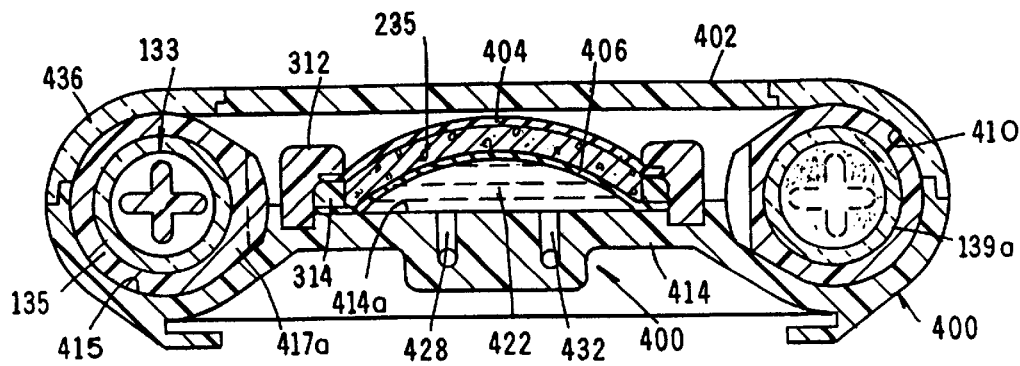
FIG. 53 is a cross-sectional view taken along lines 53—53 of FIG. 49.
Figure 54:
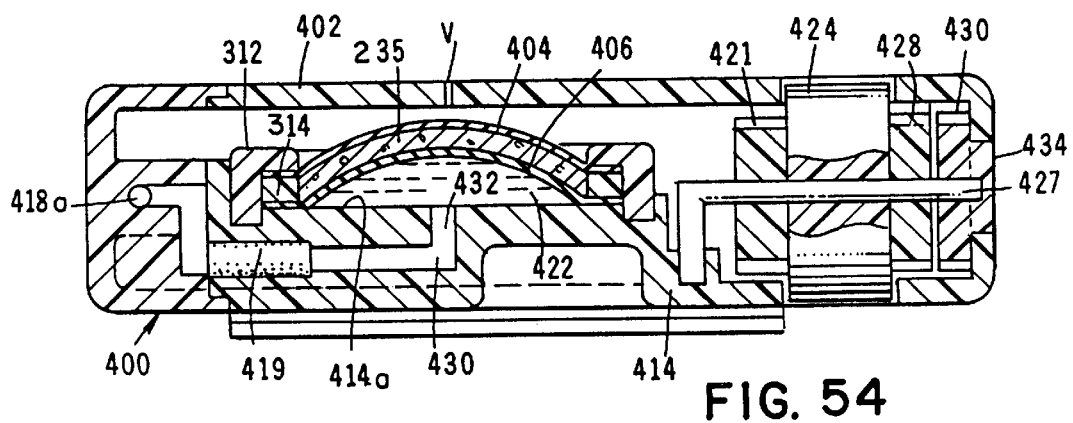
FIG. 54 is a cross-sectional view taken along lines 54—54 of FIG. 49.
Figure 55:
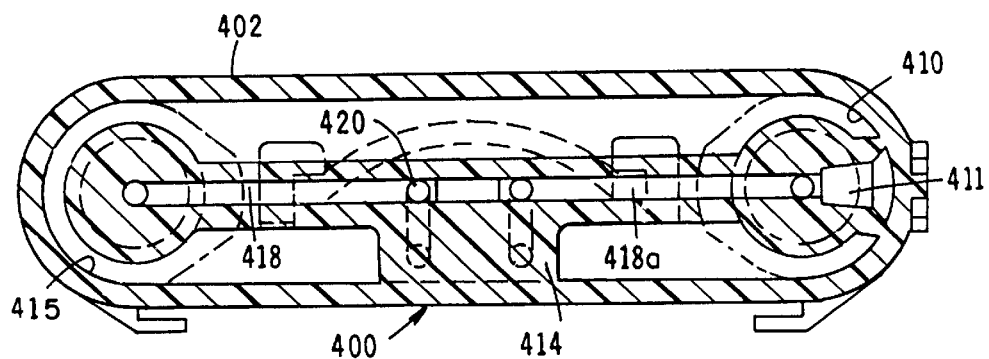
FIG. 55 is a cross-sectional view taken along lines 55—55 of FIG. 49.

Referring particularly to FIGS. 49, 53, and 54, the fluid delivery assembly portion of the apparatus can be seen to include a base subassembly 400, a cover subassembly 402, which is receivable over base subassembly 400, and a stored energy means, here provided in the form of a distendable membrane 404 (FIG. 53). Distendable membrane 404, in cooperation with a barrier member 406, functions to encapsulate the ullage defining means of this form of the invention for providing a conformable ullage, which is of the character previously described.

Unlike the earlier described embodiments of the invention, this latest embodiment includes a first fill assembly for filling the reservoir of the device and a separate bolus delivery means for delivering bolus doses of medication to the patient. The bolus delivery means here comprises a second fill assembly and, as before, includes operating means for accomplishing closely controlled fluid flow through the outlet of the fluid delivery assembly via a second hollow cannula 408 which extends into a second receiving chamber 410 formed in the delivery assembly portion of the apparatus. The operating means of this latest form of the invention is very similar in construction and operation to that described in connection with the apparatus shown in FIGS. 24 through 40.

More particularly, as best seen in FIG. 49, the operating means here comprises driving means, including a drive wheel 412, which is rotatably carried by base member 414 of the base assembly of this latest embodiment. The operating means further includes driven means, which here comprises a plurality of longitudinally spaced-apart, teeth-like portions 417 provided on a second hollow housing 417a of the second fill assembly which is of identical construction to that shown in FIG. 11 save that the second hollow housing is provided with additional teeth-like portions. Drive wheel 412 along with a first screw gear 418 are mounted on a first shaft 421 which is carried by spaced-apart shaft supports formed on base member 414. Screw gear 419 along with drive wheel 412 are driven by a second screw gear 423, which along with a finger engaging or thumb wheel 424, is mounted on a second shaft 427 which is rotatably supported by supports similar to supports 195 of the character shown in FIG. 15 (see also FIG. 54).

Also carried by second shaft 427 is an anti-reverse rotation gear 429, an indexing disc 431, and an indicator disc 434 (FIG. 49) which performs the same function respectively as anti-rotation gear 196, indexing disc 198 and indicator disc 200. Indexing disc 430 and indicator disc 434 comprise a part of the control means of this latest form of the invention for controlling bolus flow outwardly of the device as a result of the controlled advancement of hollow housing 418a within receiving chamber 410 (FIG. 49).

Second receiving chamber 410, which is adapted to receive a portion of the second fill subassembly of the invention, is strategically located between base 400 and a cover member 402 which comprises a part of the cover subassembly. When the components are in the position shown in FIG. 49, the fluid chamber 141a of a second container 139a of the second fill subassembly communicates via second hollow cannula 408 with the fluid delivery means of the apparatus, which includes the outlet port 411 of the apparatus.

As best seen in FIG. 49 another elongated receiving chamber 415 is provided between base subassembly 400 and cover subassembly 402 and is adapted to receive a portion of the first fill subassembly of the invention which is identical to the previously described fill subassembly 127 (see FIG. 11). First fill assembly includes a container subassembly 133, an adapter subassembly 135, and a cover assembly 137 all of which are of the same construction and operate in the same manner as previously described herein. As indicated in FIG. 49, the fluid chamber 141 of first container 139 of the first fill subassembly communicates via passageways 416, 418 and 420 with a fluid reservoir 422 of the fluid delivery assembly. Reservoir 422 is formed between deformable barrier member 406 and the upper surface 414a of a base member 414 which forms a part of base subassembly 400 (FIGS. 53 and 54). In the manner previously discussed the important conformable ullage means of the invention is disposed between barrier member 406 and distendable membrane 404.

Passageway 416, which is formed within a first hollow piercing cannula 426 communicates with passageway 418 which, in turn, communicates with passageway 420 that terminates in an inlet 428 of reservoir 422. Passageway 418 also communicates with a continuation passageway 418a via reservoir 422 which, in turn, communicates with the outlet port 411 of the fluid delivery assembly. As before, outlet port 411 includes a tapered wall portion 411a which sealably receives the tapered portion of the quick connect coupler assembly 399 which is of the character previously described and which comprises a part of the fluid delivery means of the invention. As best seen in FIG. 49, a continuation passageway 418a also communicates with an outlet passageway 430 which leads to the outlet port 432 of fluid reservoir 422. Interconnection and release of the delivery line assembly shown in FIG. 17A is accomplished in the exact manner as was the case with the apparatus shown in FIGS. 24 and 40.

In using the apparatus of this latest form of the invention, with the first fill assembly in the filled configuration shown in FIG. 12, the cover subassembly 137 is first removed from the container subassembly to expose the forward portion of the container subassembly and first septum 147. This step readies the first adapter subassembly for interconnection with the fluid delivery assembly of the invention in the manner shown in FIG. 49.

In mating the first adapter subassembly with the fluid delivery assembly, the first container subassembly is first telescopically inserted into first receiving chamber 415 of the subassembly of the invention which is identical to the previously described fill subassembly 127 (see FIG. 11). First fill assembly includes a container subassembly 133, an adapter subassembly 135, and a cover assembly 137 all of which are of the same construction and operate in the same manner as previously described herein. As indicated in FIG. 49, the fluid chamber 141 of first container 139 of the first fill subassembly communicates via passageways 416, 418 and 420 with a fluid reservoir 422 of the fluid delivery assembly. Reservoir 422 is formed between deformable barrier member 406 and the upper surface 414a of a base member 414 which forms a part of base subassembly 400 (FIGS. 53 and 54). In the manner previously discussed the important conformable ullage means of the invention is disposed between barrier member 406 and distendable membrane 404.

Passageway 416, which is formed within a first hollow piercing cannula 426 communicates with passageway 418 which, in turn, communicates with passageway 420 that terminates in an inlet 428 of reservoir 422. Passageway 418 also communicates with a continuation passageway 418a via reservoir 422 which, in turn, communicates with the outlet port 410 of the fluid delivery assembly. As before, outlet port 411 includes a tapered wall portion 411a which sealably receives the tapered portion of the quick connect coupler assembly 260 which is of the character previously described and which comprises a part of the fluid delivery means of the invention. As best seen in FIG. 49, a continuation passageway 418a also communicates with an outlet passageway 430 which leads to the outlet port 432 of fluid reservoir 422. Interconnection and release of the delivery line assembly shown in FIG. 17A is accomplished in the exact manner as was the case with the apparatus shown in FIGS. 24 and 40.

In operating this latest form of the invention, with the first fill assembly in the filled configuration shown in FIG. 12, and with the cover subassembly 137 removed the assembly is inserted into receiving chamber 414 and pushed forwardly to the position shown in FIG. 49. The pushing force exerted on the first adapter subassembly will cause first piercing cannula 426, which extends into receiving chamber 414, to pierce first septum 147. Once a fluid flow path between fluid chamber 141 of the container subassembly and the fluid reservoir 422 of the fluid delivery assembly is thus created, a continued movement of the first adapter subassembly toward the position shown in FIG. 49 will cause pusher rod 159 to move plunger 129 forwardly of chamber 141. As plunger 129 is moved forwardly of chamber 141, substantially all of the fluid "F" contained within the chamber will flow into passageway 416 of the first piercing cannula, into passageway 418, into passageway 420 and then into fluid reservoir 422 via inlet 428. As the fluid under pressure flows into reservoir 422, barrier member 406 will be distended outwardly in the manner shown in FIG. 53 and will uniformly deform the conformable ullage means, shown here as a gel 235. As gel 235 moves outwardly from surface 414a, the distendable membrane 404 will distend outwardly until it reaches the position shown in FIG. 53. Gases contained in the volume between the cover subassembly 402 and distendable membrane 404 will be vented to atmosphere via vent passageway "V" (FIG. 54). As before, a retaining ring 314 functions to capture and seal the distendable membrane about its periphery. In a similar manner, the periphery of the barrier member 406 is sealably clamped to base 414 by clamping ring 314 so as to prevent leakage of fluid around the periphery of the member (see also FIG. 34).

With the construction described in the preceding paragraphs, the conformable gel, which comprises the ullage defining means of this form of the invention is disposed within a chamber defined by the upper surface of the barrier membrane 406 and the inner surfaces of base 414 and retaining ring 314. As indicated in FIGS. 53 and 54, the ullage or gel 235 is in direct contact with distendable membrane 404 which, after being distended, will tend to return to its less distended configuration. It is to be noted that the shape of the conformable ullage will continuously vary as the distendable membrane distends outwardly from the base during reservoir filling and then as it tends to return to its less distended configuration during the basal fluid delivery step.

Once reservoir 422 is filled with fluid from the first container subassembly of the first fill assembly, designated in FIG. 49 as 433, the fluid will remain in the reservoir until such time as the outlet flow path of the fluid delivery assembly is opened to fluid flow. Once the outlet flow path of the assembly is opened, distendable membrane 404 will tend to return to its less distended configuration and will act upon the conformable ullage and the barrier member 406 in a manner to cause fluid to flow from reservoir 422 outwardly through a reservoir outlet 432. The fluid will next flow into passageway 418a via a rate control element 419 and finally outwardly of the device via the fluid delivery means of the apparatus.

Considering once again the bolus delivery means of the apparatus of this latest form of the invention, this novel means enables the patient to receive a selected basal dose of medication from reservoir 422 and also a bolus dose of medication from chamber 141a of second container 135a of the portion of the fill assembly designated as 435 in FIG. 49.

More particularly, after the second adapter subassembly 135a of the second fill assembly portion has been mated with the fluid delivery assembly by insertion of the vial assembly and adapter assembly into receiving chamber 410 (FIG. 58), bolus delivery can be accomplished by operation of the operating means of the invention and, more particularly, by rotation of the finger engaging means, or thumb wheel 424, of the operating means of the invention. As previously discussed, rotation of thumb wheel 424 will impart rotation to first screw gear 418 and also to drive wheel 412. Rotation of drive wheel 412 of the drive means relative to adapter housing 417a will cause the controlled advancment of the second adapter assembly into receiving chamber 410. As the second adapter assembly is thus moved incrementally inwardly of receiving chamber 410, second plunger 129a will move incrementally forwardly of second chamber 141a causing the fluid F3 contained within chamber 141a to be expelled outwardly of the chamber via second hollow cannula 408 and delivery passageway 418a.

An important feature of the fluid delivery assembly of this latest form of the invention comprises the previously mentioned control means for controlling the rotation of drive wheel 412 and thereby controlling the bolus volume flowing from portion 435 of the apparatus via outlet port 411. This novel control means, which forms a part of the operating means of the invention, is similar to that described in connection with the embodiment shown in FIG. 14 and includes the previously identified indicator disc 200 and an indexing disc 430. Also forming a part of the control means of this latest form of the invention is safety interlocking means for controlling rotation of indexing disc 430. This interlocking means here comprises a push button assembly 431 which includes a locking member 431a (FIG. 56). The control means operates in substantially the same manner as previously discussed herein and the details of operation will not be here repeated.

Turning to FIGS. 59 through 78, still another form of the apparatus of the invention is there shown. This form of the apparatus is similar to that shown in FIGS. 41 through 48 and like numbers are used to identify like components. This embodiment, like that of FIGS. 41 through 48, has a sleek sculptured appearance and is also designed to be a free standing unit which can be carried by the patient or attached to the patient's clothing.

Figure 64:
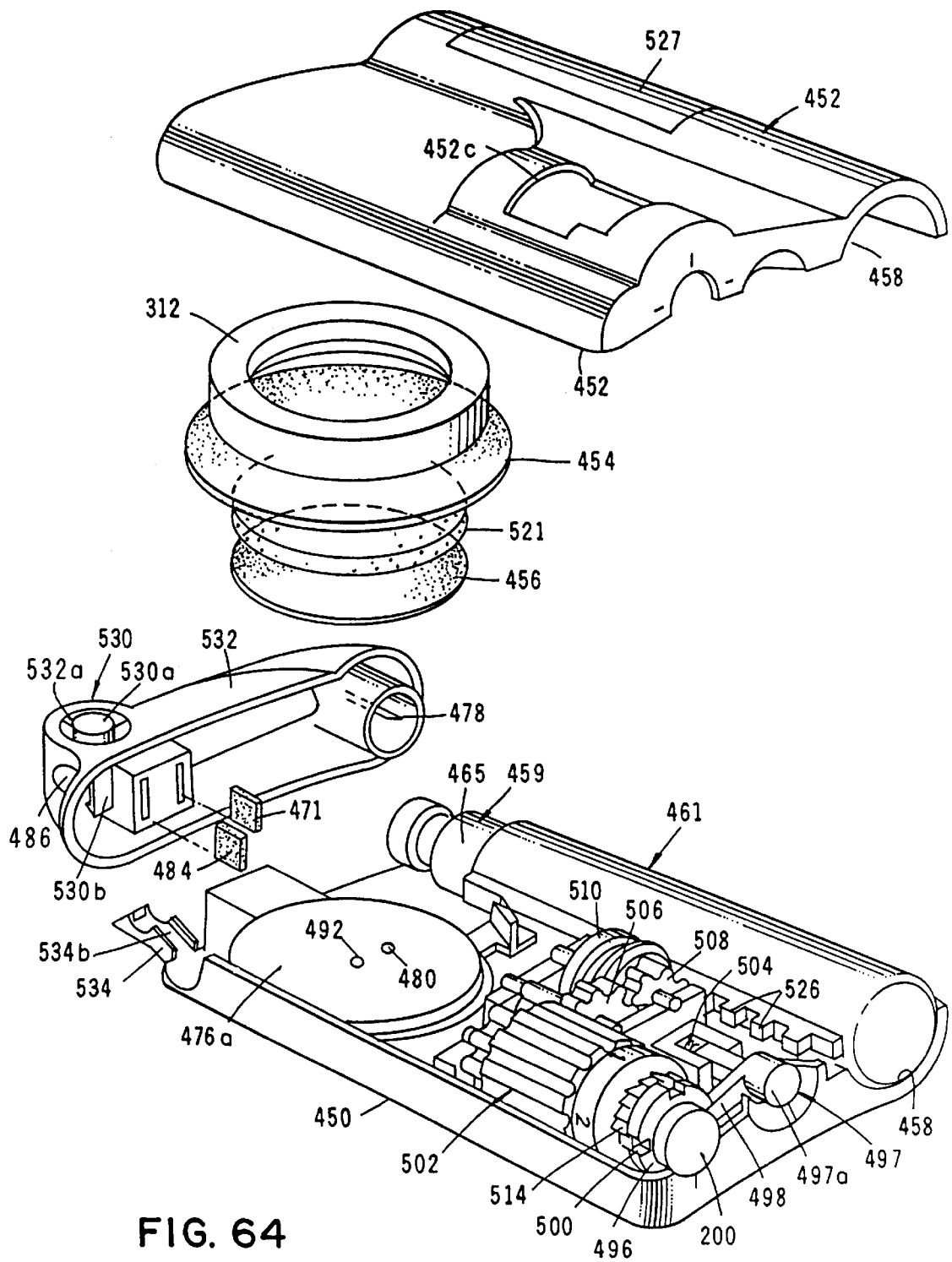
FIG. 64 is a generally perspective exploded view of the apparatus of the invention shown in FIG. 60.
Figure 68:
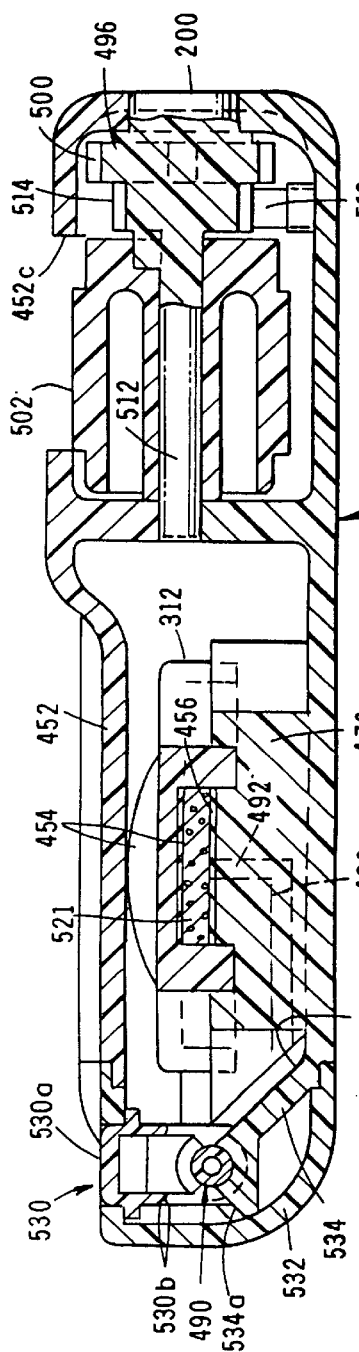
FIG. 68 is a cross-sectional view taken along lines 68—68 of FIG. 66.
Figure 69:
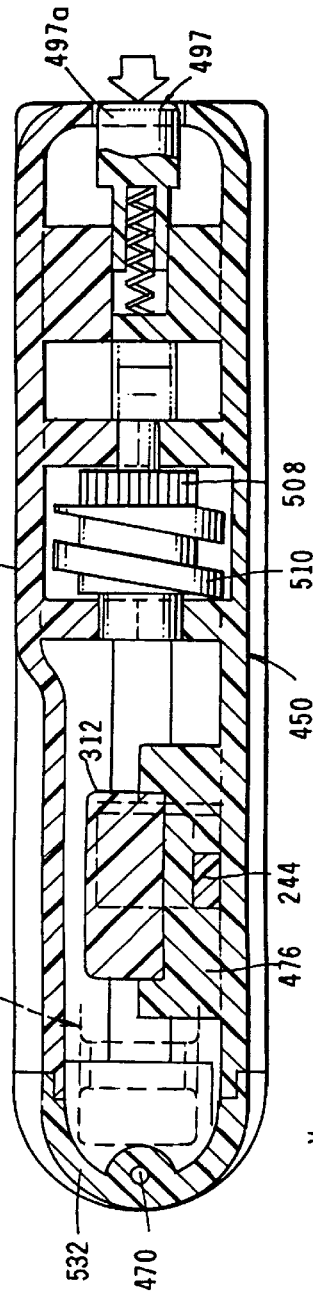
FIG. 69 is a cross-sectional view taken along lines 69—69 of FIG. 66.
Figure 70:
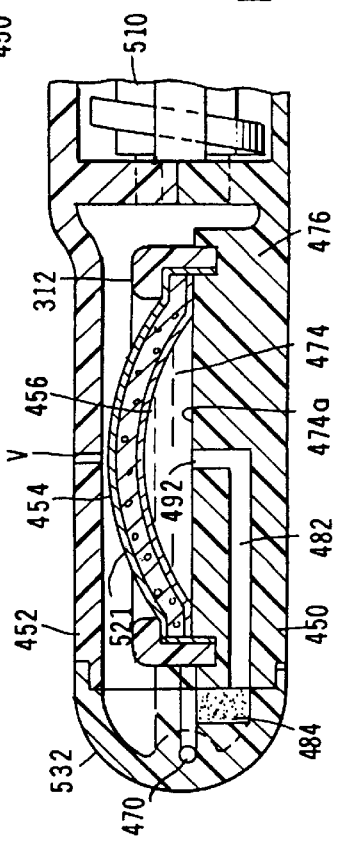
FIG. 70 is a cross-sectional view taken along lines 70—70 of FIG. 66.
Figure 75:
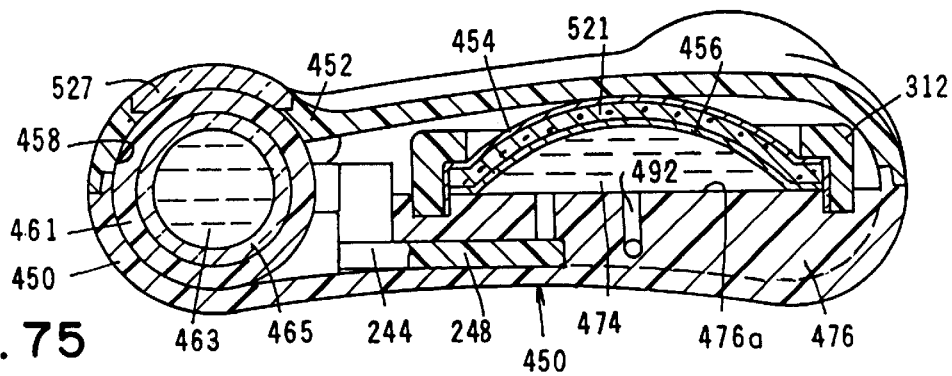
FIG. 75 is a cross-sectional view taken along lines 75—75 of FIG. 66.
Figure 76:
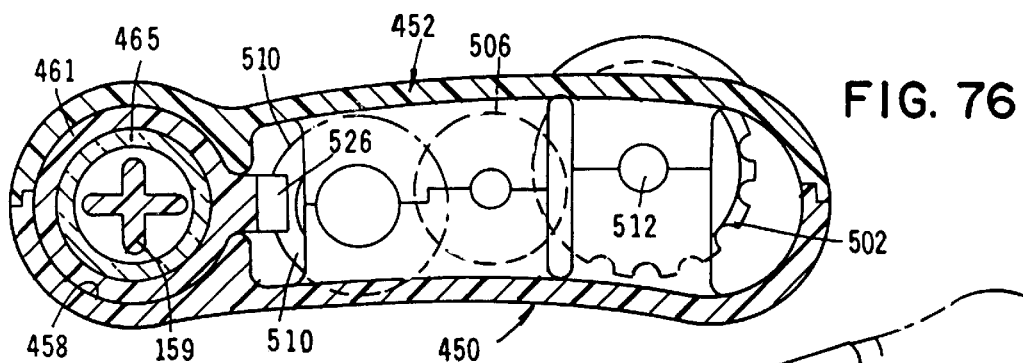
FIG. 76 is a cross-sectional view taken along lines 76—76 of FIG. 66.
Figure 77:
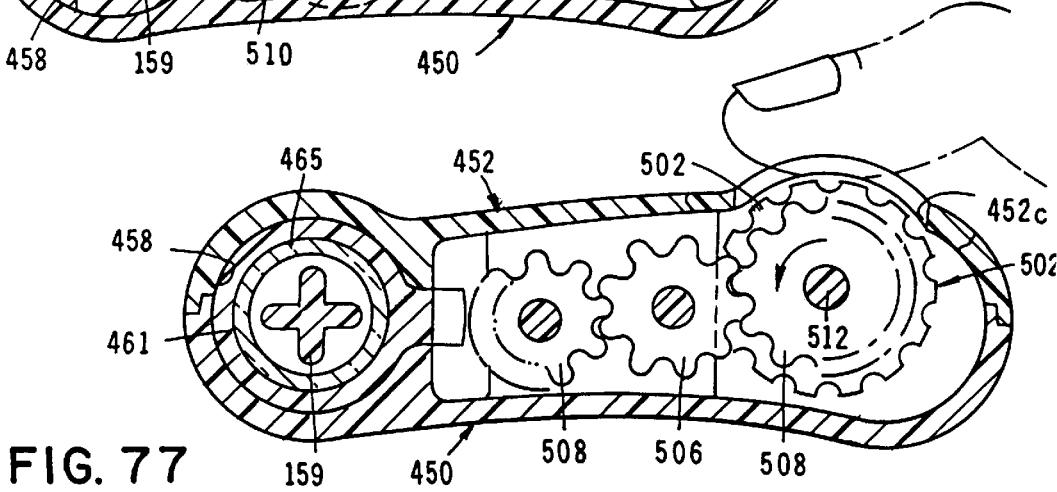
FIG. 77 is a cross-sectional view taken along lines 77—77 of FIG. 66.

Referring particularly to FIGS. 49 through 64, the fluid delivery assembly portion of the apparatus can be seen to include a base subassembly 450, a cover subassembly 452, which is receivable over base subassembly 450, and a stored energy means, here provided in the form of a distendable membrane 454 (FIGS. 64 and 70). As before, distendable membrane 454, in cooperation with a barrier member 456, functions to encapsulate the ullage defining means of this form of the invention for providing a conformable ullage, which is of the character previously described.

Like the earlier described embodiments of the invention, this latest embodiment also includes a novel bolus delivery means of the general character previously described for delivering bolus doses of medication to the patient. As before, the bolus delivery means includes operating means for accomplishing closely controlled fluid flow through the outlet of the fluid delivery assembly. As best seen in FIGS. 64 and 65, the operating means of this latest form of the invention is similar in construction and operation to that previously described and like numbers have been used in FIGS. 59 through 78 to identify like components.

An elongated receiving chamber 458 is provided between base subassembly 450 and cover subassembly 452 and is adapted to receive a portion of the fill subassembly of the invention. Once again, the fill assembly of the invention is similar to that shown in FIGS. 11 and 12 and includes a container subassembly 459, an adapter subassembly 461, and a cover subassembly 137 all of which operate in a similar manner to that previously described herein. As indicated in FIG. 66, the fluid chamber 463 of container 465 of the fill subassembly communicates via passageways 468, 470 and 472 with the fluid reservoir 474 (FIG. 70) of the fluid delivery assembly, which reservoir is uniquely formed between deformable barrier member 456 and the upper surface 476a of a base member 476 which forms a part of base subassembly 450. As previously mentioned, disposed between barrier member 456 and distendable membrane 454 is the important conformable ullage means of this latest form of the invention which is similar in many respects to that described in connection with FIGS. 49 through 58.

Passageway 468, which is formed within a hollow piercing cannula 478 communicates with passageway 470 which, in turn, communicates, via a porous member 471, with passageway 472 that terminates in inlet 480 of reservoir 474. As shown in FIGS. 66 and 70, reservoir 474 also communicates with an outlet port 492 via a passageway 482 and a rate control means shown here as a second porous wafer 484. Porous members 471 and 484 can be constructed of various porous sintered materials such as ceramics, stainless steel and other metals having fluid flow passage of a desired size to closely control the flow of fluid therethrough. As before, outlet port 486, which comprises the outlet of the fluid delivery assembly, includes a tapered wall portion 488 which sealably receives the tapered portion 490a of a quick connect coupler assembly 490 which is of the same general character previously described and which comprises a part of the fluid delivery means of the invention. As best seen in FIG. 66, passageway 482 communicates with the outlet port 492 of fluid reservoir 474.

Figure 78:
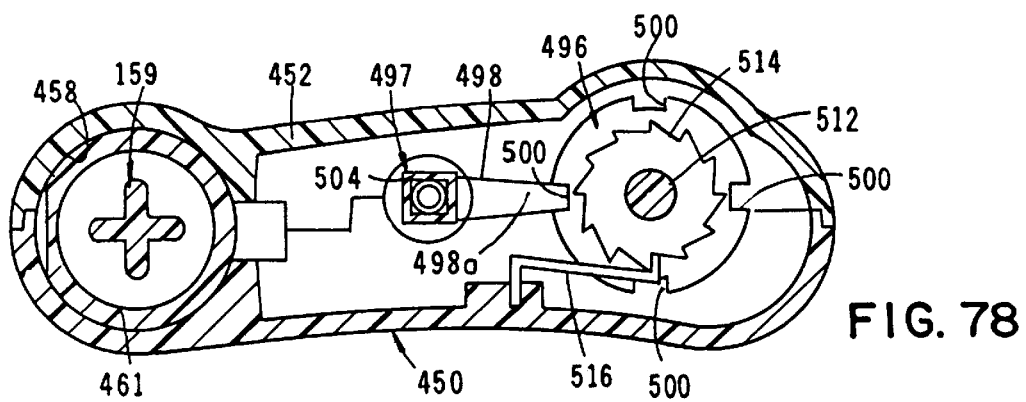
FIG. 78 is a cross-sectional view taken along lines 78—78 of FIG. 66.

As best seen in FIGS. 64 and 65, the control means of this latest form of the invention comprises an indexing disc 496 and also includes a safety interlocking means for controlling rotation of indexing disc 496. This interlocking means here comprises a push-button, activated locking means, or locking assembly 497, which includes an engagement arm 498 which, as best seen in FIG. 78, includes an end portion 498a, which is receivable in a selected one of four circumferentially spaced slots 500 provided in disc 496, which slots are here spaced apart 90 degrees. With this construction, so long as end portion 498a of the engagement arm is received within one of the slots 500, rotation of indexing disc 496 as well as rotation of the finger engaging or thumb wheel 502 of the apparatus is effectively prevented. However, upon inward movement of the push button 497a of the locking assembly and the engagement arm connected thereto against the urging of a biasing means, here provided as a coil spring 504, rotation of disc 496 and wheel 502 is made possible.

As thumb wheel 502 is rotated, it will engage and rotate wheel 506, which will engage and rotate a gear 508. In turn, gear 508 will rotate a drive wheel 510, which cooperates with teeth 526 provided on adapter assembly 461 to cause an incrementally controlled, telescopically inward movement of the adapter assembly into receiving chamber 458. In this way the volume of the fluid remaining within chamber 463 can be precisely, incrementally displaced and thereby dispensed from the chamber by closely controlling the amount of rotation of the control or thumb wheel 502 which is carried by a shaft 512. Shaft 512 also carries means for preventing reverse rotation to wheel 514, which includes a tooth engaging, resiliently deformable locking clip 516 that is mounted on base assembly 450 (see FIGS. 64, 65 and 78). When clip 516 is in the position shown in FIG. 78, rotation of wheel 514 in a counter-clockwise, reverse direction is prevented, but rotation in the opposite direction is permitted.

In operating the device of this latest form of the invention, the fluid containing portion of the fill assembly is mated with the device in the manner previously described. More particularly, after the adapter subassembly has been inserted into receiving chamber 458, it is pushed forwardly in the direction of the arrow "P" of FIG. 66. The pushing force exerted on the adapter subassembly will cause piercing cannula 478, which extends into receiving chamber 458, to pierce septum 147 in the manner shown in FIG. 71. Once a fluid flow path between fluid chamber 463 of the container subassembly and the fluid reservoir 474 of the fluid delivery assembly is thus created, a continued inward movement of the adapter subassembly will cause pusher rod 159 to move plunger 129 forwardly of chamber 463 to the position shown in FIG. 66. As plunger 129 is moved forwardly of chamber 463, a portion of the fluid contained within the chamber will flow into passageway 468 of the piercing cannula, into passageway 470, into passageway 472 via porous member 471 and then into fluid reservoir 474 via inlet 480.

As the fluid under pressure flows into reservoir 474, the stored energy means will be energized. More particularly, barrier member 456 will be distended outwardly in the manner shown in FIG. 75 and will uniformly deform the conformable ullage means, shown here as a gel 521. As gel 521 moves outwardly from surface 476a, the distendable membrane 454 will distend outwardly until it reaches the position shown in FIG. 70. Gases contained in the volume between the cover and the distendable membrane will be vented to atmosphere via vent passageway "V" (FIG. 70). In the manner previously described, clamping ring 312 functions to capture and seal the distendable membrane about its periphery. In a similar manner, the periphery of the barrier member 456 is sealably affixed to base 476 as by adhesive or thermal bonding, so as to prevent leakage of fluid around the periphery of the member.

Once reservoir 474 is filled with fluid from a portion of the container subassembly of the fill assembly, valve means member 248 will extend and thereby close inlet 480 in the manner previously described. With the inlet closed, the fluid will remain in the reservoir until such time as the outlet flow path of the fluid delivery assembly is opened to fluid flow. Once the outlet flow path of the assembly is opened, the stored energy means or distendable membrane 454 will tend to return to its less energized configuration and will act upon the conformable ullage 521 and the barrier member 456 in a manner to cause fluid to flow from reservoir 474 outwardly through a reservoir outlet 492. The fluid will next flow into passageways 482 then into passageway 524, via porous member 484 and finally outwardly of the device via the fluid delivery means of the apparatus.

Considering next the extremely important bolus delivery means of the apparatus of this latest form of the invention, this novel means enables the patient to receive both a selected basal dose of medication from reservoir 474 and also a bolus dose of medication from chamber 463 of container 459. Referring particularly to FIG. 66, after the adapter subassembly 461 has been pushed forwardly into the position there shown and reservoir 474 has been filled, further forward movement of the subassembly within receiving chamber 458 is temporarily blocked by the engagement with drive wheel 510 of tooth 526a of the plurality of spaced-apart adapter teeth 526 provided on adapter assembly 466. As before, as the adapter subassembly 461 is pushed forwardly of chamber 458 in the direction of the arrow "P" of FIG. 66, an angularly inclined valve member engaging surface 242 engages the valve means of the invention which functions to control fluid flow toward fluid inlet 480 of reservoir 474. This novel valve means here comprises the previously described, inwardly extending, slidably movable operating arm 244 which has at one end a sloping camming surface 246 which is engageable by surface 242 of adapter assembly 461. Provided at the opposite end of arm 244 is a port closure member 248 which, in the manner previously described, functions to close port 480 when arm 244 is in its inward-most position. When reservoir inlet 480 is closed by the valve means, it is apparent that the fluid remaining in fluid chamber 463 is blocked from flowing into the fluid reservoir via inlet 480. However, it is important to note that upon further advancement of the adapter subassembly, the fluid that remains in fluid chamber 463, is free to flow into cannula passageway 468, into passageway 470 and then into passageway 524 via a stub connector passageway 523 (FIG. 66). In this way a controlled basal delivery of fluid to the patient can be appropriately accomplished.

To cause the fluid which remains within chamber 463 (FIG. 71) to flow outwardly of the device, the finger engaging means, or thumb wheel 502, of the operating means of the invention must be rotated. The operating means, which includes the previously discussed control means and indicator or dosing disk 200, is similar in construction and operation to that previously described herein. As before, rotation of thumb wheel 502, which extends through an opening 452c provided in cover 452, will impart rotation to gears 506 and 508 and also to drive wheel 510. Rotation of drive wheel 510 of the drive means will cause the controlled advancement of the adapter assembly from the position shown in FIG. 59 to the position shown in FIG. 60. As the adapter assembly 461 is thus moved incrementally inwardly of receiving chamber 458, plunger 129 will move incrementally forwardly of chamber 463 causing a selected bolus increment of the fluid remaining within chamber 463 to be expelled outwardly of the chamber via cannula passageway 468 and delivery passageways 470, 523 and 524. As indicated in FIG. 59, cover 452 is provided with viewing means for viewing the amount of fluid remaining in chamber 463. This viewing means here comprises a viewing window 527 having longitudinally spaced indicator lines 527a. Locking means, shown here as a locking clip 529 (FIG. 67) engages each tooth 122 of the row of locking teeth 122 provided on adapter subassembly 461 and, functions to irreversibly lock the adapter subassembly in each incrementally inserted position.

Turning particularly to FIGS. 72, 73, and 74, the novel delivery line interconnection and release means of the invention for interconnecting the delivery assembly shown in FIG. 59 to the apparatus housing is there shown. This means here comprises a push button subassembly 530 which includes a head portion 530a and a pair of yieldably deformable legs 530b. A part of head portion 530a extends through an aperture 532a formed in one end a cover assembly 532 which interconnects the top and bottom assemblies 450 and 452 in the manner illustrated in FIG. 64. With this construction, depending legs 530b of the subassembly engage the ramp sides 534a and 534b of a ramp unit 534 (FIG. 72). Ramp unit 534, which forms a part of the base subassembly 450, which is also shown in FIG. 72, is disposed at a location proximate outlet port 486. Each of the legs 530a and 530b of the push button subassembly is provided with a locking protuberance 531 which is constructed and arranged to lockably engage the shoulder 490c of the delivery fitting (FIG. 72) when the push button subassembly is in the upward, at-rest position shown in FIG. 72. It is apparent that a downward force exerted on head portion 530a will, as shown in FIG. 74, cause legs 530b to move downwardly along the ramp sides causing protuberances 531 to spread apart a sufficient distance to permit withdrawal of delivery fitting.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A fluid delivery apparatus for delivering fluid into a patient comprising:
   (a) a fluid delivery assembly having an outlet for delivering fluid from the apparatus, said fluid delivery assembly including:
      (i) a base having an upper surface, a lower surface, and a fluid passageway formed in said base intermediate said upper and lower surfaces, said fluid passageway being in communication with said outlet and having first and second ends, said lower surface of said base including means for connecting said fluid delivery assembly to the patient;

(ii) operating means for urging controlled fluid flow through said outlet, said operating means including drive means carried by said base;

(iii) a cover assembly connected to said base, one of said cover assembly and said base having a receiving chamber interconnected with said first end of said fluid passageway formed in said base; and (iv) a stored energy means comprising at least one distendable membrane superimposed over said upper surface of said base to define a fluid reservoir having a fluid inlet in communication with said fluid passageway in said base, said membrane being distendable by forces imparted thereon by fluids introduced into said reservoir through said fluid inlet, said forces establishing internal stresses within said distendable membrane, said stresses tending to return said distendable membrane toward a less distended configuration; and (b) a fluid containing subassembly interconnected with said fluid delivery assembly for filling said reservoir, said fluid containing subassembly comprising:

(i) a container assembly for containing fluid; and (ii) an adapter assembly receivable within said receiving chamber, said adapter assembly comprising a hollow housing having a first open end for telescopically receiving a part of said container of said container assembly and including a second end, said hollow housing having driven means engageable by said drive means of said fluid delivery assembly for advancing said adapter assembly within said receiving chamber.

2. A fluid delivery apparatus for infusion of beneficial agents into a patent comprising:

(a) a fluid delivery assembly having an outlet for delivering fluid from the apparatus, said fluid delivery assembly including:

(i) a base having an upper surface, a lower surface, and a fluid passageway formed in said base intermediate said upper and lower surfaces, said fluid passageway being in communication with said outlet of the apparatus and having first and second ends;

(ii) fluid reservoir defining means including a distendable membrane and a conformable ullage connected to said base for forming in conjunction therewith a reservoir having an inlet port and an outlet port in communication with said passageway formed in said base;

(iii) operating means including a drive wheel carried by said base, said operating means being operable to impart rotational movement to said drive wheel to urge fluid flow through said outlet; and (iv) a cover assembly connected to said base, one of said cover assembly and said base having a receiving chamber interconnected with said first end of said fluid passageway formed in said base; and (v) fluid delivery means for delivering fluid from said outlet of said fluid delivery assembly, said fluid delivery means comprising a quick connect delivery fitting removably connected to said base;

(b) a fluid containing subassembly interconnected with said fluid delivery assembly for filling said reservoir thereof, said fluid containing subassembly comprising:

(i) a container assembly including:

a. a container having a body portion, a fluid chamber, and first and second open ends;

b. closure means for sealably closing said first end of said container said closure means being pierceable by said hollow cannula of said cover overlay; and c. a plunger telescopically movable within said container from a first location proximate said open end to a second spaced apart location to cause fluid within said fluid chamber to flow into said hollow cannula; and (ii) an adapter assembly receivable within said chamber of said cover assembly, said adapter assembly comprising a hollow housing having a first open end for telescopically receiving a part of said body portion of said container of said container assembly and including a second end, said hollow housing having a plurality of longitudinally spaced teeth engageable by said drive wheel of said fluid delivery assembly for controllably advancing said adapter assembly within said receiving chamber.

3. An apparatus as defined in claim 2 further including locking means for releasably locking said quick connect delivery fitting to said base.

4. A fluid delivery apparatus comprising:

(a) a fluid delivery assembly having an outlet for delivering fluid from the apparatus, said fluid delivery assembly including:

(i) a base;

(ii) a cover assembly connected to said base, one of said cover assembly and said base having a fluid passageway in communication with said outlet and one of said cover assembly and said base having first and second receiving chambers interconnected with said fluid passageway;

(iii) operating means for urging controlled fluid flow through said outlet, said operating means including drive means carried by said base; and (iv) a stored energy means for cooperation with said base to define a fluid reservoir having a fluid inlet in communication with said fluid passageway, said stored energy means being energizable by forces imparted thereon by fluids introduced into said reservoir through said fluid inlet, said forces establishing internal stresses within said stored energy means, said stresses tending to return said stored energy means toward a less energized configuration; and (b) a first fluid containing subassembly interconnected with said fluid delivery assembly for filling said reservoir, said first fluid containing subassembly comprising:

(i) a first container assembly for containing fluid; and (ii) a first adapter assembly receivable within said first receiving chamber of said fluid delivery assembly, said first adapter assembly comprising a first housing for telescopically receiving a part of said first container assembly;

(c) a second fluid containing subassembly interconnected with said fluid delivery assembly for delivering fluid to said outlet of said second fluid containing subassembly comprising:

(i) a second container assembly for containing fluid; and (ii) a second adapter assembly receivable within said second receiving chamber of said fluid delivery assembly, said second adapter assembly comprising a second housing for telescopically receiving a part of said second container assembly, said second housing having driven means engageable by said drive means of said operating means of said fluid delivery assembly for advancing said second adapter assembly within said second receiving chamber.

5. An apparatus as defined in claim 4 in which said drive means of said operating means comprises a drive wheel rotatably carried by one of said base and said cover assembly and in which said drive means comprises a plurality of outwardly extending, longitudinally spaced teeth provided on said second housing of said second adapter assembly, said teeth being engageable by said drive wheel to impart movement to said housing of said adapter assembly.

6. An apparatus as defined in claim 4 in which said stored energy means comprises a part of a reservoir unit which is detachably connected to said base, said unit having a fluid outlet in communication with said fluid passageway.

7. An apparatus as defined in claim 4 in which said stored energy means comprises a distendable membrane sealably connected to said base, said distendable membrane being distendable by fluids introduced into said reservoir.

8. An apparatus as defined in claim 4 further including fluid delivery means for delivering fluid from said outlet of said fluid delivery assembly.

9. An apparatus as defined in claim 4 in which said fluid reservoir defining means further includes a barrier member sealably interconnected with said base.

10. An apparatus as defined in claim 4 in which said conformable ullage comprises an elastomer.

11. An apparatus as defined in claim 4 in which said conformable ullage comprises a gel.

12. An apparatus as defined in claim 4 in which said conformable ullage comprises a flowable substance.

13. An apparatus as defined in claim 4 in which said fluid delivery assembly further includes flow control means for controlling fluid flow through said outlet, said flow control means comprising first and second porous members.

14. An apparatus as defined in claim 13 in which said operating means further includes control means for controlling rotation of said drive wheel.

15. An apparatus as defined in claim 13 in which said control means comprises a dosing indicator disc connected to said drive wheel and a safety interlocking means for controlling rotation of said indexing disc.

16. An apparatus as defined in claim 13 further including locking means for locking said first adapter assembly within said receiving chamber.

17. A fluid delivery apparatus for delivering fluid into a patient comprising:
   (a) a fluid delivery assembly having an outlet for delivering fluid from the apparatus, said fluid delivery assembly including:
      (i) a base having a fluid passageway in communication with said outlet and having first and second ends;
      (ii) operating means for urging controlled fluid flow through said outlet, said operating means including drive means carried by said base;
      (iii) a cover assembly connected to said base, one of said cover assembly and said base having a receiving chamber interconnected with said first end of said fluid passageway formed in said base; and
      (iv) a stored energy means comprising at lease one distendable membrane superimposed over said upper surface of said base to define a fluid reservoir having a fluid inlet in communication with said fluid passageway in said base, said membrane being distendable by forces imparted thereon by fluids introduced into said reservoir through said fluid inlet, said forces establishing internal stresses within said distendable membrane, said stresses tending to return said distendable membrane toward a less distended configuration; and
   (b) a fluid containing subassembly interconnected with said fluid delivery assembly for filling said reservoir, said fluid containing subassembly comprising:
      (i) a container assembly for containing fluid; and
      (ii) an adapter assembly receivable within said receiving chamber, said adapter assembly comprising a hollow housing having an internal chamber for receiving a part of said container of said container assembly, said hollow housing having driven means engageable by said drive means of said fluid delivery assembly for advancing said adapter assembly within said receiving chamber.

\* \* \* \* \*